(12) United States Patent
Hamada et al.

(10) Patent No.: US 11,043,637 B2
(45) Date of Patent: Jun. 22, 2021

(54) LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Takao Hamada, Kanagawa (JP); Hiromi Seo, Kanagawa (JP); Kanta Abe, Kanagawa (JP); Kyoko Takeda, Kanagawa (JP); Satoshi Seo, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 307 days.

(21) Appl. No.: 15/999,406

(22) Filed: Aug. 20, 2018

(65) Prior Publication Data
US 2019/0013468 A1    Jan. 10, 2019

Related U.S. Application Data

(63) Continuation of application No. 15/228,557, filed on Aug. 4, 2016, now Pat. No. 10,069,076, which is a
(Continued)

(30) Foreign Application Priority Data

Aug. 3, 2012  (JP) .................................. 2012-172944
Mar. 7, 2013  (JP) .................................. 2013-045127

(51) Int. Cl.
*H01L 51/50* (2006.01)
*H01L 51/00* (2006.01)
(Continued)

(52) U.S. Cl.
CPC .......... *H01L 51/006* (2013.01); *C07D 209/86* (2013.01); *C09K 11/025* (2013.01);
(Continued)

(58) Field of Classification Search
CPC ............. H01L 51/5016; H01L 51/0072; H01L 51/5024; H01L 2251/5384; H01L 51/0058;
(Continued)

(56) References Cited

U.S. PATENT DOCUMENTS 5,061,569 A    10/1991  VanSlyke et al.
5,163,837 A    11/1992  Rowlette, Sr.
(Continued)

FOREIGN PATENT DOCUMENTS

CN    001462303 A    12/2003
CN    001702065 A    11/2005
(Continued)

OTHER PUBLICATIONS

Seo.S et al., "Exciplex-triplet energy transfer: A new method to achieve extremely efficient organic light-emitting diode with external quantum efficiency over 30% and drive voltage below 3V", Jpn. J. Appl. Phys. (Japanese Journal of Applied Physics) , Mar. 17, 2014, vol. 53, No. 4, pp. 042102-1-042102-8.
(Continued)

*Primary Examiner* — Gregory D Clark
(74) *Attorney, Agent, or Firm* — Fish & Richardson P.C.

(57) ABSTRACT

A light-emitting element having a long lifetime is provided. A light-emitting element exhibiting high emission efficiency in a high luminance region is provided. A light-emitting element includes a light-emitting layer between a pair of electrodes. The light-emitting layer contains a first organic compound, a second organic compound, and a phosphorescent compound. The first organic compound is represented by a general formula (G0). The molecular weight of the first organic compound is greater than or equal to 500 and less than or equal to 2000. The second organic compound is a compound having an electron-transport property. In the
(Continued)

general formula (G0), $Ar^1$ and $Ar^2$ each independently represent a fluorenyl group, a spirofluorenyl group, or a biphenyl group, and $Ar^3$ represents a substituent including a carbazole skeleton.

16 Claims, 33 Drawing Sheets

Related U.S. Application Data continuation of application No. 13/957,082, filed on Aug. 1, 2013, now Pat. No. 9,412,962.

(51) Int. Cl.
- *C07D 209/86* (2006.01)
- *C09K 11/02* (2006.01)
- *C09K 11/06* (2006.01)

(52) U.S. Cl.
CPC .......... *C09K 11/06* (2013.01); *H01L 51/0061* (2013.01); *H01L 51/0067* (2013.01); *H01L 51/0072* (2013.01); *H01L 51/0074* (2013.01); *H01L 51/0085* (2013.01); *H01L 51/5016* (2013.01); *H01L 51/5024* (2013.01); *C09K 2211/1007* (2013.01); *C09K 2211/1044* (2013.01); *C09K 2211/185* (2013.01); *H01L 51/0052* (2013.01); *H01L 51/0056* (2013.01); *H01L 51/0058* (2013.01); *H01L 51/5056* (2013.01); *H01L 51/5072* (2013.01); *H01L 2251/5384* (2013.01)

(58) Field of Classification Search
CPC ............. H01L 51/0056; H01L 51/5056; H01L 51/5012; H01L 51/006; H01L 51/0059; H01L 51/0052; H01L 51/0074; C07D 209/86; C07D 333/76; C07C 2603/97; C07C 211/58; C07C 211/61; C07C 211/54; C09K 2211/1007; C09K 2211/1014; C09K 2211/1092; C09K 2211/1022; C09K 11/06
See application file for complete search history.

(56) References Cited

U.S. PATENT DOCUMENTS

| | | |
|---|---|---|
| 6,984,462 B2 | 1/2006 | Kim et al. |
| 6,998,487 B2 | 2/2006 | Kim et al. |
| 7,175,922 B2 | 2/2007 | Jarikov et al. |
| 7,183,010 B2 | 2/2007 | Jarikov |
| 7,332,857 B2 | 2/2008 | Seo et al. |
| 7,431,997 B2 | 10/2008 | Hwang et al. |
| 7,572,522 B2 | 8/2009 | Seo et al. |
| 7,597,967 B2 | 10/2009 | Kondakova et al. |
| 7,737,627 B2 | 6/2010 | Hwang et al. |
| 7,816,668 B2 | 10/2010 | Kawakami et al. |
| 7,838,128 B2 | 11/2010 | Kawakami et al. |
| 7,897,964 B2 | 3/2011 | Kawakami et al. |
| 7,943,925 B2 | 5/2011 | Yamazaki |
| 7,993,760 B2 | 8/2011 | Komori et al. |
| 8,021,764 B2 | 9/2011 | Hwang et al. |
| 8,021,765 B2 | 9/2011 | Hwang et al. |
| 8,034,465 B2 | 10/2011 | Liao et al. |
| 8,188,315 B2 | 5/2012 | Hwang et al. |
| 8,247,086 B2 | 8/2012 | Inoue et al. |
| 8,274,214 B2 | 9/2012 | Ikeda et al. |
| 8,395,143 B2 | 3/2013 | Lee et al. |
| 8,652,654 B2 | 2/2014 | Inoue et al. |
| 8,710,493 B2 | 4/2014 | Nishimura et al. |
| 8,853,680 B2 | 10/2014 | Yamazaki et al. |
| 8,865,323 B2 | 10/2014 | Inoue et al. |
| 8,877,352 B2 | 11/2014 | Inoue et al. |
| 8,940,414 B2 | 1/2015 | Inoue et al. |
| 8,963,127 B2 | 2/2015 | Pieh et al. |
| 8,968,884 B2 | 3/2015 | Hong et al. |
| 8,974,922 B2 | 3/2015 | Hwang et al. |
| 8,981,355 B2 | 3/2015 | Seo |
| 8,987,715 B2 | 3/2015 | Nishimura et al. |
| 8,993,129 B2 | 3/2015 | Endo et al. |
| 8,994,263 B2 | 3/2015 | Shitagaki et al. |
| 9,054,317 B2 | 6/2015 | Monkman et al. |
| 9,130,174 B2 | 9/2015 | Mizuki et al. |
| 9,133,119 B2 | 9/2015 | Parham et al. |
| 9,139,522 B2 | 9/2015 | Yabunouchi et al. |
| 9,159,942 B2 | 10/2015 | Seo et al. |
| 9,174,938 B2 | 11/2015 | Jinde et al. |
| 9,175,213 B2 | 11/2015 | Seo et al. |
| 9,260,390 B2 | 2/2016 | Kato |
| 9,356,250 B2 | 5/2016 | Ohsawa et al. |
| 9,412,962 B2 | 8/2016 | Hamada et al. |
| 9,434,877 B2 | 9/2016 | Pflumm et al. |
| 9,478,754 B2 | 10/2016 | Hwang et al. |
| 9,604,928 B2 | 3/2017 | Shitagaki et al. |
| 9,917,258 B2 | 3/2018 | Hwang et al. |
| 10,069,076 B2 | 9/2018 | Hamada et al. |
| 10,211,406 B2 | 2/2019 | Hwang et al. |
| 2002/0074935 A1 | 6/2002 | Kwong et al. |
| 2003/0175553 A1 | 9/2003 | Thompson et al. |
| 2004/0151943 A1 | 8/2004 | Lee et al. |
| 2005/0048310 A1 | 3/2005 | Cocchi et al. |
| 2005/0196775 A1 | 9/2005 | Swager et al. |
| 2005/0221116 A1 | 10/2005 | Cocchi et al. |
| 2005/0221124 A1 | 10/2005 | Hwang et al. |
| 2005/0225235 A1 | 10/2005 | Kim et al. |
| 2006/0134464 A1 | 6/2006 | Nariyuki |
| 2006/0228577 A1 | 10/2006 | Nagara |
| 2007/0090756 A1 | 4/2007 | Okada et al. |
| 2007/0145888 A1 | 6/2007 | Yabunouchi et al. |
| 2007/0215867 A1 | 9/2007 | Kawakami et al. |
| 2007/0222374 A1 | 9/2007 | Egawa et al. |
| 2007/0231503 A1 | 10/2007 | Hwang et al. |
| 2007/0244320 A1 | 10/2007 | Inoue et al. |
| 2008/0014464 A1 | 1/2008 | Kawamura et al. |
| 2008/0124572 A1 | 5/2008 | Mizuki et al. |
| 2008/0160345 A1 | 7/2008 | Inoue et al. |
| 2008/0242871 A1 | 10/2008 | Kawakami et al. |
| 2008/0268282 A1 | 10/2008 | Spindler et al. |
| 2008/0286604 A1 | 11/2008 | Inoue et al. |
| 2009/0058261 A1 | 3/2009 | Kawakami et al. |
| 2009/0160323 A1 | 6/2009 | Nomura et al. |
| 2009/0284140 A1 | 11/2009 | Osaka et al. |
| 2009/0302313 A1 | 12/2009 | Choi et al. |
| 2010/0052527 A1 | 3/2010 | Ikeda et al. |
| 2010/0133519 A1 | 6/2010 | Chen et al. |
| 2010/0145044 A1 | 6/2010 | Inoue et al. |
| 2010/0244008 A1 | 9/2010 | Lee et al. |
| 2010/0301312 A1 | 12/2010 | Jinde et al. |
| 2011/0001146 A1 | 1/2011 | Yamazaki et al. |
| 2011/0042654 A1 | 2/2011 | Jung et al. |
| 2011/0127495 A1 | 6/2011 | Hong et al. |
| 2011/0147728 A1 | 6/2011 | Kawakami et al. |
| 2011/0198581 A1 | 8/2011 | Yabunouchi et al. |
| 2011/0210316 A1 | 9/2011 | Kadoma et al. |
| 2011/0215714 A1 | 9/2011 | Seo et al. |
| 2011/0278555 A1 | 11/2011 | Inoue et al. |
| 2011/0279020 A1 | 11/2011 | Inoue et al. |
| 2012/0037894 A1 | 2/2012 | Okabe |
| 2012/0098417 A1 | 4/2012 | Inoue et al. |
| 2012/0119197 A1 | 5/2012 | Nishimura et al. |
| 2012/0138912 A1 | 6/2012 | Inoue et al. |
| 2012/0146014 A1 | 6/2012 | Kato |
| 2012/0197020 A1 | 8/2012 | Osaka et al. |
| 2012/0205632 A1 | 8/2012 | Shitagaki et al. |
| 2012/0205687 A1 | 8/2012 | Yamazaki et al. |
| 2012/0206035 A1 | 8/2012 | Shitagaki et al. |
| 2012/0217486 A1 | 8/2012 | Takemura et al. |
| 2012/0217487 A1 | 8/2012 | Yamazaki et al. |
| 2012/0242219 A1 | 9/2012 | Seo et al. |
| 2012/0248421 A1 | 10/2012 | Yamazaki et al. |
| 2012/0256535 A1 | 10/2012 | Seo et al. |
| 2012/0292576 A1 | 11/2012 | Parham et al. |

(56) References Cited

U.S. PATENT DOCUMENTS

| | | |
|---|---|---|
| 2012/0326141 A1 | 12/2012 | Pflumm et al. |
| 2013/0048964 A1 | 2/2013 | Takeda et al. |
| 2013/0075716 A1 | 3/2013 | Nishimura et al. |
| 2013/0134402 A1 | 5/2013 | Tanaka et al. |
| 2013/0264548 A1 | 10/2013 | Mizuki et al. |
| 2013/0270530 A1 | 10/2013 | Watanabe et al. |
| 2014/0034928 A1 | 2/2014 | Shitagaki et al. |
| 2014/0217378 A1 | 8/2014 | Nishimura et al. |
| 2015/0008423 A1 | 1/2015 | Inoue et al. |
| 2015/0069352 A1 | 3/2015 | Kim et al. |
| 2015/0179943 A1* | 6/2015 | Sato .......... H01L 51/5231 257/40 |
| 2015/0221872 A1 | 8/2015 | Hwang et al. |
| 2015/0228912 A1 | 8/2015 | Inoue et al. |
| 2015/0340613 A1 | 11/2015 | Parham et al. |
| 2016/0064669 A1 | 3/2016 | Kato |
| 2018/0009751 A1 | 1/2018 | Nomura et al. |
| 2019/0157568 A1 | 5/2019 | Hwang et al. |

FOREIGN PATENT DOCUMENTS

| | | |
|---|---|---|
| CN | 101535256 A | 9/2009 |
| CN | 101855315 A | 10/2010 |
| CN | 101896574 A | 11/2010 |
| CN | 101904028 A | 12/2010 |
| CN | 101952250 A | 1/2011 |
| CN | 102186819 A | 9/2011 |
| CN | 102190653 A | 9/2011 |
| CN | 102349172 A | 2/2012 |
| CN | 102421772 A | 4/2012 |
| CN | 102439004 A | 5/2012 |
| CN | 102482215 A | 5/2012 |
| CN | 102725268 A | 10/2012 |
| CN | 102782084 A | 11/2012 |
| CN | 102986052 A | 3/2013 |
| CN | 103254113 A | 8/2013 |
| CN | 103620808 A | 3/2014 |
| DE | 102010005697 | 7/2011 |
| DE | 102010010481 | 9/2011 |
| EP | 1202608 A | 5/2002 |
| EP | 1645552 A | 4/2006 |
| EP | 1661888 A | 5/2006 |
| EP | 1862524 A | 12/2007 |
| EP | 1950194 A | 7/2008 |
| EP | 1972619 A | 9/2008 |
| EP | 2085382 A | 8/2009 |
| EP | 2224510 A | 9/2010 |
| EP | 2225204 A | 9/2010 |
| EP | 2333862 A | 6/2011 |
| EP | 2348017 A | 7/2011 |
| EP | 2363398 A | 9/2011 |
| EP | 2366753 A | 9/2011 |
| EP | 2415769 A | 2/2012 |
| EP | 2423209 A | 2/2012 |
| EP | 2468725 A | 6/2012 |
| EP | 2581957 A | 4/2013 |
| EP | 2592671 A | 5/2013 |
| EP | 2757094 A | 7/2014 |
| JP | 63-014156 A | 1/1988 |
| JP | 08-124677 A | 5/1996 |
| JP | 09-310066 A | 12/1997 |
| JP | 2002-241352 A | 8/2002 |
| JP | 2003-089682 A | 3/2003 |
| JP | 2004-515895 | 5/2004 |
| JP | 2006-203172 A | 8/2006 |
| JP | 2007-015933 A | 1/2007 |
| JP | 2007-045816 A | 2/2007 |
| JP | 2007-110093 A | 4/2007 |
| JP | 2007-119457 A | 5/2007 |
| JP | 2007-520470 | 7/2007 |
| JP | 2008-266309 A | 11/2008 |
| JP | 2008-288344 A | 11/2008 |
| JP | 2009-298767 A | 12/2009 |
| JP | 2011-001349 * 1/2011 ............ C09K 11/06 | |
| JP | 2011-503055 | 1/2011 |
| JP | 2011-503555 | 1/2011 |
| JP | 2011-128275 A | 6/2011 |
| JP | 2011-129275 A | 6/2011 |
| JP | 2011-201869 A | 10/2011 |
| JP | 2011-204673 A | 10/2011 |
| JP | 2012-004526 A | 1/2012 |
| JP | 2012-033918 A | 2/2012 |
| JP | 2012-080063 A | 4/2012 |
| JP | 2012-097091 A | 5/2012 |
| JP | 5074627 | 11/2012 |
| JP | 2013-030781 A | 2/2013 |
| JP | 2013-065867 A | 4/2013 |
| JP | 2013-515361 | 5/2013 |
| JP | 2013-518068 | 5/2013 |
| JP | 2013-128139 A | 6/2013 |
| JP | 2013-522864 | 6/2013 |
| JP | 2013-201153 A | 10/2013 |
| JP | 2014-040423 A | 3/2014 |
| JP | 6267888 | 1/2018 |
| KR | 2005-0097670 A | 10/2005 |
| KR | 2009-0041999 A | 4/2009 |
| KR | 2009-0048299 A | 5/2009 |
| KR | 2009-0112137 A | 10/2009 |
| KR | 2010-0099250 A | 9/2010 |
| KR | 2010-0106415 A | 10/2010 |
| KR | 2011-0069077 A | 6/2011 |
| KR | 2011-0088898 A | 8/2011 |
| KR | 2011-0099173 A | 9/2011 |
| KR | 2011-0099645 A | 9/2011 |
| KR | 2011-0134399 A | 12/2011 |
| KR | 2012-0034648 A | 4/2012 |
| KR | 2012-0057561 A | 6/2012 |
| KR | 2012-0129922 A | 11/2012 |
| KR | 2012-0135325 A | 12/2012 |
| KR | 2013-0021350 A | 3/2013 |
| KR | 2013-0038218 A | 4/2013 |
| KR | 2014-0043091 A | 4/2014 |
| TW | 200838850 | 10/2008 |
| TW | 200927730 | 7/2009 |
| TW | 200936545 | 9/2009 |
| TW | 200946501 | 11/2009 |
| TW | 201041436 | 11/2010 |
| TW | 201139608 | 11/2011 |
| TW | 201141989 | 12/2011 |
| TW | 201141990 | 12/2011 |
| TW | 201212330 | 3/2012 |
| TW | 201213497 | 4/2012 |
| TW | 201233711 | 8/2012 |
| TW | 201233773 | 8/2012 |
| TW | 201305314 | 2/2013 |
| TW | 201320426 | 5/2013 |
| TW | 201343637 | 11/2013 |
| WO | WO-2000/070655 | 11/2000 |
| WO | WO-2002/088274 | 11/2002 |
| WO | WO-2003/059015 | 7/2003 |
| WO | WO-2005/090512 | 9/2005 |
| WO | WO-2006/033857 | 3/2006 |
| WO | WO-2007/007885 | 1/2007 |
| WO | WO-2007/043354 | 4/2007 |
| WO | WO-2007/148660 | 12/2007 |
| WO | WO-2008/062636 | 5/2008 |
| WO | WO-2008/069756 | 6/2008 |
| WO | WO-2009/035296 | 3/2009 |
| WO | WO-2009/061145 | 5/2009 |
| WO | WO-2009/061156 | 5/2009 |
| WO | WO-2009/072587 | 6/2009 |
| WO | WO-2009/081857 | 7/2009 |
| WO | WO-2010/044130 | 4/2010 |
| WO | WO-2010/104184 | 9/2010 |
| WO | WO-2011/076323 | 6/2011 |
| WO | WO-2011/088877 | 7/2011 |
| WO | WO-2011/110262 | 9/2011 |
| WO | WO-2011/132683 | 10/2011 |
| WO | WO-2011/132684 | 10/2011 |
| WO | WO-2011/148909 | 12/2011 |
| WO | WO-2011/155507 | 12/2011 |
| WO | WO-2012/005329 | 1/2012 |
| WO | WO-2012/026780 | 3/2012 |

(56) References Cited

FOREIGN PATENT DOCUMENTS

| WO | WO-2012/033063 | 3/2012 |
|---|---|---|
| WO | WO-2012/096263 | 7/2012 |
| WO | WO-2012/096352 | 7/2012 |
| WO | WO-2012/176818 | 12/2012 |
| WO | WO-2013/069338 | 5/2013 |
| WO | WO-2013/129491 | 9/2013 |
| WO | WO-2014/021441 | 2/2014 |

OTHER PUBLICATIONS

Song.W et al., "Light emission mechanism of mixed host organic light-emitting diodes", Appl. Phys. Lett. (Applied Physics Letters) , Mar. 1, 2015, vol. 106, No. 12, pp. 123306-1-123306-4.
Tris[2-phenylpyridinato-C2,N]iridium(III), https://www.sigmaaldrich.com/catalog/product/aldrich/688096?lang=de&region=DE.
Organic Light-emitting Materials and Devices, 2007, pp. 330-334, Taylor & Francis Group.
Rho.H et al., "Synthesis and Photophysical Studies of Iridium Complexes Having Different Ligands", Jpn. J. Appl. Phys. (Japanese Journal of Applied Physics) , Jan. 20, 2006, vol. 45, No. 1B, pp. 568-573.
Negres.R et al., "Origin of efficient light emission from a phosphorescent polymer/organometallic guest-host system", Phys. Rev. B (Physical Review. B), Sep. 29, 2003, vol. 68, No. 11, pp. 115209-1-115209-8.
Gong.X et al., "High-Efficiency Polymer-Based Electrophosphorescent Devices", Adv. Mater. (Advanced Materials), Apr. 18, 2002, vol. 14, No. 8, pp. 581-585.
Hamed.Z et al., "Fluorescence quenching in PVK:ZnSe nanocomposite structure", Synthetic Metals, Jun. 12, 2014, vol. 195, pp. 102-109.
Holzer.W et al., "Absorption and emission spectroscopic characterization of Ir(ppy)3", Chemical Physics, 2005, vol. 308, No. 1-2, pp. 93-102.
Tamayo.A et al., "Synthesis and Characterization of Facial and Meridional Tris-cyclometalated Iridium (III) Complexes", J. Am. Chem. Soc. (Journal of the American Chemical Society), Jun. 18, 2003, vol. 125, No. 24, pp. 7377-7387.
Okada.S et al., "Substituent effects of iridium complexes for highly efficient red OLEDs", Dalton Transactions, May 5, 2005, No. 9, pp. 1583-1590.
Notice of Opposition (Patent number. German Patent No. 112012000831) dated Jun. 4, 2018.
Notice of Opposition (Patent number. German Patent No. 112012000828) dated Jun. 8, 2018.
Notice of Opposition (Patent number. German Patent No. 112012001364) dated Jun. 27, 2018.
Petition for Cancellation of Patent (Patent number. Korean Patent No. 10-1793880-00-00) dated May 24, 2018.
Petition for Cancellation of Patent (Patent number. Korean Patent No. 10-1812673-00-00) dated Jul. 6, 2018.
Written Opposition to the Grant of Patent (Patent number. Japanese Patent No. 5981726) dated Feb. 28, 2017.
Kondakova.M et al., "High-efficiency, low-voltage phosphorescent organic light-emitting diode devices with mixed host", J. Appl. Phys. (Journal of Applied Physics) , Nov. 4, 2008, vol. 104, pp. 094501-1-094501-17.
Seo.J et al., "Efficient blue-green organic light-emitting diodes based on heteroleptic tris-cyclometalated iridium(III) complexes", Thin Solid Films, Sep. 25, 2008, vol. 517, No. 5, pp. 1807-1810.
Ho.M et al., "P-131: Novel Deep Blue Dopants for Organic Light Emitting Devices", SID Digest '05 : SID International Symposium Digest of Technical Papers, May 24, 2005, vol. 36, pp. 802-805.
Goldsmith.C et al., "C—H Bond Activation by a Ferric Methoxide Complex: Modeling the Rate—Determining Step in the Mechanism of Lipoxygenase", J. Am. Chem. Soc. (Journal of the American Chemical Society), 2002, vol. 124, No. 1, pp. 83-96.
Onishi.T et al., "A Method of Measuring an Energy Level", High Molecular EL Materials—Development of Light-Emitting High Molecular Compounds, Dec. 25, 2004, pp. 64-67, Kyoritsu Shuppan.
Promarak.V et al., "Synthesis and Properties of Stable Amorphous Hole-Transporting Molecules for Electroluminescent Devices", Tetrahedron Letters, 2006, vol. 47, No. 50, pp. 8949-8952.
International Search Report (Application No. PCT/JP2008/072104) dated Jan. 13, 2009.
Written Opinion (Application No. PCT/JP2008/072104) dated Jan. 13, 2009.
International Search Report (Application No. PCT/JP2009/058787) dated Aug. 11, 2009.
Written Opinion (Application No. PCT/JP2009/058787) dated Aug. 11, 2009.
Changqi.M et al., "Progress in Hole-Transport Materials for Use in Organic Light-Emitting Diodes", Progress in Chemistry, Nov. 1, 2003, vol. 15, No. 6, pp. 495-504.
Notice of Division of Application (Application No. 200880126449.5) dated May 3, 2012.
Shen.J et al., "Ambipolar Conductive 2,7-Carbazole Derivatives for Electroluminescent Devices", Adv. Funct. Mater. (Advanced Functional Materials), 2007, vol. 17, No. 6, pp. 983-995.
European Search Report (Application No. 08858330.7) dated Sep. 28, 2012.
International Search Report (Application No. PCT/JP2013/070949) dated Nov. 12, 2013.
Written Opinion (Application No. PCT/JP2013/070949) dated Nov. 12, 2013.
Baldo.M et al., "Highly Efficient Phosphorescent Emission From Organic Electroluminescent Devices", Nature, Sep. 10, 1998, vol. 395, pp. 151-154.
Baldo.M et al., "Very High-Efficiency Green Organic Light-Emitting Devices Based on Electrophosphorescence", Appl. Phys. Lett. (Applied Physics Letters) , Jul. 5, 1999, vol. 75, No. 1, pp. 4-6.
Gu.G et al., "Transparent Organic Light Emitting Devices", Appl. Phys. Lett. (Applied Physics Letters) , May 6, 1996, vol. 68, No. 19, pp. 2606-2608.
Choong.V et al., "Organic Light-Emitting Diodes With a Bipolar Transport Layer", Appl. Phys. Lett. (Applied Physics Letters) , Jul. 12, 1999, vol. 75, No. 2, pp. 172-174.
Adachi.C et al., "Nearly 100% Internal Phosphorescence Efficiency in an Organic Light Emitting Device", J. Appl. Phys. (Journal of Applied Physics) , Nov. 15, 2001, vol. 90, No. 10, pp. 5048-5051.
Baldo.M et al., "Prospects for Electrically Pumped Organic Lasers", Phys. Rev. B (Physical Review. B), Jul. 19, 2002, vol. 66, pp. 035321-1-035321-16.
Markham.J et al., "High-efficiency green phosphorescence from spin-coated single-layer dendrimer light-emitting diodes", Appl. Phys. Lett. (Applied Physics Letters) , Apr. 15, 2002, vol. 80, No. 15, pp. 2645-2647.
Itano.K et al., "Exciplex formation at the organic solid-state interface: Yellow emission in organic light-emitting diodes using green-fluorescent tris(8-quinolinolato)aluminum and hole-transporting molecular materials with low ionization potentials", Appl. Phys. Lett. (Applied Physics Letters) , Feb. 9, 1998, vol. 72, No. 6, pp. 636-638.
Fujita.M et al., "Reduction of operating voltage in organic light-emitting diode by corrugated photonic crystal structure", Appl. Phys. Lett. (Applied Physics Letters) , Dec. 6, 2004, vol. 85, No. 23, pp. 5769-5771.
Chinese Office Action (Application No. 201380041236.3) dated Apr. 22, 2016.
Taiwanese Office Action (Application No. 102127433) dated Nov. 22, 2016.
Yersin.H et al., "Triplet Emitters for Organic Light-Emitting Diodes: Basic Properties", Highly Efficient OLEDs with Phosphorescent Materials, 2008, pp. 1-18.
Jeon.W et al., "Ideal host and guest system in phosphorescent OLEDs", Organic Electronics, 2009, vol. 10, pp. 240-246, Elsevier.
Su.S et al., "RGB Phosphorescent Organic Light-Emitting Diodes by Using Host Materials with Heterocyclic Cores:Effect of Nitrogen Atom Orientations", Chem. Mater. (Chemistry of Materials), 2011, vol. 23, No. 2, pp. 274-284.

(56) References Cited

OTHER PUBLICATIONS

Rausch.A et al., "Matrix Effects on the Triplet State of the OLED Emitter Ir(4,6-dFppy)2(pic)(FIrpic):Investigations by High-Resolution Optical Spectroscopy", Inorg. Chem. (Inorganic Chemistry), 2009, vol. 48, No. 5, pp. 1928-1937.

Gong.X et al., "Phosphorescence from iridium complexes doped into polymer blends", J. Appl. Phys. (Journal of Applied Physics), Feb. 1, 2004, vol. 95, No. 3, pp. 948-953.

Zhao.Q et al., "Synthesis and Photophysical, Electrochemical, and Electrophosphorescent Properties of a Series of Iridium(III) Complexes Based on Quinoline Derivatives and Different β-Diketonate Ligands", Organometallics, Jun. 14, 2006, vol. 25, No. 15, pp. 3631-3638.

Hino.Y et al., "Red Phosphorescent Organic Light-Emitting Diodes Using Mixture System of Small-Molecule and Polymer Host", Jpn. J. Appl. Phys. (Japanese Journal of Applied Physics), Apr. 21, 2005, vol. 44, No. 4B, pp. 2790-2794.

Tsuboyama.A et al., "Homoleptic Cyclometalated Iridium Complexes with Highly Efficient Red Phosphorescence and Application to Organic Light-Emitting Diode", J. Am. Chem. Soc. (Journal of the American Chemical Society), 2003, vol. 125, No. 42, pp. 12971-12979.

Chen.F et al., "Triplet Exciton Confinement in Phosphorescent Polymer Light-Emitting Diodes", Appl. Phys. Lett. (Applied Physics Letters), Feb. 17, 2003, vol. 82, No. 7, pp. 1006-1008.

Lee.J et al., "Stabilizing the efficiency of phosphorescent organic light-emitting diodes", SPIE Newsroom, Apr. 21, 2008, pp. 1-3.

Tokito.S et al., "Confinement of Triplet Energy on Phosphorescent Molecules for Highly Efficient Organic Blue-Light-Emitting Devices", Appl. Phys. Lett. (Applied Physics Letters), Jul. 21, 2003, vol. 83, No. 3, pp. 569-571.

Endo.A et al., "Efficient Up-Conversion of Triplet Excitons Into a Singlet State and Its Application for Organic Light Emitting Diodes", Appl. Phys. Lett. (Applied Physics Letters), Feb. 24, 2011, vol. 98, No. 8, pp. 083302-1-083302-3.

Yersin.H et al., Highly Efficient OLEDs with Phosphorescent Materials, 2008, pp. 1-97,283-309.

Tokito.S et al., "Improvement in performance by doping", Organic EL Display, Aug. 20, 2004, pp. 67-99, Ohmsha.

Park.Y et al., "Efficient triplet harvesting by fluorescent molecules through exciplexes for high efficiency organic light-emitting diodes", Appl. Phys. Lett. (Applied Physics Letters), Apr. 18, 2013, vol. 102, No. 15, pp. 153306-1-153306-5.

Chin.B, "Enhancement of efficiency and stability of phosphorescent OLEDs based on heterostructured light-emitting layers", J. Phys. D: Appl. Phys. (Journal of Physics D: Applied Physics), Mar. 23, 2011, vol. 44, No. 11, pp. 115103-1-115103-7, IOP Publishing.

Korean Office Action (Application No. 2015-7004006) dated Jul. 12, 2018.

Cai.C et al., "Efficient Low-Driving-Voltage Blue Phosphorescent Homojunction Organic Light-Emitting Devices", Jpn. J. Appl. Phys. (Japanese Journal of Applied Physics), Apr. 5, 2011, vol. 50, pp. 040204-1-040204-3.

Cai.C et al., "High-efficiency red, green and blue phosphorescent homojunction organic light-emitting diodes based on bipolar host materials", Organic Electronics, Feb. 17, 2011, vol. 12, No. 5, pp. 843-850.

Suzuki.K et al., "Photophysical study of iridium complexes by absolute photoluminescence quantum yield measurements using an integrating sphere ", Proceedings of SPIE, 2009, vol. 7415, pp. 741504-1-741504-8.

Goushi.K et al., "Efficient organic light-emitting diodes through up-conversion from triplet to singlet excited states of exciplexes", Appl. Phys. Lett. (Applied Physics Letters), Jul. 12, 2012, vol. 101, No. 2, pp. 023306-1-023306-4.

German Office Action (Application No. 112013007782.5) dated Mar. 28, 2021.

* cited by examiner

--- fluorescence spectrum of first organic compound 221
(or second organic compound 222)
-·-· phosphorescence spectrum of first organic compound 221
(or second organic compound 222)
—— absorption spectrum of phosphorescent compound 223
—— emission spectrum of exciplex

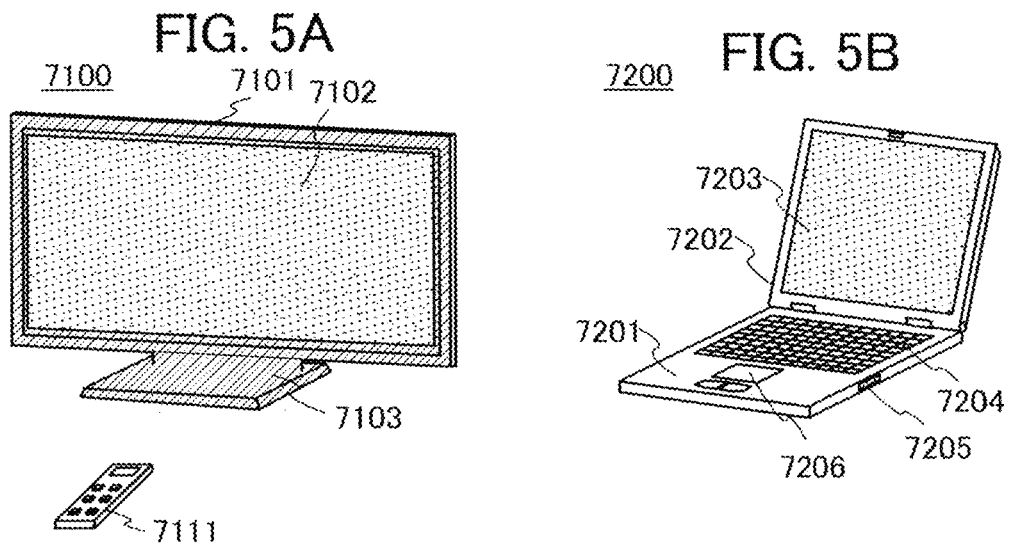
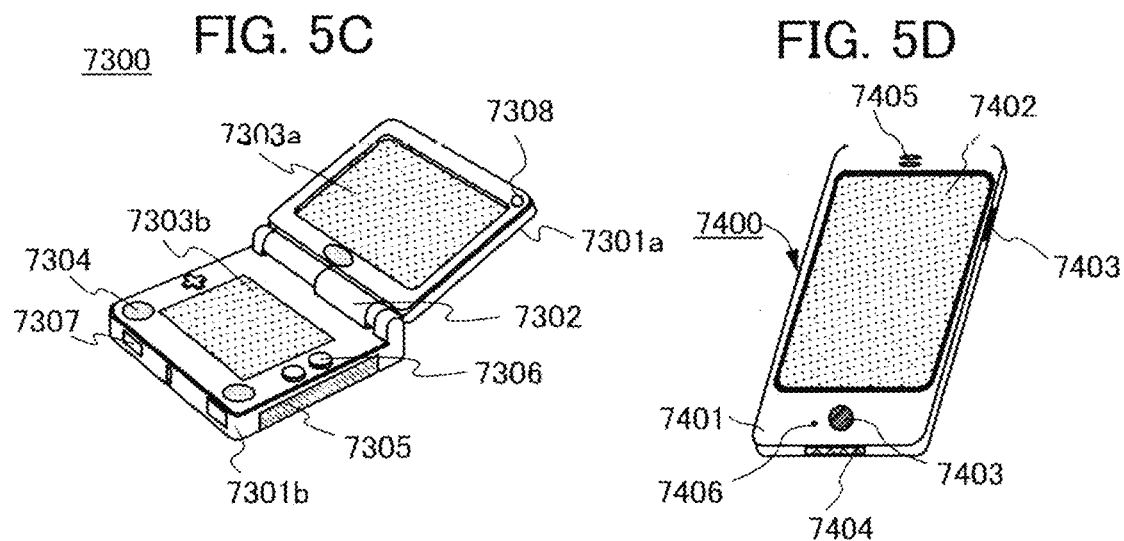
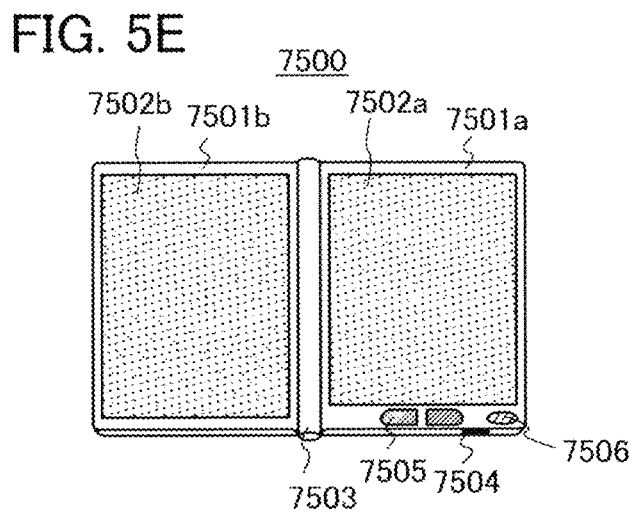

LIGHT-EMITTING ELEMENT, LIGHT-EMITTING DEVICE, ELECTRONIC DEVICE, AND LIGHTING DEVICE

This application is a continuation of copending U.S. application Ser. No. 15/228,557, filed on Aug. 4, 2016 which is a continuation of U.S. application Ser. No. 13/957,082, filed on Aug. 1, 2013 (now U.S. Pat. No. 9,412,962 issued Aug. 9, 2016) which are all incorporated herein by reference.

TECHNICAL FIELD

The present invention relates to a light-emitting element utilizing electroluminescence (EL) (also referred to as an EL element), a light-emitting device, an electronic device, and a lighting device.

BACKGROUND ART

In recent years, research and development have been extensively conducted on EL elements. In a basic structure of EL elements, a layer containing a light-emitting substance is provided between a pair of electrodes. By applying voltage to this element, light emission from the light-emitting substance can be obtained.

Since such an EL element is of self-light-emitting type, it is considered that the EL element has advantages over a liquid crystal display in that visibility of pixels is high, backlight is not required, and so on and is therefore suitable as flat panel display elements. In addition, it is also a great advantage that the EL element can be manufactured as a thin and lightweight element. Furthermore, very high speed response is also one of the features of such an element.

Since EL elements can be formed in the form of a film, they make it possible to provide planar light emission. Therefore, large-area elements can be easily formed. This feature is difficult to obtain with point light sources typified by incandescent lamps and LEDs or linear light sources typified by fluorescent lamps. Thus, EL elements also have great potential as planar light sources which can be applied to lighting devices and the like.

EL elements can be broadly classified according to whether the light-emitting substance is an organic compound or an inorganic compound. In the case of an organic EL element in which a layer containing an organic compound as the light-emitting substance is provided between a pair of electrodes, application of a voltage to the light-emitting element causes injection of electrons from the cathode and holes from the anode into the layer containing the organic compound, and thus a current flows. The injected electrons and holes then lead the organic compound to its excited state, whereby light emission is obtained from the excited organic compound.

The excited state of an organic compound can be a singlet excited state and a triplet excited state, and light emission from the singlet excited state (S*) is referred to as fluorescence, and light emission from the triplet excited state (T*) is referred to as phosphorescence.

In improving element characteristics of such a light-emitting element, there are a lot of problems which depend on a substance, and in order to solve the problems, improvement of an element structure, development of a substance, and the like have been carried out. For example, Patent Document 1 discloses an organic light-emitting element including a mixed layer containing an organic low molecular hole-transport substance, an organic low molecular electron-transport substance, and a phosphorescent dopant.

REFERENCE

[Patent Document 1] Japanese Translation of PCT International Application No. 2004-515895

DISCLOSURE OF INVENTION

The development of organic EL elements leaves room for improvement in terms of emission efficiency, reliability, cost, and the like.

For practical use of displays or lights with organic EL elements, organic EL elements are required to have longer lifetimes and exhibit higher emission efficiency in a high luminance region, for example.

Thus, an object of one embodiment of the present invention is to provide a light-emitting element having a long lifetime. Another object of one embodiment of the present invention is to provide a light-emitting element exhibiting high emission efficiency in a high luminance region.

Another object of one embodiment of the present invention is to provide a light-emitting device, an electronic device, and a lighting device each having high reliability by using the above light-emitting element.

A light-emitting element in one embodiment of the present invention includes a light-emitting layer between a pair of electrodes, and the light-emitting layer contains a first organic compound, a second organic compound, and a phosphorescent compound. The first organic compound is a tertiary amine and has a structure in which two substituents including a fluorene skeleton, a spirofluorene skeleton, or a biphenylene skeleton and one substituent including a carbazole skeleton are each bonded to a nitrogen atom directly. The molecular weight of the first organic compound is greater than or equal to 500 and less than or equal to 2000. The second organic compound is a compound having an electron-transport property. With the light-emitting layer having such a structure, the light-emitting element can have a long lifetime. In addition, the light-emitting element can exhibit high emission efficiency in a high luminance region.

Specifically, one embodiment of the present invention is a light-emitting element including a light-emitting layer between a pair of electrodes. The light-emitting layer contains a first organic compound, a second organic compound, and a phosphorescent compound. The first organic compound is represented by a general formula (G0). The molecular weight of the first organic compound is greater than or equal to 500 and less than or equal to 2000. The second organic compound is a compound having an electron-transport property.

[Chemical formula 1]

(G0)

In the general formula (G0), $Ar^1$ and $Ar^2$ each independently represent a substituted or unsubstituted fluorenyl group, a substituted or unsubstituted spirofluorenyl group, or a substituted or unsubstituted biphenyl group, and $Ar^3$ represents a substituent including a carbazole skeleton.

Another embodiment of the present invention is a light-emitting element including a light-emitting layer between a pair of electrodes. The light-emitting layer contains a first organic compound, a second organic compound, and a phosphorescent compound. The first organic compound is represented by a general formula (G1). The molecular weight of the first organic compound is greater than or equal to 500 and less than or equal to 2000. The second organic compound is a compound having an electron-transport property.

[Chemical formula 2]

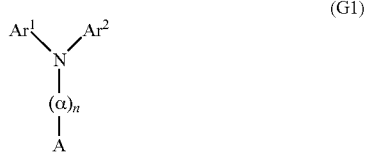
(G1)

In the general formula (G1), $Ar^1$ and $Ar^2$ each independently represent a substituted or unsubstituted fluorenyl group, a substituted or unsubstituted spirofluorenyl group, or a substituted or unsubstituted biphenyl group; α represents a substituted or unsubstituted phenylene group or a substituted or unsubstituted biphenyldiyl group; n represents 0 or 1; and A represents a substituted or unsubstituted 3-carbazolyl group.

Another embodiment of the present invention is a light-emitting element including a light-emitting layer between a pair of electrodes. The light-emitting layer contains a first organic compound, a second organic compound, and a phosphorescent compound. The first organic compound is represented by a general formula (G2). The molecular weight of the first organic compound is greater than or equal to 500 and less than or equal to 2000. The second organic compound is a compound having an electron-transport property.

[Chemical formula 3]

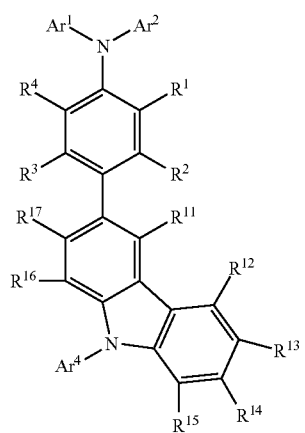
(G2)

In the general formula (G2), $Ar^1$ and $Ar^2$ each independently represent a substituted or unsubstituted fluorenyl group, a substituted or unsubstituted spirofluorenyl group, or a substituted or unsubstituted biphenyl group; $R^1$ to $R^4$ and $R^{11}$ to $R^{17}$ each independently represent hydrogen, an alkyl group having 1 to 10 carbon atoms, an unsubstituted phenyl group or a phenyl group having as a substituent at least one alkyl group having 1 to 10 carbon atoms, or an unsubstituted biphenyl group or a biphenyl group having as a substituent at least one alkyl group having 1 to 10 carbon atoms; $Ar^4$ represents an alkyl group having 1 to 10 carbon atoms, an unsubstituted phenyl group or a phenyl group having as a substituent at least one alkyl group having 1 to 10 carbon atoms, an unsubstituted biphenyl group or a biphenyl group having as a substituent at least one alkyl group having 1 to 10 carbon atoms, or an unsubstituted terphenyl group or a terphenyl group having as a substituent at least one alkyl group having 1 to 10 carbon atoms.

Another embodiment of the present invention is a light-emitting element including a light-emitting layer between a pair of electrodes. The light-emitting layer contains a first organic compound, a second organic compound, and a phosphorescent compound. The first organic compound is represented by a general formula (G3). The molecular weight of the first organic compound is greater than or equal to 500 and less than or equal to 2000. The second organic compound is a compound having an electron-transport property.

[Chemical formula 4]

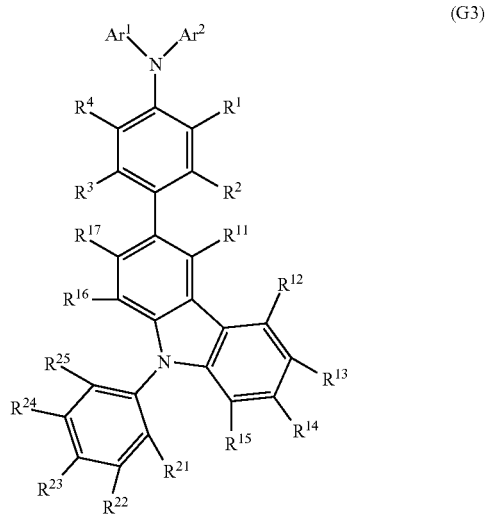
(G3)

In the general formula (G3), $Ar^1$ and $Ar^2$ each independently represent a substituted or unsubstituted fluorenyl group, a substituted or unsubstituted spirofluorenyl group, or a substituted or unsubstituted biphenyl group; $R^1$ to $R^4$, $R^{11}$ to $R^{17}$, and $R^{21}$ to $R^{25}$ each independently represent hydrogen, an alkyl group having 1 to 10 carbon atoms, an unsubstituted phenyl group or a phenyl group having as a substituent at least one alkyl group having 1 to 10 carbon atoms, or an unsubstituted biphenyl group or a biphenyl group having as a substituent at least one alkyl group having 1 to 10 carbon atoms.

In the above embodiments of the present invention, it is preferable that $Ar^1$ and $Ar^2$ in each of the general formulae (G0) to (G3) each independently represent a substituted or unsubstituted 2-fluorenyl group, a substituted or unsubstituted spiro-9,9'-bifluoren-2-yl group, or a biphenyl-4-yl group.

In the above embodiment of the present invention, it is preferable that a hole-transport layer be provided in contact with the light-emitting layer, the hole-transport layer contain a third organic compound, the third organic compound be represented by the general formula (G0), and the molecular weight of the third organic compound be greater than or equal to 500 and less than or equal to 2000.

[Chemical formula 5]

(G0)

In the general formula (G0), Ar¹ and Ar² each independently represent a substituted or unsubstituted fluorenyl group, a substituted or unsubstituted spirofluorenyl group, or a substituted or unsubstituted biphenyl group, and Ar³ represents a substituent including a carbazole skeleton.

In the above embodiment of the present invention, it is preferable that a hole-transport layer be provided in contact with the light-emitting layer, the hole-transport layer contain a third organic compound, the third organic compound be represented by the general formula (G1), and the molecular weight of the third organic compound be greater than or equal to 500 and less than or equal to 2000.

[Chemical formula 6]

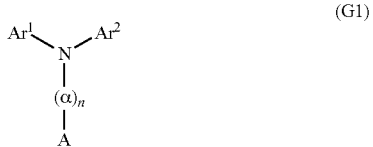

(G1)

In the general formula (G1), Ar¹ and Ar² each independently represent a substituted or unsubstituted fluorenyl group, a substituted or unsubstituted spirofluorenyl group, or a substituted or unsubstituted biphenyl group; α represents a substituted or unsubstituted phenylene group or a substituted or unsubstituted biphenyldiyl group; n represents 0 or 1; and A represents a substituted or unsubstituted 3-carbazolyl group.

In the above embodiment of the present invention, it is preferable that a hole-transport layer be provided in contact with the light-emitting layer, the hole-transport layer contain a third organic compound, the third organic compound be represented by the general formula (G2), and the molecular weight of the third organic compound be greater than or equal to 500 and less than or equal to 2000.

[Chemical formula 7]

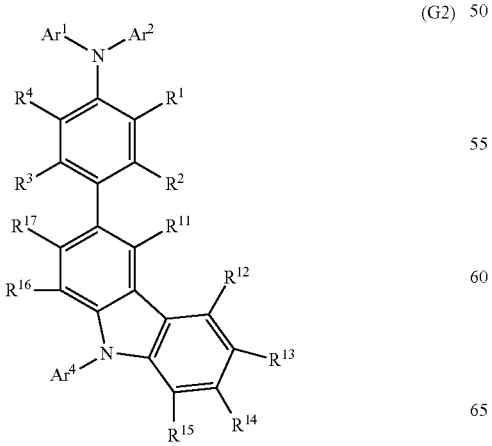

(G2)

In the general formula (G2), Ar¹ and Ar² each independently represent a substituted or unsubstituted fluorenyl group, a substituted or unsubstituted spirofluorenyl group, or a substituted or unsubstituted biphenyl group; $R^1$ to $R^4$ and $R^{11}$ to $R^{17}$ each independently represent hydrogen, an alkyl group having 1 to 10 carbon atoms, an unsubstituted phenyl group or a phenyl group having as a substituent at least one alkyl group having 1 to 10 carbon atoms, or an unsubstituted biphenyl group or a biphenyl group having as a substituent at least one alkyl group having 1 to 10 carbon atoms; $Ar^4$ represents an alkyl group having 1 to 10 carbon atoms, an unsubstituted phenyl group or a phenyl group having as a substituent at least one alkyl group having 1 to 10 carbon atoms, an unsubstituted biphenyl group or a biphenyl group having as a substituent at least one alkyl group having 1 to 10 carbon atoms, or an unsubstituted terphenyl group or a terphenyl group having as a substituent at least one alkyl group having 1 to 10 carbon atoms.

In the above embodiment of the present invention, it is preferable that a hole-transport layer be provided in contact with the light-emitting layer, the hole-transport layer contain a third organic compound, the third organic compound be represented by the general formula (G3), and the molecular weight of the third organic compound be greater than or equal to 500 and less than or equal to 2000.

[Chemical formula 8]

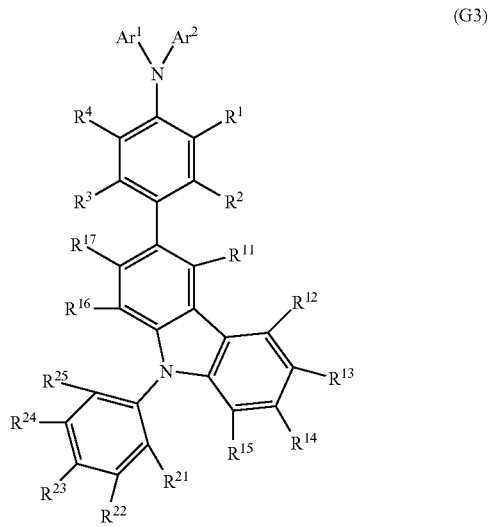

(G3)

In the general formula (G3), Ar¹ and Ar² each independently represent a substituted or unsubstituted fluorenyl group, a substituted or unsubstituted spirofluorenyl group, or a substituted or unsubstituted biphenyl group; $R^1$ to $R^4$, $R^{11}$ to $R^{17}$, and $R^{21}$ to $R^{25}$ each independently represent hydrogen, an alkyl group having 1 to 10 carbon atoms, an unsubstituted phenyl group or a phenyl group having as a substituent at least one alkyl group having 1 to 10 carbon atoms, or an unsubstituted biphenyl group or a biphenyl group having as a substituent at least one alkyl group having 1 to 10 carbon atoms.

In the above embodiments of the present invention, it is preferable that the third organic compound be identical to the first organic compound.

In the above embodiments of the present invention, it is preferable that a combination of the first organic compound and the second organic compound form an exciplex.

In the above embodiments of the present invention, it is preferable that the compound having the electron-transport property be a π-electron deficient heteroaromatic compound. Examples of the π-electron deficient heteroaromatic compound include compounds including a quinoxaline skeleton, a dibenzoquinoxaline skeleton, a quinoline skeleton, a pyrimidine skeleton, a pyrazine skeleton, a pyridine skeleton, a diazole skeleton, or a triazole skeleton.

Another embodiment of the present invention is a light-emitting device including the above-described light-emitting element in a light-emitting portion. Another embodiment of the present invention is an electronic device including the light-emitting device in a display portion. Another embodiment of the present invention is a lighting device including the light-emitting device in a light-emitting portion.

Since the light-emitting element in one embodiment of the present invention has a long lifetime, a light-emitting device having high reliability can be obtained. Similarly, an electronic device and a lighting device having high reliability can be obtained by employing one embodiment of the present invention.

In addition, since the light-emitting element in one embodiment of the present invention exhibits high emission efficiency in a high luminance region, a light-emitting device with high emission efficiency can be obtained. Similarly, an electronic device and a lighting device with high emission efficiency can be obtained by employing one embodiment of the present invention.

Note that the light-emitting device in this specification includes, in its category, an image display device with a light-emitting element. In addition, the light-emitting device includes all the following modules: a module in which a connector, such as an anisotropic conductive film or a tape carrier package (TCP), is attached to a light-emitting device; a module in which a printed wiring board is provided at the end of a TCP; and a module in which an integrated circuit (IC) is directly mounted on a light-emitting device by a chip-on-glass (COG) method. Furthermore, light-emitting devices that are used in lighting equipment and the like shall also be included.

One embodiment of the present invention can provide a light-emitting element having a long lifetime. By using the light-emitting element, a light-emitting device, an electronic device, and a lighting device each having high reliability can be provided. One embodiment of the present invention can also provide a light-emitting element exhibiting high emission efficiency in a high luminance region. By using the light-emitting element, a light-emitting device, an electronic device, and a lighting device each with high emission efficiency can be provided.

BRIEF DESCRIPTION OF DRAWINGS

FIGS. 5A to 5E each illustrate an example of an electronic device.

BEST MODE FOR CARRYING OUT THE INVENTION

Figure 1A:
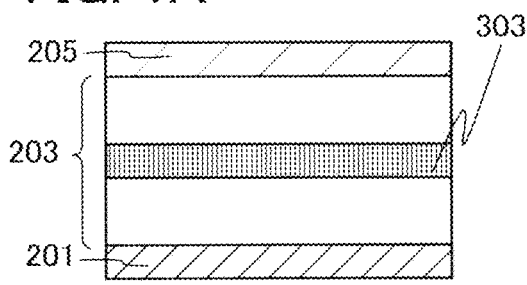
FIGS. 1A to 1F each illustrate an example of a light-emitting element in one embodiment of the present invention.

Embodiments will be described in detail with reference to the drawings. Note that the present invention is not limited to the following description, and it will be easily understood by those skilled in the art that various changes and modifications can be made without departing from the spirit and scope of the present invention. Therefore, the present invention should not be construed as being limited to the description in the following embodiments. Note that in the structures of the invention described below, the same portions or portions having similar functions are denoted by the same reference numerals in different drawings, and description of such portions is not repeated.

Embodiment 1

In this embodiment, light-emitting elements in one embodiment of the present invention will be described with reference to FIGS. 1A to 1F.

Light-emitting elements given in this embodiment as examples each include a pair of electrodes and a layer containing a light-emitting organic compound (EL layer) between the pair of electrodes.

A light-emitting element illustrated in FIG. 1A includes an EL layer 203 between a first electrode 201 and a second electrode 205. In this embodiment, the first electrode 201 serves as an anode, and the second electrode 205 serves as a cathode.

When a voltage higher than the threshold voltage of the light-emitting element is applied between the first electrode 201 and the second electrode 205, holes are injected to the EL layer 203 from the first electrode 201 side and electrons are injected to the EL layer 203 from the second electrode 205 side. The injected electrons and holes are recombined in the EL layer 203 and a light-emitting substance contained in the EL layer 203 emits light.

The EL layer 203 includes at least a light-emitting layer 303. In the light-emitting element in this embodiment, the light-emitting layer 303 contains a first organic compound, a second organic compound, and a phosphorescent compound.

In this embodiment, the phosphorescent compound is used as the light-emitting substance that is a guest material. One of the first and second organic compounds, the content of which is higher than that of the other in the light-emitting layer, is called a host material where the guest material is dispersed.

In the light-emitting layer of the light-emitting element in this embodiment, the content of the host material is higher than that of the guest material. When the guest material is dispersed in the host material, the crystallization of the light-emitting layer can be suppressed. Further, it is possible to suppress concentration quenching due to high concentration of the guest material, and thus the light-emitting element can have higher emission efficiency.

The first organic compound is a tertiary amine and has a structure in which two substituents including a fluorene skeleton, a spirofluorene skeleton, or a biphenylene skeleton and one substituent including a carbazole skeleton are each bonded to a nitrogen atom directly. The molecular weight of the first organic compound is greater than or equal to 500 and less than or equal to 2000. The second organic compound is a compound having an electron-transport property.

In the tertiary amine, a biphenyl group, a fluorenyl group, or a spirofluorenyl group is introduced as the substituent directly bonded to the nitrogen atom, instead of a phenyl group or an alkylphenyl group having a simple structure. Therefore, the tertiary amine is chemically stable, which enables a stable light-emitting element having a long lifetime to be easily obtained with high reproducibility. The tertiary amine also includes a carbazole skeleton and therefore has high thermal stability and improves reliability. The tertiary amine further includes a fluorenylamine skeleton, a spirofluorenylamine skeleton, or a biphenylamine skeleton, and therefore has a high hole-transport property and a high electron-blocking property. In addition, the tertiary amine has high triplet excitation energy compared with an amine including a naphthalene skeleton or the like, and therefore has an excellent exciton-blocking property. Accordingly, leakage of electrons or diffusion of excitons can be prevented even in a high luminance region, and thus the light-emitting element can exhibit high emission efficiency.

Materials which can be used as the first organic compound, the second organic compound, and the phosphorescent compound contained in the light-emitting layer 303 will be described in detail below.

<First Organic Compound>

The first organic compound is represented by the general formula (G0), and the molecular weight of the first organic compound is greater than or equal to 500 and less than or equal to 2000.

[Chemical formula 9]

In the general formula (G0), $Ar^1$ and $Ar^2$ each independently represent a substituted or unsubstituted fluorenyl group, a substituted or unsubstituted spirofluorenyl group, or a substituted or unsubstituted biphenyl group, and $Ar^3$ represents a substituent including a carbazole skeleton.

In the case where the fluorenyl group, the spirofluorenyl group, or the biphenyl group has a substituent in the general formula (G0), examples of the substituent include an alkyl group having 1 to 10 carbon atoms, an unsubstituted phenyl group or a phenyl group having as a substituent at least one alkyl group having 1 to 10 carbon atoms, an unsubstituted biphenyl group or a biphenyl group having as a substituent at least one alkyl group having 1 to 10 carbon atoms, and an unsubstituted terphenyl group or a terphenyl group having as a substituent at least one alkyl group having 1 to 10 carbon atoms. The compound represented by the general formula (G0) and having any of these substituents is less likely to have low hole-transport, electron-blocking, and exciton-blocking properties than (or can have hole-transport, electron-blocking, and exciton-blocking properties as high as) a compound not having the substituent.

Examples of Ar³ include a substituted or unsubstituted (9H-carbazol-9-yl)phenyl group, a substituted or unsubstituted (9H-carbazol-9-yl)biphenyl group, a substituted or unsubstituted (9H-carbazol-9-yl)terphenyl group, a substituted or unsubstituted (9-aryl-9H-carbazol-3-yl)phenyl group, a substituted or unsubstituted (9-aryl-9H-carbazol-3-yl)biphenyl group, a substituted or unsubstituted (9-aryl-9H-carbazol-3-yl)terphenyl group, a substituted or unsubstituted 9-aryl-9H-carbazol-3-yl group, and the like. Specific examples of aryl groups include an unsubstituted phenyl group or a phenyl group having as a substituent at least one alkyl group having 1 to 10 carbon atoms, an unsubstituted biphenyl group or a biphenyl group having as a substituent at least one alkyl group having 1 to 10 carbon atoms, an unsubstituted terphenyl group or a terphenyl group having as a substituent at least one alkyl group having 1 to 10 carbon atoms, and the like. Note that in the case where Ar³ has a substituent, examples of the substituent include an alkyl group having 1 to 10 carbon atoms, an unsubstituted phenyl group or a phenyl group having as a substituent at least one alkyl group having 1 to 10 carbon atoms, an unsubstituted biphenyl group or a biphenyl group having as a substituent at least one alkyl group having 1 to 10 carbon atoms, an unsubstituted terphenyl group or a terphenyl group having as a substituent at least one alkyl group having 1 to 10 carbon atoms, and the like. Each of these substituents can suppress the impairment of the high hole-transport, electron-blocking, and exciton-blocking properties of the compound represented by the general formula (G0).

It is preferable that the first organic compound contained in the light-emitting layer 303 be represented by the following general formula (G1).

[Chemical formula 10]

(G1)

In the general formula (G1), Ar¹ and Ar² each independently represent a substituted or unsubstituted fluorenyl group, a substituted or unsubstituted spirofluorenyl group, or a substituted or unsubstituted biphenyl group; α represents a substituted or unsubstituted phenylene group or a substituted or unsubstituted biphenyldiyl group; n represents 0 or 1; and A represents a substituted or unsubstituted 3-carbazolyl group.

Examples of specific structures of a in the general formula (G1) are shown by structural formulae (1-1) to (1-9).

[Chemical formula 11]

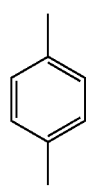

(1-1)

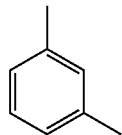

(1-2)

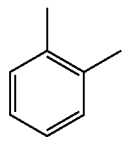

(1-3)

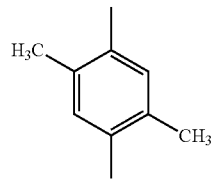

(1-4)

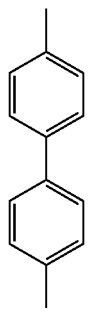

(1-5)

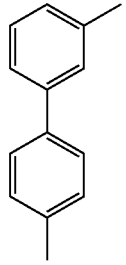

(1-6)

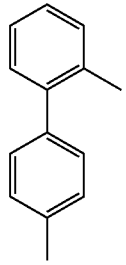

(1-7)

(1-8)

(1-9)

It is further preferable that the first organic compound contained in the light-emitting layer 303 be represented by the following general formula (G2).

[Chemical formula 12]

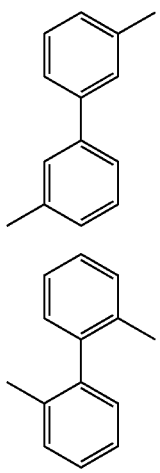

(G2)

In the general formula (G2), $Ar^1$ and $Ar^2$ each independently represent a substituted or unsubstituted fluorenyl group, a substituted or unsubstituted spirofluorenyl group, or a substituted or unsubstituted biphenyl group; $R^1$ to $R^4$ and $R^{11}$ to $R^{17}$ each independently represent hydrogen, an alkyl group having 1 to 10 carbon atoms, an unsubstituted phenyl group or a phenyl group having as a substituent at least one alkyl group having 1 to 10 carbon atoms, or an unsubstituted biphenyl group or a biphenyl group having as a substituent at least one alkyl group having 1 to 10 carbon atoms; $Ar^4$ represents an alkyl group having 1 to 10 carbon atoms, an unsubstituted phenyl group or a phenyl group having as a substituent at least one alkyl group having 1 to 10 carbon atoms, an unsubstituted biphenyl group or a biphenyl group having as a substituent at least one alkyl group having 1 to 10 carbon atoms, or an unsubstituted terphenyl group or a terphenyl group having as a substituent at least one alkyl group having 1 to 10 carbon atoms.

It is particularly preferable that the first organic compound contained in the light-emitting layer 303 be represented by the following general formula (G3).

[Chemical formula 13]

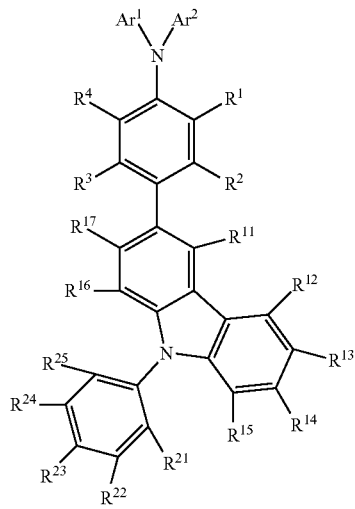

(G3)

In the general formula (G3), $Ar^1$ and $Ar^2$ each independently represent a substituted or unsubstituted fluorenyl group, a substituted or unsubstituted spirofluorenyl group, or a substituted or unsubstituted biphenyl group; $R^1$ to $R^4$, $R^{11}$ to $R^{17}$, and $R^{21}$ to $R^{25}$ each independently represent hydrogen, an alkyl group having 1 to 10 carbon atoms, an unsubstituted phenyl group or a phenyl group having as a substituent at least one alkyl group having 1 to 10 carbon atoms, or an unsubstituted biphenyl group or a biphenyl group having as a substituent at least one alkyl group having 1 to 10 carbon atoms.

It is preferable that $Ar^1$ and $Ar^2$ each independently represent a substituted or unsubstituted 2-fluorenyl group, a substituted or unsubstituted spiro-9,9'-bifluoren-2-yl group, or a biphenyl-4-yl group. A tertiary amine including any of these skeletons is preferable because of its high hole-transport and electron-blocking properties, and its excellent exciton-blocking property due to its triplet excitation energy higher than that of an amine including a naphthalene skeleton or the like. Among biphenyl groups, fluorenyl groups, and spirofluorenyl groups, the ones with these sites of substitution are preferable because they are easy to synthesize and are inexpensiveness.

Examples of specific structures of $R^1$ to $R^4$, $R^{11}$ to $R^{17}$, and $R^{21}$ to $R^{25}$ in the general formulae (G2) and (G3) are shown by structural formulae (2-1) to (2-17). In the case where the fluorenyl group, the spirofluorenyl group, or the biphenyl group has a substituent in each of the above general formulae, examples of the substituent include an alkyl group having 1 to 10 carbon atoms, an unsubstituted phenyl group or a phenyl group having as a substituent at least one alkyl group having 1 to 10 carbon atoms, and an unsubstituted biphenyl group or a biphenyl group having as a substituent at least one alkyl group having 1 to 10 carbon atoms. As examples of specific structures of these, the substituents represented by the structural formulae (2-2) to (2-17) can be given. Examples of specific structures of $Ar^4$ in the general formula (G2) include substituents represented by the structural formulae (2-2) to (2-17).

[Chemical formula 14]

(2-1)

(2-2) 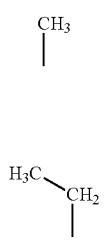
(2-3) 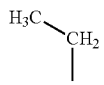
(2-4) 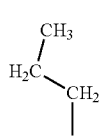
(2-5) 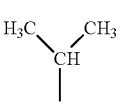
(2-6) 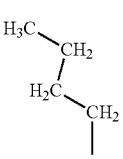
(2-7) 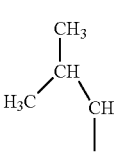
(2-8) 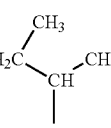
(2-9) 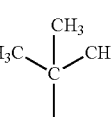
(2-10) 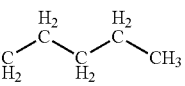
(2-11) 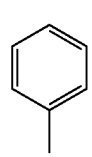
(2-12) 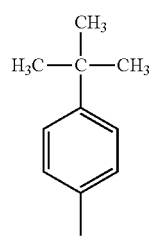
(2-13) 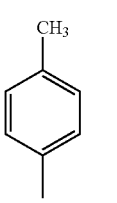
(2-14) 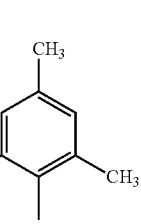
(2-15) 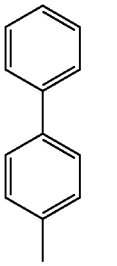
(2-16) 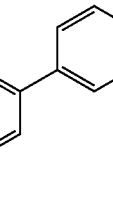
(2-17) 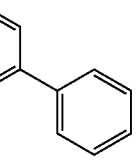
Specific examples of the organic compound represented by the general formulae (G0) include organic compounds represented by structural formulae (101) to (142). Note that the present invention is not limited to these examples.

[Chemical formula 15]
(101)
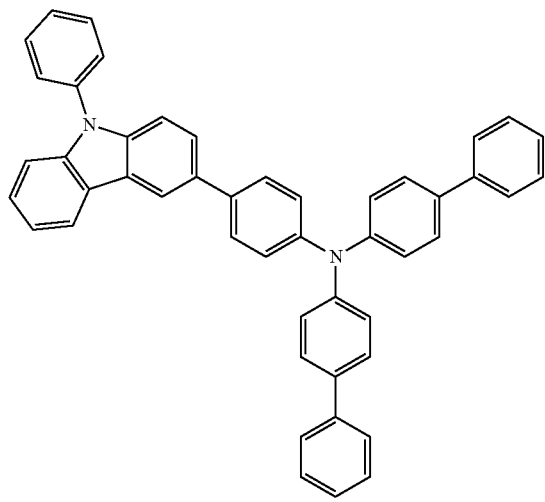
(102)
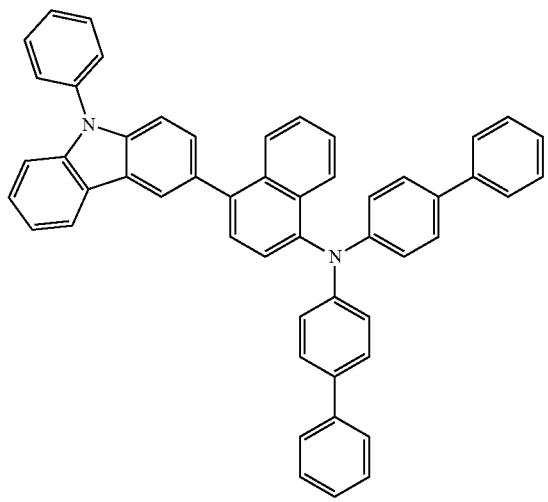
(103)
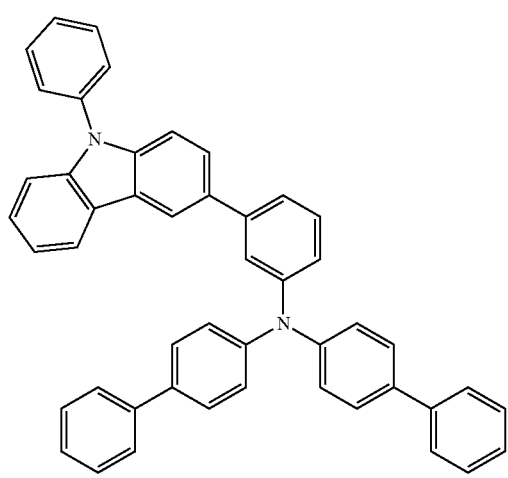
(104)
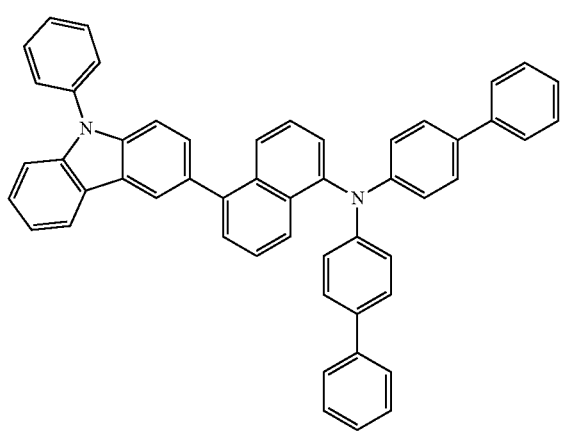
(105)
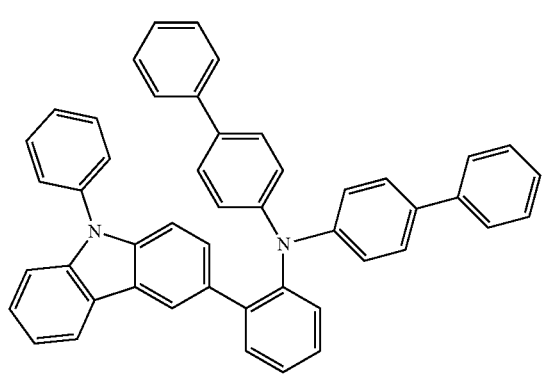
(106)
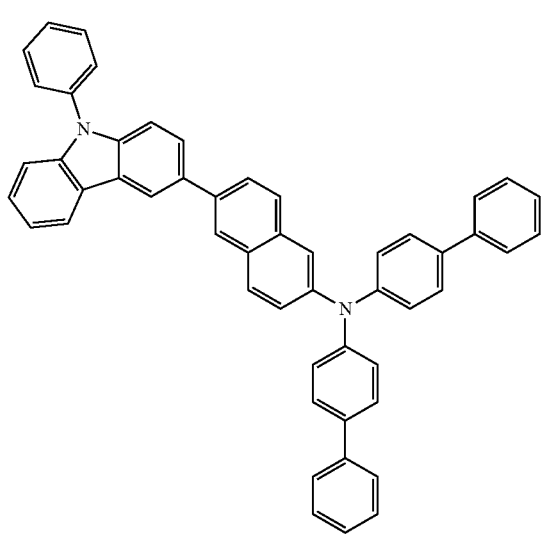

[Chemical formula 16]
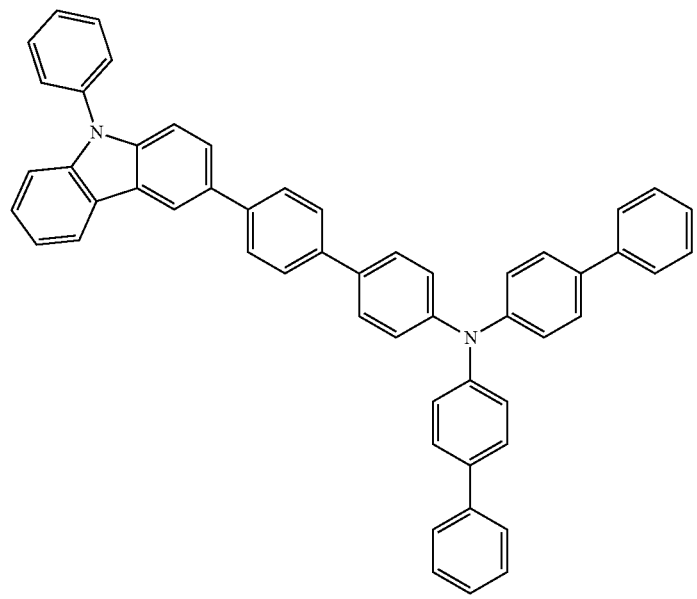
(107)
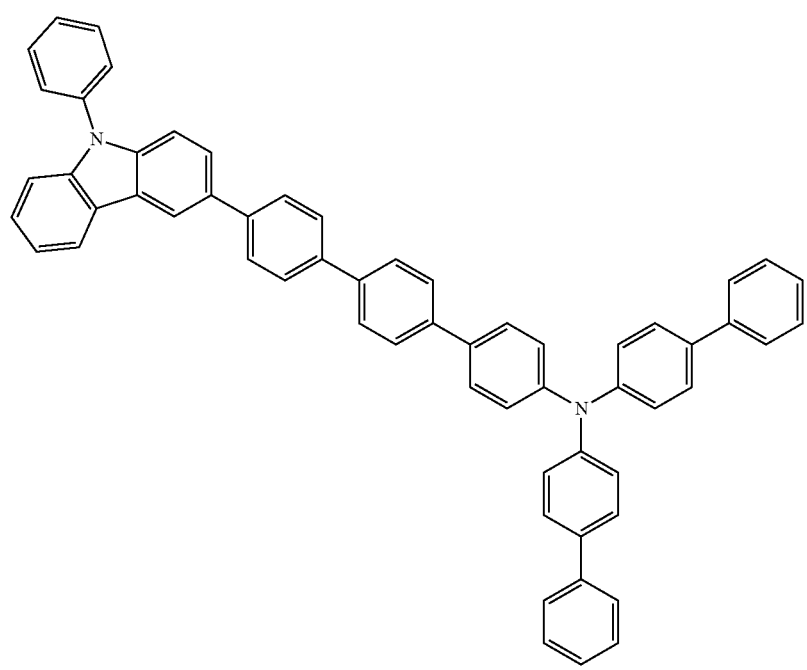
(108)

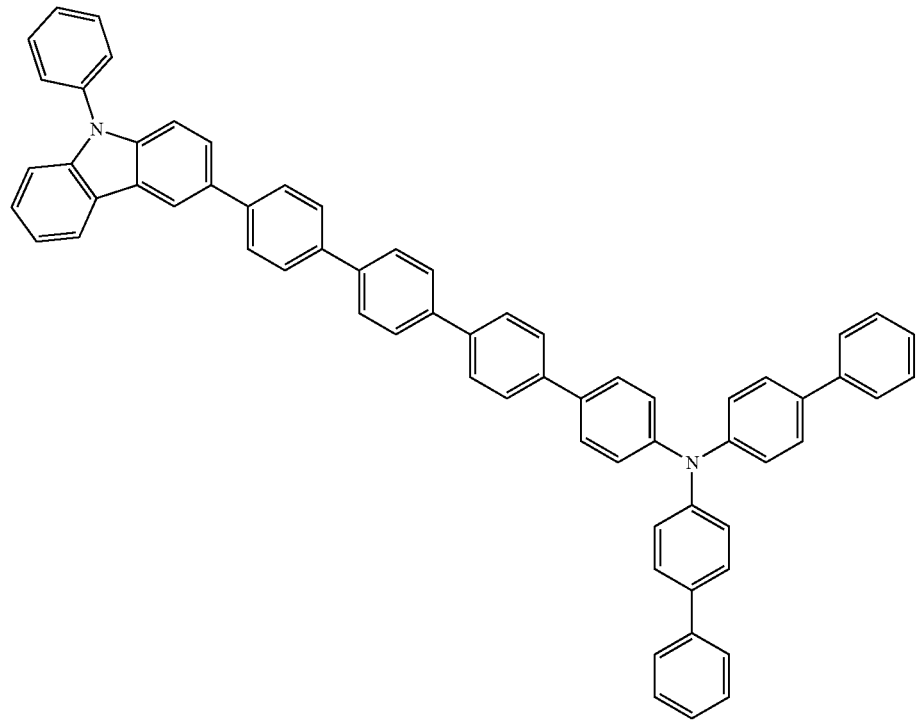
(109)
[Chemical formula 17]
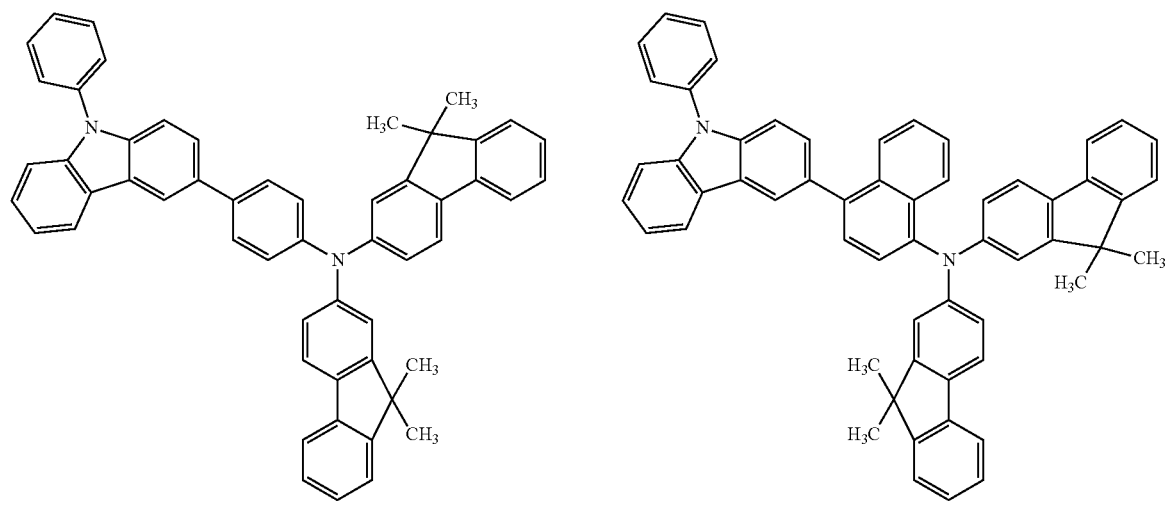
(110) (111)

-continued
(112)
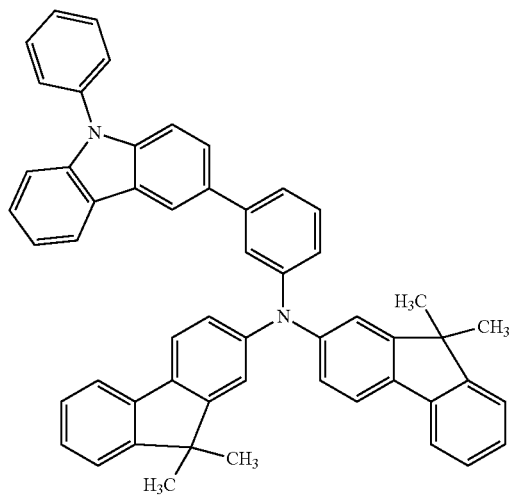
(113)
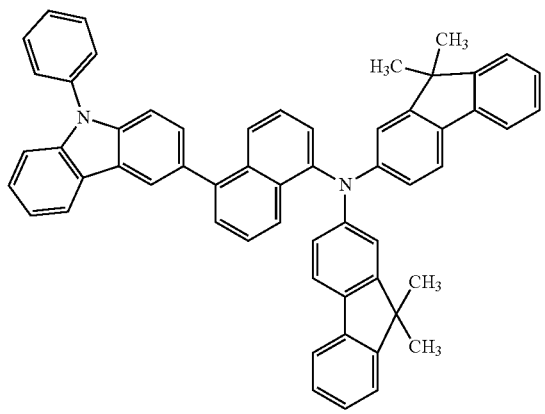
(114)
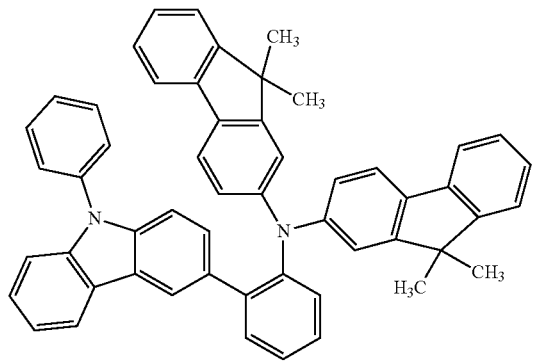
(115)
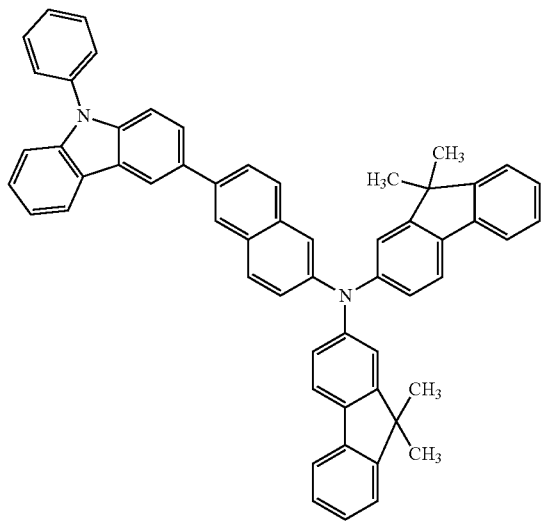

[Chemical formula 18]
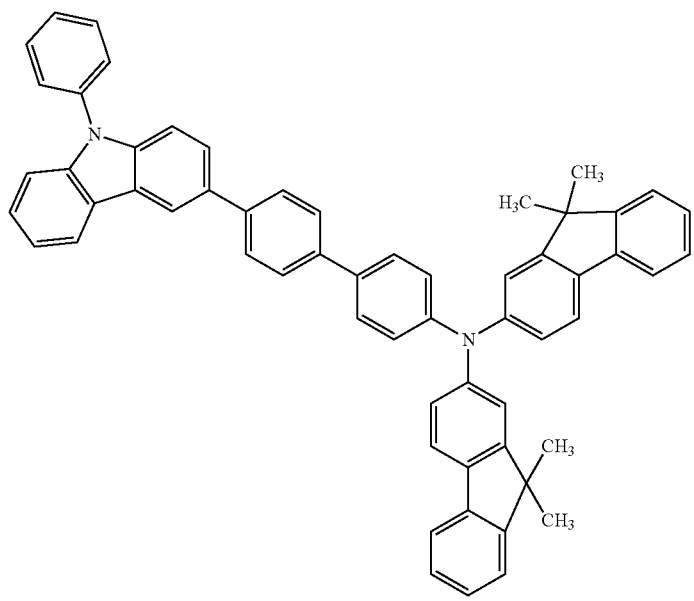
(116)
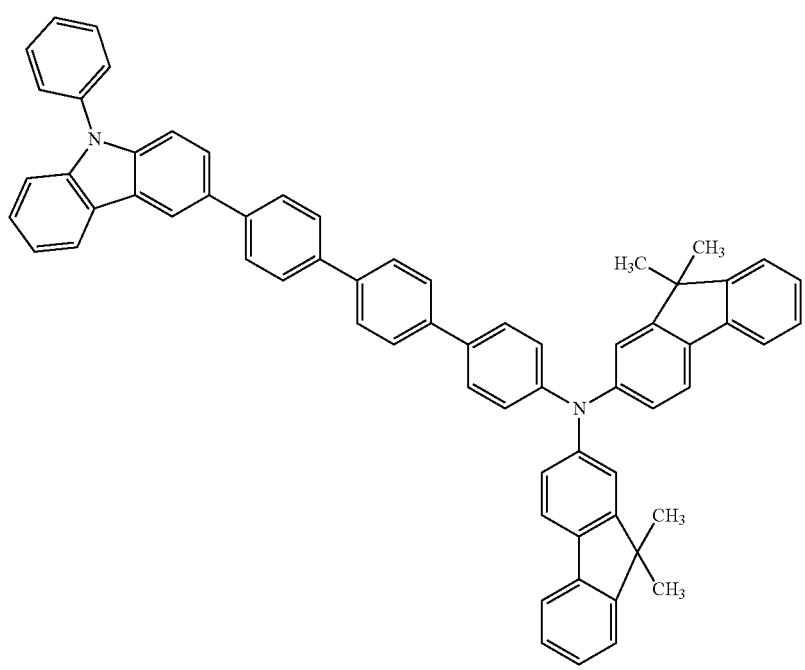
(117)

(118)
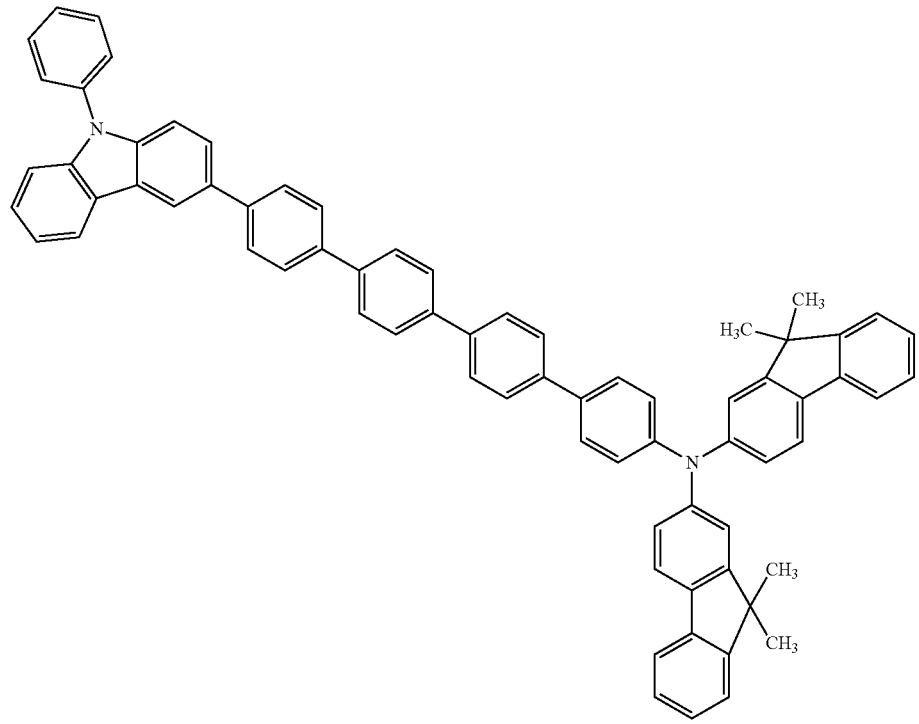
[Chemical formula 19]
(119)
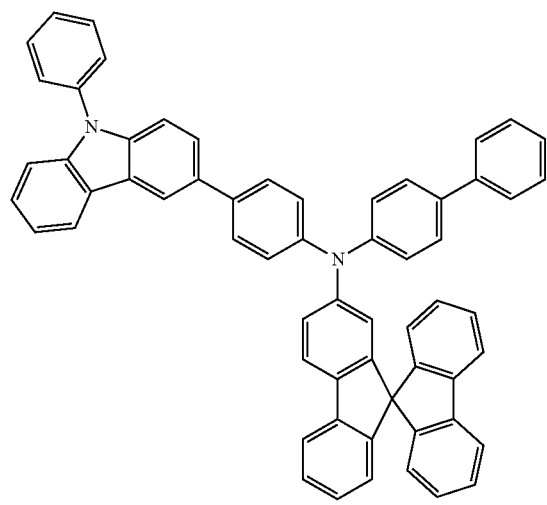
(120)
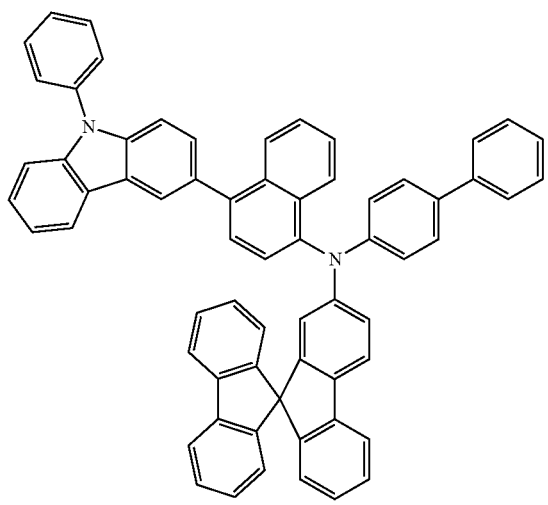

-continued
(121)
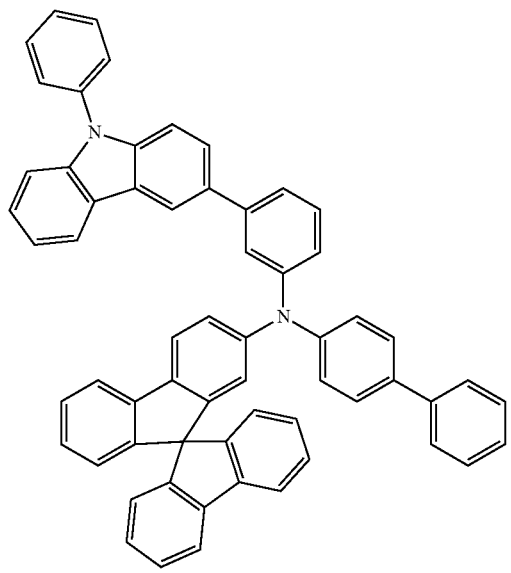
(122)
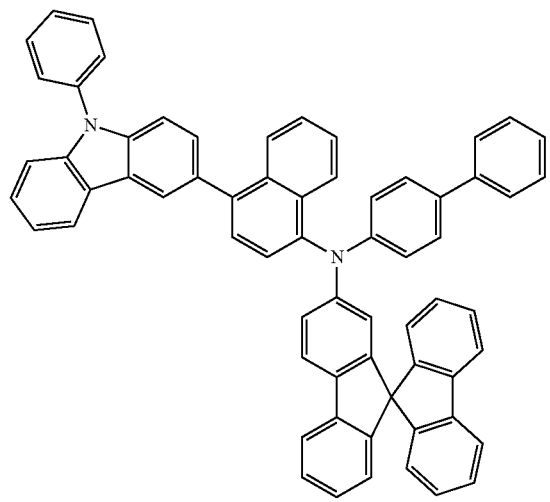
(123)
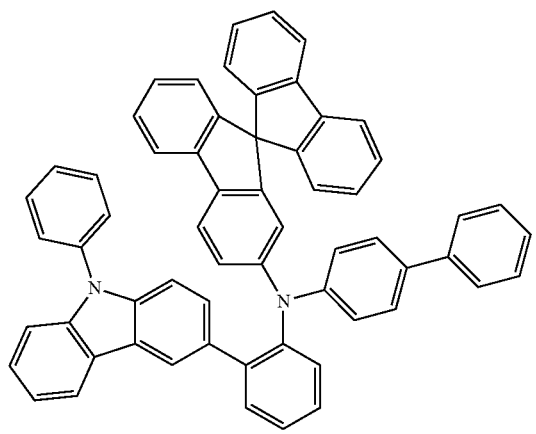
(124)
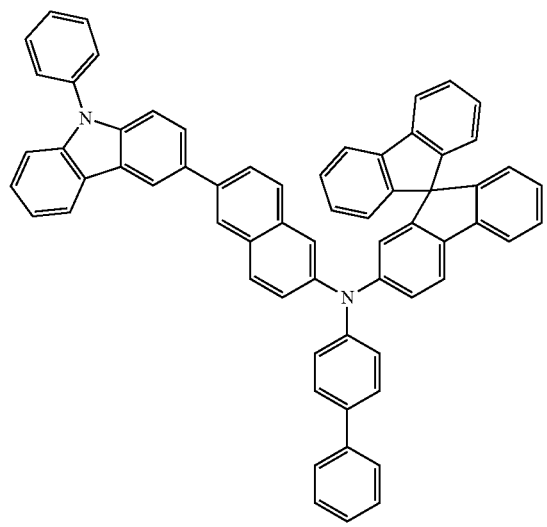

[Chemical formula 20]
(125)
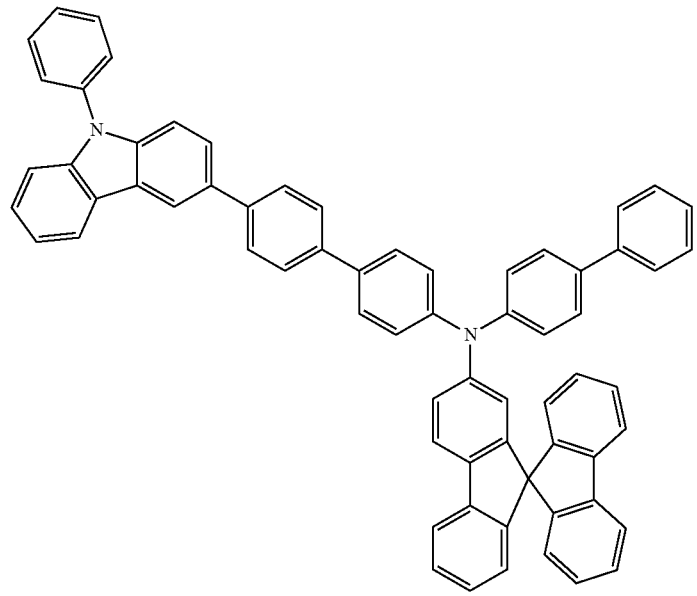
(126)
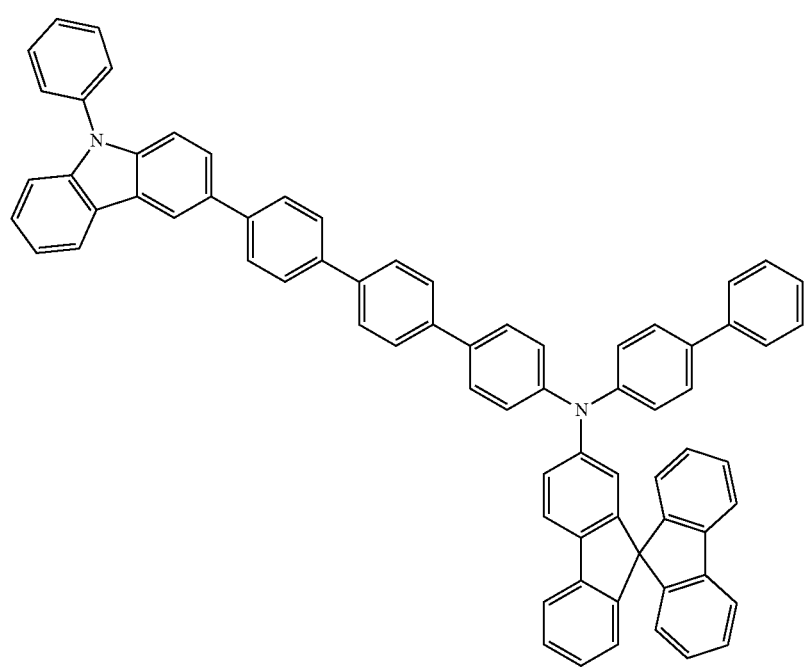

(127)
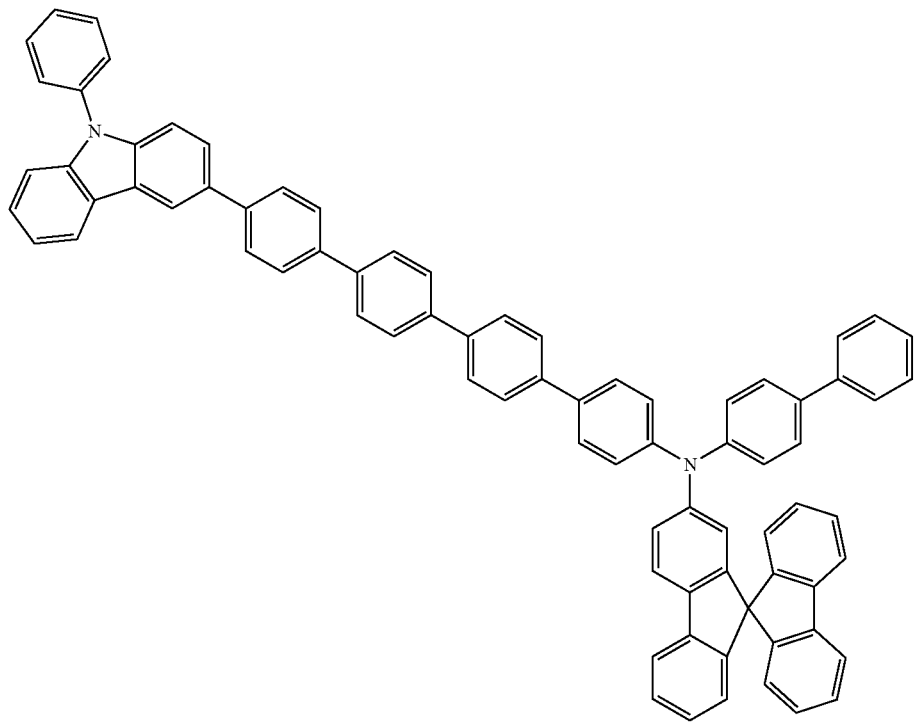
[Chemical formula 21]
(128)
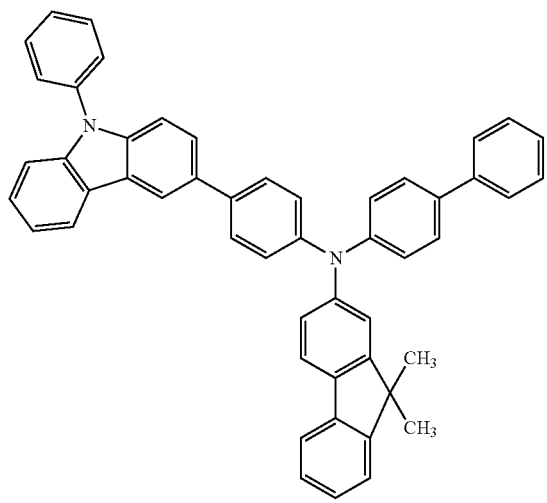
(129)
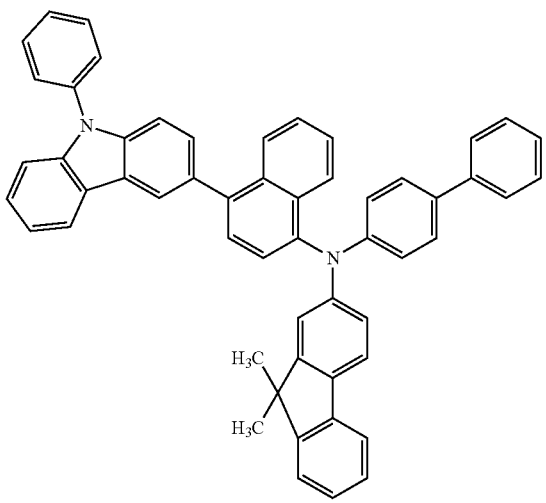

-continued
(130)
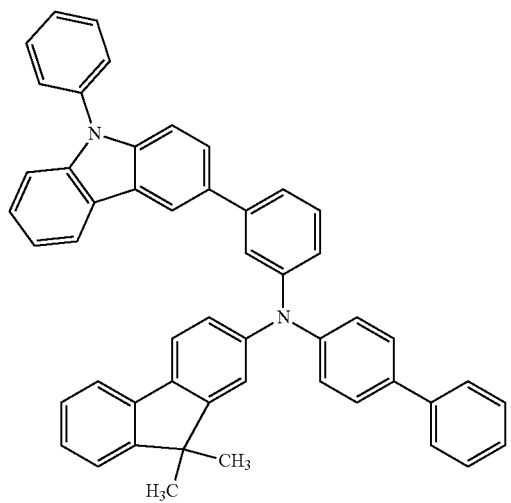
(131)
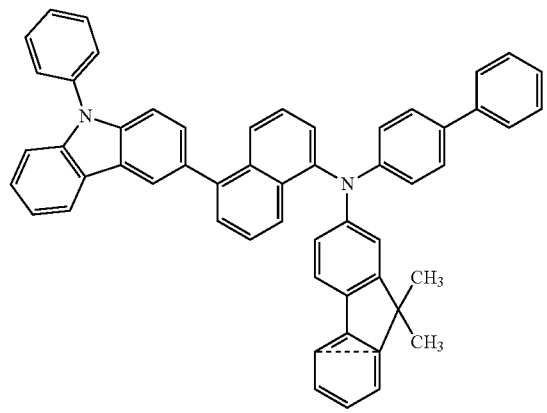
(132)
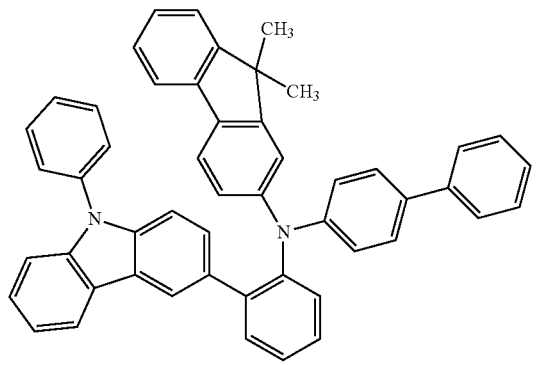
(133)
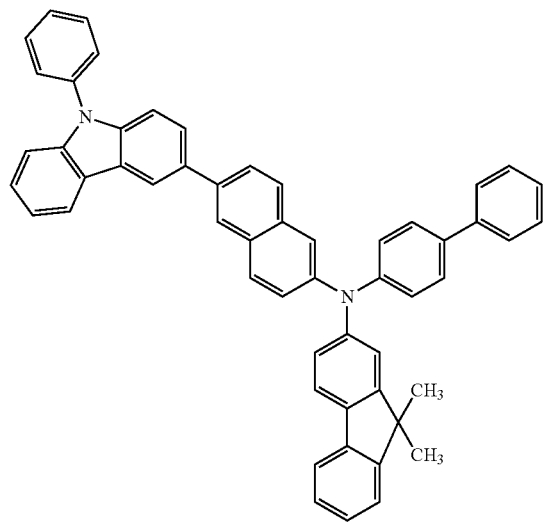

[Chemical formula 22]
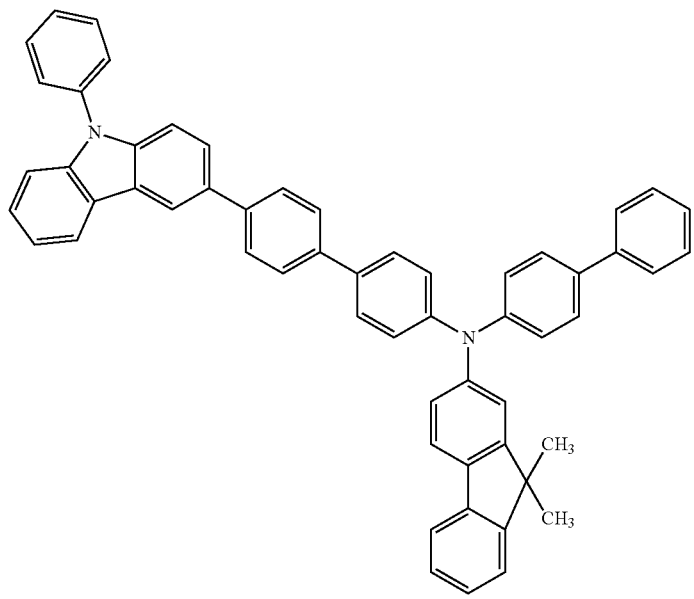
(134)
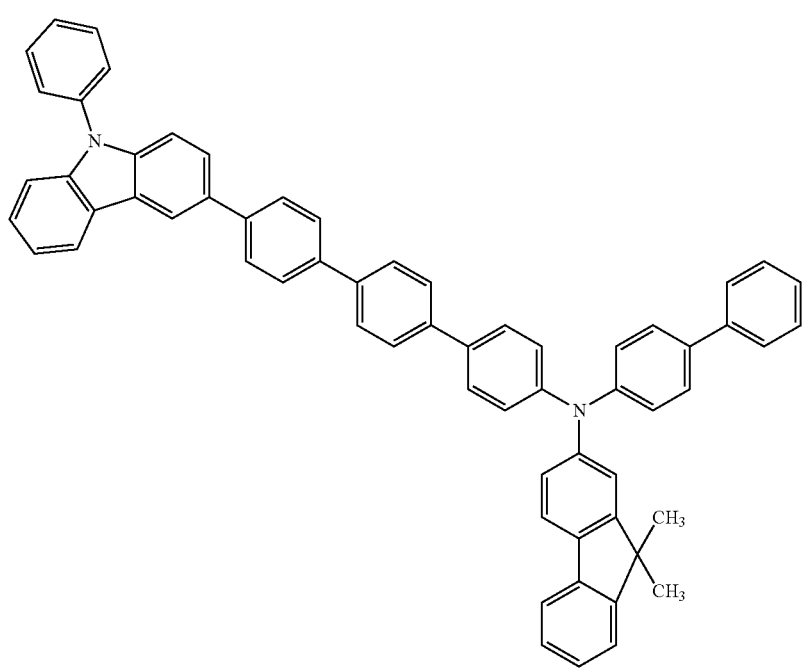
(135)

(136)
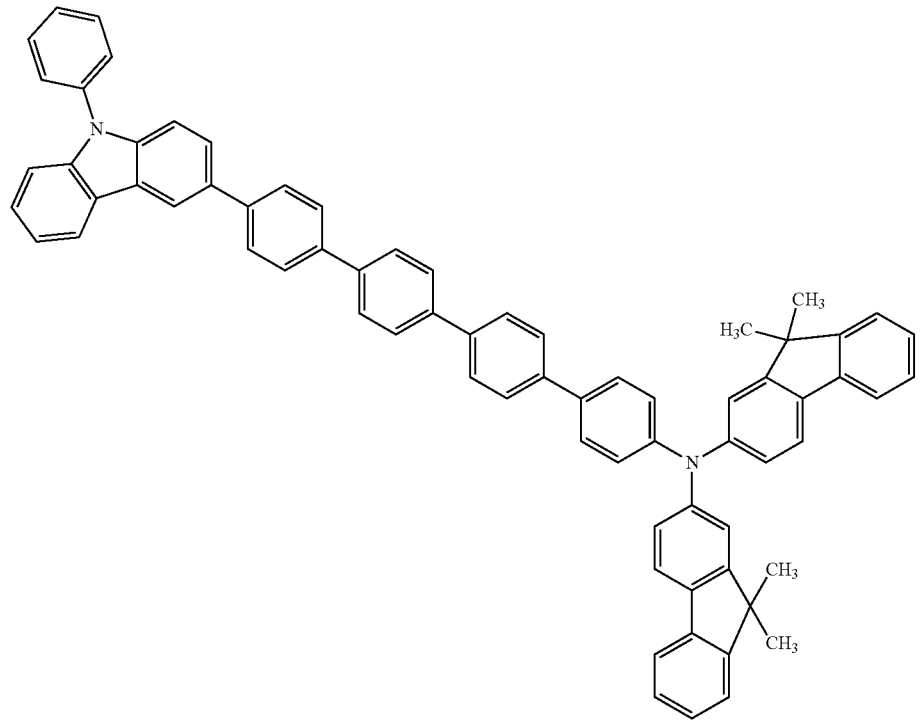
[Chemical formula 23]
(137)
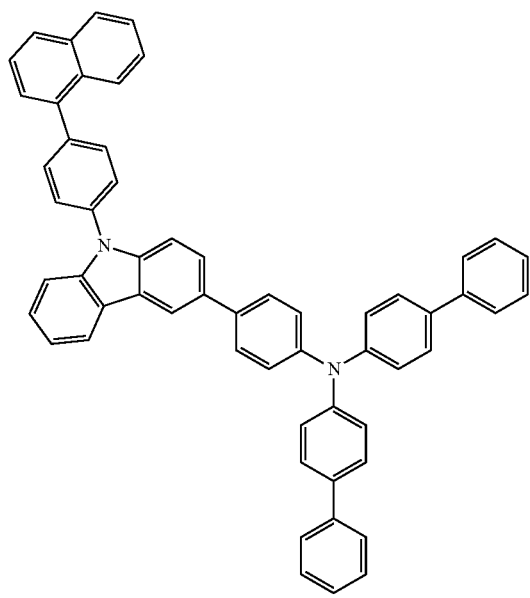
(138)
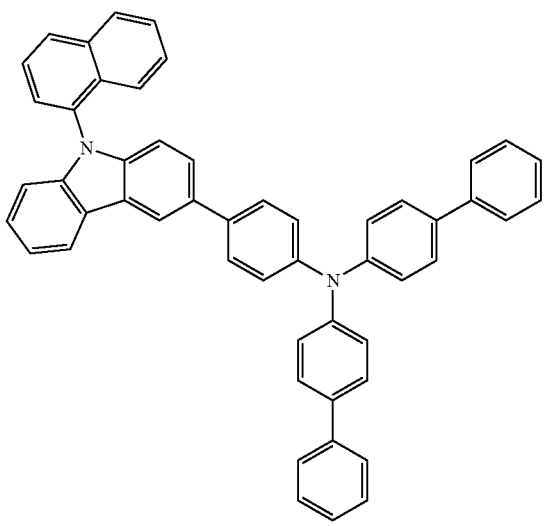

-continued (139)

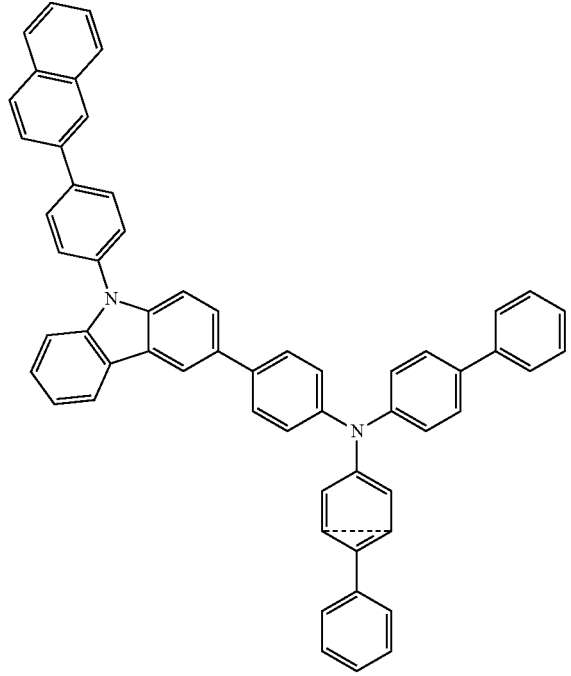

(140)

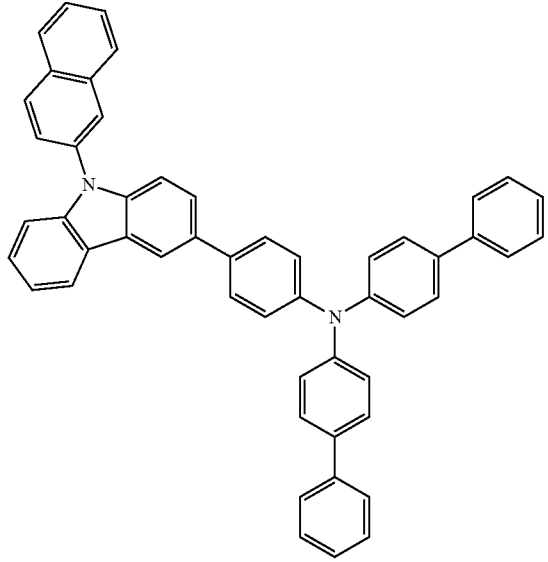

(141)

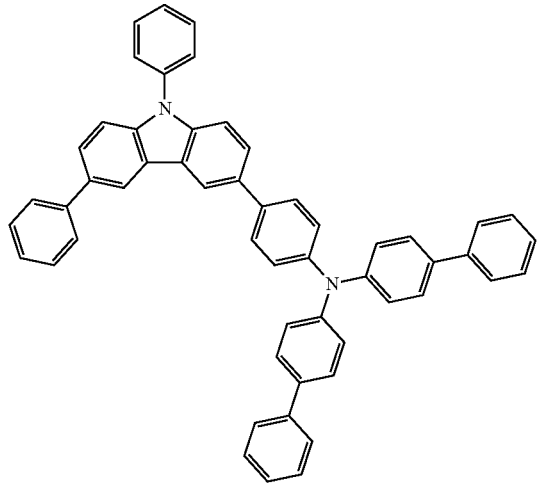

(142)

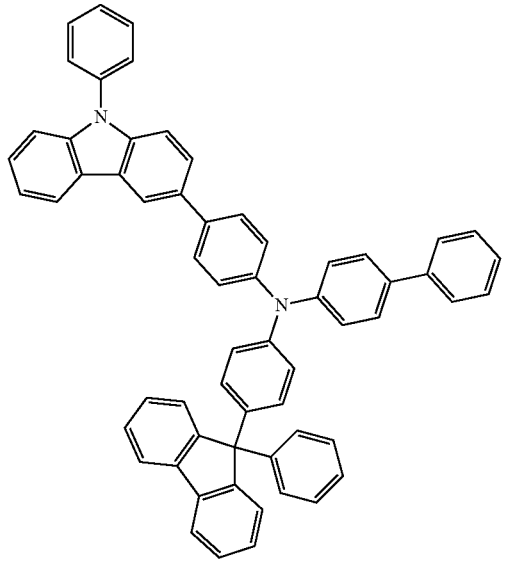

<Second Organic Compound>

The second organic compound is a compound having an electron-transport property. As the compound having the electron-transport property, a π-electron deficient heteroaromatic compound such as a nitrogen-containing heteroaromatic compound, a metal complex having a quinoline skeleton or a benzoquinoline skeleton, a metal complex having an oxazole-based or thiazole-based ligand, or the like can be used.

Specific examples include the following: metal complexes such as bis(10-hydroxybenzo[h]quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: Zn(BOX)$_2$), and bis[2-(2-benzothiazolyl)phenolato]zinc(II) (abbreviation: Zn(BTZ)$_2$); heterocyclic compounds having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2', 2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a quinoxaline skeleton or a dibenzoquinoxaline skeleton, such as 2-[3-(dibenzothiophen-4-yl)phenyl]dibenzo[f,h]quinoxaline (abbreviation: 2mDBTPDBq-II), 7-[3-(dibenzothiophen-4-yl)phenyl]dibenzo [f, h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), 2-[3'-(dibenzothiophen-4-yl)biphenyl-3-yl]dibenzo[f,h]quinoxaline (abbreviation: 2mDBTBPDBq-II), and 2-[3'-(9H-carbazol-9-yl)biphenyl-3-yl]dibenzo[f,h]quinoxaline (abbreviation: 2mCzBPDBq); heterocyclic compounds having a diazine skeleton (a pyrimidine skeleton or a pyrazine skeleton), such as 4,6-bis[3-(phenanthren-9-yl)phenyl]pyrimidine (abbreviation: 4,6mPnP2Pm), 4,6-bis[3-(9H-carbazol-9-yl)phenyl]pyrimidine (abbreviation: 4,6mCzP2Pm), and 4,6-bis[3-(4-dibenzothienyl)phenyl]pyrimidine (abbreviation: 4,6mDBTP2Pm-II); heterocyclic compounds having a pyridine skeleton, such as 3,5-bis[3-(9H-carbazol-9-yl)phenyl]pyridine (abbreviation: 35DCzPPy), 1,3,5-tri[3-(3-pyridyl)phenyl]benzene (abbreviation: TmPyPB), and 3,3',5,5'-tetra[(m-pyridyl)-phen-3-yl]biphenyl (abbreviation: BP4mPy). Among the above materials, heterocyclic compounds having a quinoxaline skeleton or a dibenzoquinoxaline skeleton, heterocyclic compounds having a diazine skeleton, and heterocyclic compounds having a pyridine skeleton are preferable because of their high reliability.

<Phosphorescent Compound>

Examples of phosphorescent compounds which can be used for the light-emitting layer 303 are given here. Examples of phosphorescent compounds having an emission peak at 440 nm to 520 nm include the following: organometallic iridium complexes having a 4H-triazole skeleton, such as tris{2-[5-(2-methylphenyl)-4-(2,6-dimethylphenyl)-4H-1,2,4-triazol-3-yl-κN²]phenyl-κC}iridium (III) (abbreviation: [Ir(mpptz-dmp)$_3$]), tris(5-methyl-3,4-diphenyl-4H-1,2,4-triazolato)iridium(M) (abbreviation: [Ir(Mptz)$_3$], and tris[4-(3-biphenyl)-5-isopropyl-3-phenyl-4H-1,2,4-triazolato]iridium(III) (abbreviation: [Ir(iPrptz-3b)$_3$]); organometallic iridium complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic iridium complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenOypyridinato-N,C²']iridium(III) tetrakis(1-pyrazolyl)borate (abbreviation: FIr6), bis[2-(4',6'-difluorophenOypyridinato-N,C²']iridium(III) picolinate (abbreviation: FIrpic), bis{2-[3',5'-bis(trifluoromethyl)phenyl]pyridinato-N,C²'}iridium(III) picolinate (abbreviation: [Ir(CF$_3$ppy)$_2$(pic)]), and bis[2-(4',6'-difluorophenOypyridiriato-N,C²']iridium(III) acetylacetonate (abbreviation: FIr(acac)). Among the above materials, the organometallic iridium complexes having a 4H-triazole skeleton are particularly preferable because of their high reliability and high emission efficiency.

Examples of phosphorescent compounds having an emission peak at 520 nm to 600 nm include the following: organometallic iridium complexes having a pyrimidine skeleton, such as tris(4-methyl-6-phenylpyrimidinato)iridium (III) (abbreviation: [Ir(mppm)$_3$]), tris(4-t-butyl-6-phenylpyrimidinato)iridium(III) (abbreviation: [Ir(tB uppm)$_3$]), (acetylacetonato)bis(6-methyl-4-phenylpyrimidinato) iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[4-(2-norbornyl)-6-phenylpyrimidinato]iridium (III) (endo- and exo-mixture) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium (III) (abbreviation: [Ir(dppm)$_2$(acac)]); organometallic iridium complexes having a pyrazine skeleton, such as (acetylacetonato)bis(3,5-dimethyl-2-phenylpyrazinato) iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,C²')iridium(III) (abbreviation: [Ir(ppy)$_3$]), bis(2-phenylpyridinato-N,C²')iridium (III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,C²') iridium(III) (abbreviation: [Ir(pq)$_3$]), and bis(2-phenylquinolinato-N,C²')iridium(III) acetylacetonate (abbreviation: [Ir(pq)$_2$(acac)]); and rare earth metal complexes such as tris(acetylacetonato)(monophenanthroline) terbium(III) (abbreviation: [Tb(acac)$_3$(Phen)]). Among the above materials, the organometallic iridium complexes having a pyrimidine skeleton are particularly preferable because of their distinctively high reliability and emission efficiency.

Examples of phosphorescent compounds having an emission peak at 600 nm to 700 nm include the following: organometallic iridium complexes having a pyrimidine skeleton, such as bis[4,6-bis(3-methylphenyl)pyrimidinato](diisobutyrylmethano)iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(dlnpm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato] iridium(III) (abbreviation: [Ir(Fdpq)$_2$(acac)]); organometallic iridium complexes having a pyridine skeleton, such as tris(1-phenylisoquinolinato-N,C²')iridium(III) (abbreviation: [Ir(piq)$_3$]) and bis(1-phenylisoquinolinato-N,C²') iridium(III) acetylacetonate (abbreviation: [Ir(piq)$_2$(acac)]); platinum complexes such as 2,3,7,8,12,13,17,18-octaethyl-21H,23H-porphyrin platinum(II) (abbreviation: PtOEP); and rare earth metal complexes such as tris(1,3-diphenyl-1,3-propanedionato)(monophenanthroline)europium(III) (abbreviation: [Eu(DBM)$_3$(Phen)]) and tris[1-(2-thenoyl)-3,3,3-trifluoroacetonato](monophenanthroline)europium(III) (abbreviation: [Eu(TTA)$_3$(Phen)]). Among the above materials, the organometallic iridium complexes having a pyrimidine skeleton are particularly preferable because of their distinctively high reliability and emission efficiency. Further, the organometallic iridium complexes having a pyrazine skeleton can provide red light emission with favorable chromaticity.

With the use of the above-described light-emitting layer containing the first organic compound, the second organic compound, and the phosphorescent compound, a light-emitting element having a long lifetime can be manufactured. In addition, with the use of the light-emitting layer, a light-emitting element exhibiting high emission efficiency in a high luminance region can be manufactured.

Further, by providing a plurality of light-emitting layers and making emission colors of the light-emitting layers different, light emission of a desired color can be obtained from the light-emitting element as a whole. For example, the emission colors of first and second light-emitting layers are complementary in a light-emitting element having the two light-emitting layers, so that the light-emitting element can be made to emit white light as a whole. Note that the term "complementary" means color relationship in which an achromatic color is obtained when colors are mixed. That is, emission of white light can be obtained by mixture of light emitted from substances whose emission colors are complementary colors. Further, the same applies to a light-emitting element having three or more light-emitting layers. Note that in a light-emitting element including a plurality of light-emitting layers in one embodiment of the present invention, at least one of the light-emitting layers has the above-described composition (containing the first organic compound, the second organic compound, and the phosphorescent compound), and all the light-emitting layers may have the above composition.

In addition to the light-emitting layer, the EL layer 203 may further include one or more layers containing any of a substance with a high hole-injection property, a substance with a high hole-transport property, a hole-blocking material, a substance with a high electron-transport property, a substance with a high electron-injection property, a substance with a bipolar property (a substance with high electron- and hole-transport properties), and the like. A known material can be used for the EL layer 203. Either a low molecular compound or a high molecular compound can be used, and an inorganic compound may also be used.

Figure 1B:
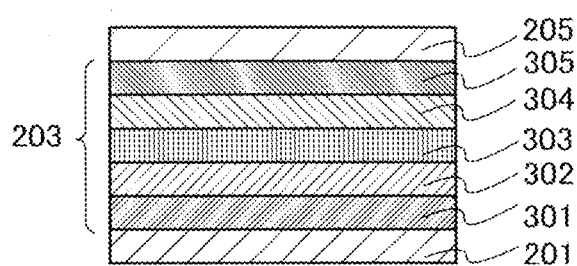

A light-emitting element illustrated in FIG. 1B includes the EL layer 203 between the first electrode 201 and the second electrode 205, and in the EL layer 203, a hole-injection layer 301, a hole-transport layer 302, a light-emitting layer 303, an electron-transport layer 304, and an electron-injection layer 305 are stacked in this order from the first electrode 201 side.

Figure 1C:
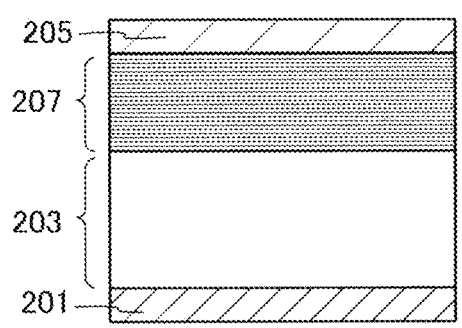

A light-emitting element illustrated in FIG. 1C includes the EL layer 203 between the first electrode 201 and the second electrode 205, and further includes an intermediate layer 207 between the EL layer 203 and the second electrode 205.

Figure 1D:
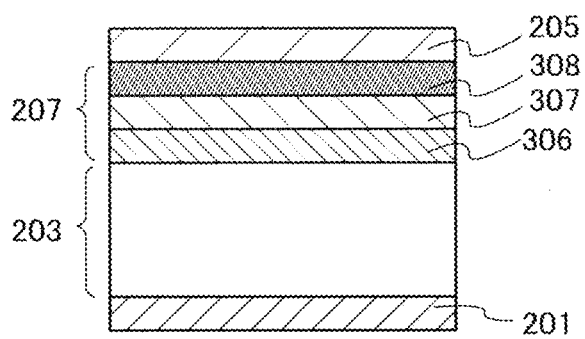

A specific example of a structure of the intermediate layer 207 is illustrated in FIG. 1D. The intermediate layer 207 includes at least a charge-generation region 308. In addition to the charge-generation region 308, the intermediate layer 207 may further include an electron-relay layer 307 and an electron-injection buffer layer 306. In FIG. 1D, the light-emitting element includes the EL layer 203 over the first electrode 201, the intermediate layer 207 over the EL layer 203, and the second electrode 205 over the intermediate layer 207. In addition, as the intermediate layer 207 in FIG. 1D, the electron-injection buffer layer 306, the electron-relay layer 307, and the charge-generation region 308 are provided in this order from the EL layer 203 side.

When a voltage higher than the threshold voltage of the light-emitting element is applied between the first electrode 201 and the second electrode 205, holes and electrons are generated in the charge-generation region 308, and the holes move into the second electrode 205 and the electrons move into the electron-relay layer 307. The electron-relay layer 307 has a high electron-transport property and immediately transfers the electrons generated in the charge-generation region 308 to the electron-injection buffer layer 306. The electron-injection buffer layer 306 lowers a barrier to electron injection into the EL layer 203 and improves the efficiency of electron injection into the EL layer 203. In this manner, electrons generated in the charge-generation region 308 are injected into the LUMO (lowest unoccupied molecular orbital) level of the EL layer 203 through the electron-relay layer 307 and the electron-injection buffer layer 306.

In addition, the electron-relay layer 307 can prevent reaction at the interface between a substance contained in the charge-generation region 308 and a substance contained in the electron-injection buffer layer 306. Thus, it is possible to prevent interaction such as impairing the functions of the charge-generation region 308 and the electron-injection buffer layer 306.

Figure 1E:
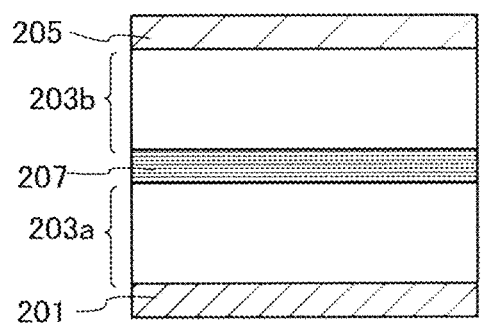
Figure 1F:
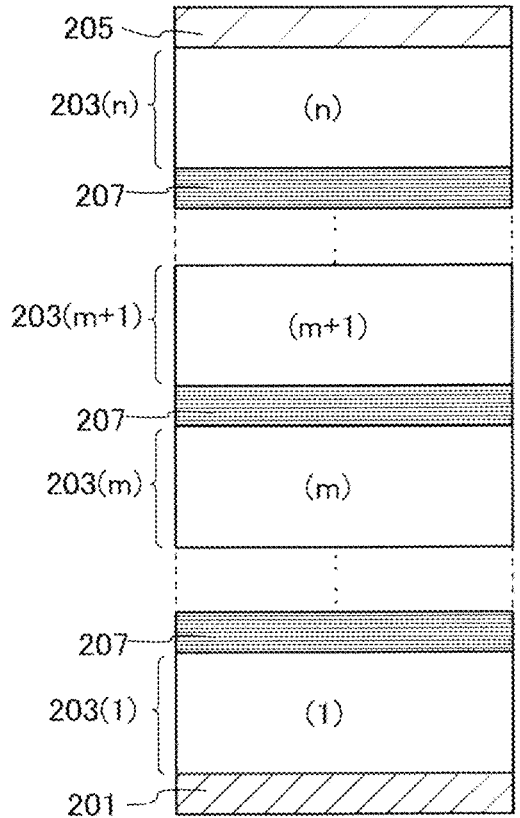

As illustrated in light-emitting elements in FIGS. 1E and 1F, a plurality of EL layers may be stacked between the first electrode 201 and the second electrode 205. In this case, the intermediate layer 207 is preferably provided between the stacked EL layers. For example, the light-emitting element illustrated in FIG. 1E includes the intermediate layer 207 between a first EL layer 203a and a second EL layer 203b. The light-emitting element illustrated in FIG. 1F includes n EL layers (n is a natural number of 2 or more) and the intermediate layers 207, an intermediate layer 207 being between an m-th EL layer 203($m$) and an (m+1)-th EL layer 203($m$+1). Note that in a light-emitting element of one embodiment of the present invention which includes a plurality of EL layers, the above-described composition (containing the first organic compound, the second organic compound, and the phosphorescent compound) is applied to at least one of the EL layers and may be applied to all the EL layers.

The behaviors of electrons and holes in the intermediate layer 207 provided between the EL layer 203($m$) and the EL layer 203($m$+1) will be described. When a voltage higher than the threshold voltage of the light-emitting element is applied between the first electrode 201 and the second electrode 205, holes and electrons are generated in the intermediate layer 207, and the holes move into the EL layer 203($m$+1) provided on the second electrode 205 side and the electrons move into the EL layer 203($m$) provided on the first electrode 201 side. The holes injected into the EL layer 203($m$+1) are recombined with electrons injected from the second electrode 205 side, so that a light-emitting substance contained in the EL layer 203($m$+1) emits light. Further, the electrons injected into the EL layer 203($m$) are recombined with holes injected from the first electrode 201 side, so that a light-emitting substance contained in the EL layer 203($m$) emits light. Thus, the holes and electrons generated in the intermediate layer 207 cause light emission in different EL layers.

Note that the EL layers can be provided in contact with each other when these EL layers allow the same structure as the intermediate layer to be formed therebetween. For example, when the charge-generation region is formed over one surface of an EL layer, another EL layer can be provided in contact with the surface.

Further, by making emission colors of the EL layers different, light emission of a desired color can be obtained from the light-emitting element as a whole. For example, the emission colors of first and second EL layers are complementary in a light-emitting element having the two EL layers, so that the light-emitting element can be made to emit white light as a whole. The same applies to a light-emitting element having three or more EL layers.

FIGS. 1B to 1E can be used in an appropriate combination. For example, the intermediate layer 207 can be provided between the second electrode 205 and the EL layer 203(n) in FIG. 1F.

Examples of materials which can be used for each layer will be given below. Note that each layer is not limited to a single layer, and may be a stack of two or more layers.

<Anode>

The electrode serving as the anode (the first electrode 201 in this embodiment) can be formed using one or more kinds of conductive metals and alloys, conductive compounds, and the like. In particular, it is preferable to use a material with a high work function (4.0 eV or more). Examples include indium tin oxide (ITO), indium tin oxide containing silicon or silicon oxide, indium zinc oxide, indium oxide containing tungsten oxide and zinc oxide, graphene, gold, platinum, nickel, tungsten, chromium, molybdenum, iron, cobalt, copper, palladium, and a nitride of a metal material (e.g., titanium nitride).

When the anode is in contact with the charge-generation region, any of a variety of conductive materials can be used regardless of their work functions; for example, aluminum, silver, an alloy containing aluminum, or the like can be used.

<Cathode>

The electrode serving as the cathode (the second electrode 205 in this embodiment) can be formed using one or more kinds of conductive metals and alloys, conductive compounds, and the like. In particular, it is preferable to use a material with a low work function (3.8 eV or less). Examples include aluminum, silver, an element belonging to Group 1 or 2 of the periodic table (e.g., an alkali metal such as lithium or cesium, an alkaline earth metal such as calcium or strontium, or magnesium), an alloy containing any of these elements (e.g., Mg—Ag or Al—Li), a rare earth metal such as europium or ytterbium, and an alloy containing arty of these rare earth metals.

Note that in the case where the cathode is in contact with the charge-generation region, any of a variety of conductive materials can be used regardless of its work function. For example, ITO, silicon, or indium tin oxide containing silicon oxide can be used.

The light-emitting element may have a structure in which one of the anode and the cathode is formed using a conductive film that transmits visible light and the other is formed using a conductive film that reflects visible light, or a structure in which both the anode and the cathode are formed using conductive films that transmit visible light.

The conductive film that transmits visible light can be formed using, for example, indium oxide, ITO, indium zinc oxide, zinc oxide, or zinc oxide to which gallium is added. Alternatively, a film of a metal material such as gold, platinum, nickel, tungsten, chromium, molybdenum, iron, cobalt, copper, palladium, or titanium, or a nitride of any of these metal materials (e.g., titanium nitride) can be formed thin so as to have a light-transmitting property. Further alternatively, graphene or the like may be used.

The conductive film that reflects visible light can be formed using, for example, a metal material such as aluminum, gold, platinum, silver, nickel, tungsten, chromium, molybdenum, iron, cobalt, copper, or palladium; an aluminum-containing alloy (aluminum alloy) such as an alloy of aluminum and titanium, an alloy of aluminum and nickel, or an alloy of aluminum and neodymium; or a silver-containing alloy such as an alloy of silver and copper. An alloy of silver and copper is preferable because of its high heat resistance. Further, lanthanum, neodymium, or germanium may be added to the metal material or the alloy.

The electrodes may be formed separately by a vacuum evaporation method or a sputtering method. Alternatively, when a silver paste or the like is used, a coating method or an inkjet method may be used.

<Hole-Injection Layer 301>

The hole-injection layer 301 contains a substance having a high hole-injection property.

Examples of the substance having a high hole-injection property include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

A phthalocyanine-based compound such as phthalocyanine (abbreviation: $H_2Pc$) or copper(II) phthalocyanine (abbreviation: CuPc) can also be used.

Further alternatively, it is possible to use an aromatic amine compound which is a low molecular organic compound, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), or 3-[N-(1-naphthyl)-N-(9-phenylcarbazol-3-yl)amino]-9-phenylcarbazole (abbreviation: PCzPCN1).

Further alternatively, it is possible to use a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-$N^1$-phenylamino}phenyl)methacrylamide] (abbreviation: PTPDMA), or poly[N,N'-bis(4-butylphenyl)-N,N'-bis(phenyl)benzidine] (abbreviation: Poly-TPD), or a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS).

The hole-injection layer 301 may serve as the charge-generation region. When the hole-injection layer 301 in contact with the anode serves as the charge-generation region, any of a variety of conductive materials can be used for the anode regardless of their work functions. Materials contained in the charge-generation region will be described later.

<Hole-Transport Layer 302>

The hole-transport layer 302 contains a substance having a high hole-transport property. The substance having the high hole-transport property is a substance having a property of transporting more holes than electrons, and is especially preferably a substance having a hole mobility of $10^{-6}$ $cm^2/Vs$ or more.

For the hole-transport layer 302, any of the organic compounds represented by the above general formulae (G0) to (G3) can be used. When any of the organic compounds represented by the above general formulae (G0) to (G3) is used for both the hole-transport layer 302 and the light-emitting layer 303, it is possible to lower a hole-injection barrier and thus possible to not only increase emission efficiency but also decrease a drive voltage. In other words, such a structure makes it possible not only to maintain high emission efficiency in a high luminance region as described above but also to keep a drive voltage low. As a result, a light-emitting element with little decrease in power efficiency due to voltage loss even at high luminance, that is, a light-emitting element with high power efficiency (low power consumption) can be obtained. It is particularly preferable that the hole-transport layer 302 and the light-emitting layer 303 contain the same organic compound in terms of the hole-injection barrier.

Other examples of the substance having a high hole-transport property are aromatic amine compounds such as 4,4'-bis[N-(1-naphthyl)-N-phenylamino]biphenyl (abbreviation: NPB or α-NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP), 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB).

Alternatively, it is possible to use a carbazole derivative such as 4,4'-di(N-carbazolyl)biphenyl (abbreviation: CBP), 9-[4-(10-phenyl-9-anthracenyl)phenyl]-9H-carbazole (abbreviation: CzPA), or 9-phenyl-3-[4-(10-phenyl-9-anthryl)phenyl]-9H-carbazole (abbreviation: PCzPA).

Further alternatively, it is possible to use an aromatic hydrocarbon compound such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth).

A high molecular compound such as PVK, PVTPA, PTPDMA, or Poly-TPD can also be used.

<Electron-Transport Layer 304>

The electron-transport layer 304 contains a substance having a high electron-transport property.

The substance having a high electron-transport property is an organic compound having a property of transporting more electrons than holes, and is especially preferably a substance having an electron mobility of $10^{-6}$ cm$^2$/Vs or more.

For the electron-transport layer 304, the second organic compound (the compound having the electron-transport property) contained in the light-emitting layer 303 can be used.

A metal complex such as tris(8-quinolinolato)aluminum (III) (abbreviation: Alq) or tris(4-methyl-8-quinolinolato)aluminum(III) (abbreviation: Almq$_3$) can be used for the electron-transport layer 304.

Further, a heteroaromatic compound such as bathophenanthroline (abbreviation: BPhen), bathocuproine (abbreviation: BCP), 3-(4-tert-butylphenyl)-4-(4-ethylphenyl)-5-(4-biphenylyl)-1,2,4-triazole (abbreviation: p-EtTAZ), or 4,4'-bis(5-methylbenzoxazol-2-yl)stilbene (abbreviation: BzOs) can be used.

Further, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py), or poly[(9,9-dioctylfluorene-2,7-diyl)-co-(2,2'-bipyridine-6,6'-diyl)] (abbreviation: PF-BPy) can be used.

<Electron-Injection Layer 305>

The electron-injection layer 305 contains a substance having a high electron-injection property.

Examples of the substance having a high electron-injection property include an alkali metal, an alkaline earth metal, a rare earth metal, and a compound thereof (e.g., an oxide thereof, a carbonate thereof, and a halide thereof), such as lithium, cesium, calcium, lithium oxide, lithium carbonate, cesium carbonate, lithium fluoride, cesium fluoride, calcium fluoride, and erbium fluoride.

The electron-injection layer 305 may contain the above-described substance having the high electron-transport property and a donor substance. For example, the electron-injection layer 305 may be formed using an Alq layer containing magnesium (Mg). When the substance having a high electron-transport property and the donor substance are contained, the mass ratio of the donor substance to the substance having the high electron-transport property is preferably from 0.001:1 to 0.1:1.

Examples of the donor substance include an alkali metal, an alkaline earth metal, a rare earth metal, and a compound thereof (e.g., an oxide thereof), such as lithium, cesium, magnesium, calcium, erbium, ytterbium, lithium oxide, calcium oxide, barium oxide, and magnesium oxide; a Lewis base; and an organic compound such as tetrathiafulvalene (abbreviation: TTF), tetrathianaphthacene (abbreviation: TTN), nickelocene, or decamethylnickelocene.

<Charge-Generation Region>

The charge-generation region included in the hole-injection layer and the charge-generation region 308 each contain a substance having a high hole-transport property and an acceptor substance (electron acceptor). The acceptor substance is preferably added so that the mass ratio of the acceptor substance to the substance having the high hole-transport property is from 0.1:1 to 4.0:1.

The charge-generation region is not limited to a structure in which a substance having a high hole-transport property and an acceptor substance are contained in the same film, and may have a structure in which a layer containing a substance having a high hole-transport property and a layer containing an acceptor substance are stacked. Note that in the case of a stacked-layer structure in which the charge-generation region is provided on the cathode side, the layer containing the substance having the high hole-transport property is in contact with the cathode, and in the case of a stacked-layer structure in which the charge-generation region is provided on the anode side, the layer containing the acceptor substance is in contact with the anode.

The substance having the high hole-transport property is an organic compound having a property of transporting more holes than electrons, and is especially preferably an organic compound having a hole mobility of $10^{-6}$ cm$^2$Ns or more.

Specifically, it is possible to use the compound represented by the above general formula (G0) or any of the substances having the high hole-transport property given as examples of substances that can be used for the hole-transport layer 302, e.g., aromatic amine compounds such as NPB and BPAFLP, carbazole derivatives such as CBP, CzPA, and PCzPA, aromatic hydrocarbon compounds such as t-BuDNA, DNA, and DPAnth, and high molecular compounds such as PVK and PVTPA.

Examples of the acceptor substance include halogen compounds such as 7,7,8,8-tetracyano-2,3,5,6-tetrafluoroquinodimethane (abbreviation: F$_4$-TCNQ) and chloranil, cyano compounds such as pirazino[2,3-f][1,10]phenanthroline-2,3-dicarbonitrile (abbreviation: PPDN) and dipyrazino[2,3-f:2'3'-h]quinoxaline-2,3,6,7,10,11-hexacarbonitrile (abbreviation: HAT-CN), transition metal oxides, and oxides of metals belonging to Groups 4 to 8 of the periodic table. Specifically, vanadium oxide, niobium oxide, tantalum oxide, chromium oxide, molybdenum oxide, tungsten oxide, manganese oxide, and rhenium oxide are preferable because of their high electron-accepting property. In particular, molybdenum oxide is preferable because of its stability in the atmosphere, low hygroscopic property, and ease of handling.

<Electron-Injection Buffer Layer 306>

The electron-injection buffer layer 306 contains a substance having a high electron-injection property. The electron-injection buffer layer 306 facilitates electron injection from the charge-generation region 308 into the EL layer 203. As the substance having the high electron-injection property, any of the above-described materials can be used. Alternatively, the electron-injection buffer layer 306 may contain any of the above-described substances having the high electron-transport property and donor substances.

<Electron-Relay Layer 307>

The electron-relay layer 307 immediately accepts electrons drawn out by the acceptor substance in the charge-generation region 308.

The electron-relay layer 307 contains a substance having a high electron-transport property. As the substance having the high electron-transport property, a phthalocyanine-based material or a metal complex having a metal-oxygen bond and an aromatic ligand is preferably used.

As the phthalocyanine-based material, specifically, it is possible to use CuPc, a phthalocyanine tin(II) complex (SnPc), a phthalocyanine zinc complex (ZnPc), cobalt(II) phthalocyanine, β-form (CoPc), phthalocyanine iron (FePc), or vanadyl 2,9,16,23-tetraphenoxy-29H,31H-phthalocyanine (PhO-VOPc).

As the metal complex having a metal-oxygen bond and an aromatic ligand, a metal complex having a metal-oxygen double bond is preferably used. A metal-oxygen double bond has an acceptor property; thus, electrons can be transferred (donated and accepted) more easily.

As the metal complex having a metal-oxygen bond and an aromatic ligand, a phthalocyanine-based material is also preferably used. In particular, vanadyl phthalocyanine (VOPc), a phthalocyanine tin(IV) oxide complex (SnOPc), or a phthalocyanine titanium oxide complex (TiOPc) is preferable because a metal-oxygen double bond is more likely to act on another molecule in terms of a molecular structure and an acceptor property is high.

As the phthalocyanine-based material, a phthalocyanine-based material having a phenoxy group is preferably used. Specifically, a phthalocyanine derivative having a phenoxy group, such as PhO-VOPc, is preferably used. The phthalocyanine derivative having a phenoxy group is soluble in a solvent; thus, the phthalocyanine derivative has an advantage of being easily handled during formation of a light-emitting element and an advantage of facilitating maintenance of an apparatus used for film formation.

Examples of other substances having the high electron-transport property include perylene derivatives such as 3,4,9,10-perylenetetracarboxylic dianhydride (abbreviation: PTCDA), 3,4,9,10-perylenetetracarboxylic bisbenzimidazole (abbreviation: PTCBI), N,N'-dioctyl-3,4,9,10-perylenetetracarboxylic diimide (abbreviation: PTCDI-C8H), N,N'-dihexyl-3,4,9,10-perylenetetracarboxylic diimide (abbreviation: Hex PTC), and the like. Alternatively, it is possible to use a nitrogen-containing condensed aromatic compound such as pirazino[2,3-f][1,10]phenanthroline-2,3-dicarbonitrile (abbreviation: PPDN), 2,3,6,7,10,11-hexacyano-1,4,5,8,9,12-hexaazatriphenylene (abbreviation: HAT(CN)$_6$), 2,3-diphenylpyrido[2,3-b]pyrazine (abbreviation: 2PYPR), or 2,3-bis(4-fluorophenyl)pyrido[2,3-b]pyrazine (abbreviation: F2PYPR). The nitrogen-containing condensed aromatic compound is preferably used for the electron-relay layer 307 because of its stability.

Further, it is possible to use 7,7,8,8-tetracyanoquinodimethane (abbreviation: TCNQ), 1,4,5,8-naphthalenetetracarboxylic dianhydride (abbreviation: NTCDA), perfluoropentacene, copper hexadecafluorophthalocyanine (abbreviation: F$_{16}$CuPc), N,N'-bis(2,2,3,3,4,4,5,5,6,6,7,7,8,8,8-pentadecafluorooctyl)-1,4,5,8-naphthalenetetracar boxylic diimide (abbreviation: NTCDI-C8F), 3',4'-dibutyl-5,5''-bis(dicyanomethylene)-5,5''-dihydro-2,2':5',2''-terthiophene (abbreviation: DCMT), or a methanofullerene (e.g., [6,6]-phenyl C$_{61}$ butyric acid methyl ester).

The electron-relay layer 307 may further contain any of the above-described donor substances. When the donor substance is contained in the electron-relay layer 307, electrons can be transferred easily and the light-emitting element can be driven at a lower voltage.

The LUMO levels of the substance having the high electron-transport property and the donor substance are preferably −5.0 eV to −3.0 eV, i.e., between the LUMO level of the acceptor substance contained in the charge-generation region 308 and the LUMO level of the substance having the high electron-transport property contained in the electron-transport layer 304 (or the LUMO level of the EL layer 203 in contact with the electron-relay layer 307 or with the electron-injection buffer layer 306 therebetween). When a donor substance is contained in the electron-relay layer 307, as the substance having the high electron-transport property, a substance having a LUMO level higher than the acceptor level of the acceptor substance contained in the charge-generation region 308 can be used.

The above-described layers included in the EL layer 203 and the intermediate layer 207 can be formed separately by any of the following methods: an evaporation method (including a vacuum evaporation method), a transfer method, a printing method, an inkjet method, a coating method, and the like.

By use of the light-emitting element described in this embodiment, a passive matrix light-emitting device or an active matrix light-emitting device in which driving of the light-emitting element is controlled by a transistor can be manufactured. Furthermore, the light-emitting device can be applied to an electronic device, a lighting device, or the like.

This embodiment can be combined with any of other embodiments as appropriate.

Embodiment 2

In this embodiment, a light-emitting element in one embodiment of the present invention will be described with reference to FIGS. 2A to 2C.

Figure 2A:
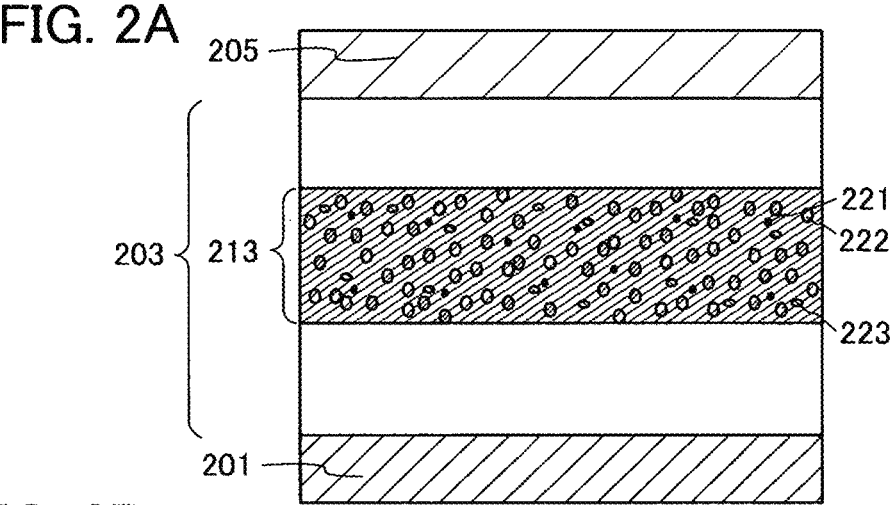
FIG. 2A illustrates an example of a light-emitting element in one embodiment of the present invention.

A light-emitting element illustrated in FIG. 2A includes an EL layer 203 between a first electrode 201 and a second electrode 205. The EL layer 203 includes a light-emitting layer 213.

In the light-emitting element illustrated in FIG. 2A, the light-emitting layer 213 contains a first organic compound 221, a second organic compound 222, and a phosphorescent compound 223. The first organic compound 221 is represented by the general formula (G0) shown in Embodiment 1 and has a molecular weight greater than or equal to 500 and less than or equal to 2000. The second organic compound 222 is a compound having an electron-transport property.

The phosphorescent compound 223 is a guest material in the light-emitting layer 213. In this embodiment, one of the first organic compound 221 and the second organic compound 222, the content of which is higher than that of the other in the light-emitting layer 213, is the host material in the light-emitting layer 213.

Note that it is preferable that a triplet excitation energy level ($T_1$ level) of each of the first organic compound 221 and the second organic compound 222 be higher than that of the phosphorescent compound 223. This is because, when the $T_1$ level of the first organic compound 221 (or the second organic compound 222) is lower than that of the phosphorescent compound 223, the triplet excitation energy of the phosphorescent compound 223, which is to contribute to light emission, is quenched by the first organic compound 221 (or the second organic compound 222) and accordingly the emission efficiency is decreased.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host molecule (a fluorescence spectrum in energy transfer from a singlet excited state, and a phosphorescence spectrum in energy transfer from a triplet excited state) largely overlap with an absorption spectrum of a guest molecule (specifically, a spectrum in an absorption band on the longest wavelength (lowest energy) side).

However, in the case of using a phosphorescent compound as a guest material, it is difficult to obtain an overlap between a fluorescence spectrum of a host material and an absorption spectrum in an absorption band on the longest wavelength (lowest energy) side of the guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed so that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of the host material and an absorption spectrum in an absorption band on the longest wavelength (lowest energy) side of the guest material so as to maximize energy transfer from a singlet excited state of the host material.

Thus, in this embodiment, a combination of the first organic compound 221 and the second organic compound 222 forms an exciplex.

The exciplex will be described with reference to FIGS. 2B and 2C.

Figure 2B:
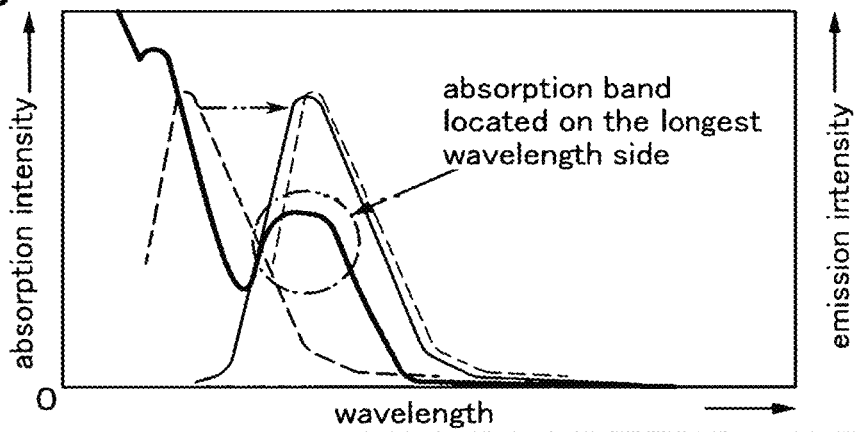
FIGS. 2B and 2C illustrate a concept of an exciplex in one embodiment of the present invention.
Figure 2C:
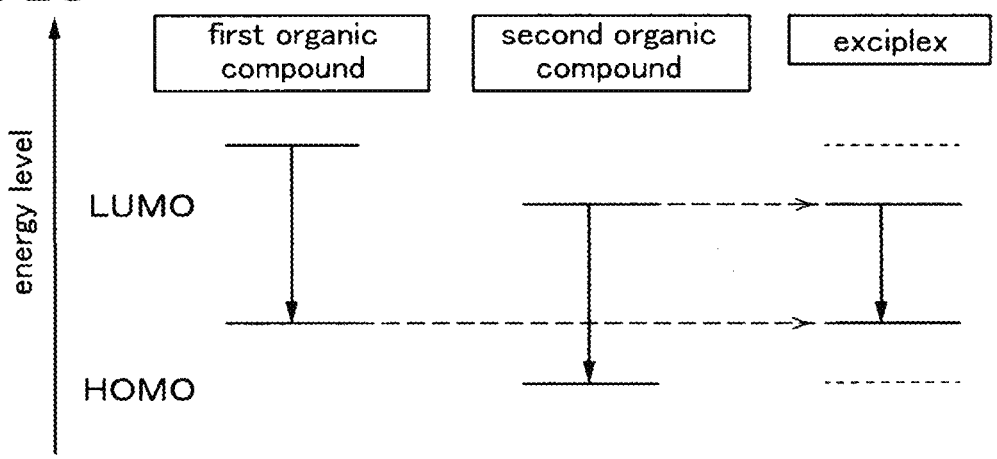

FIG. 2B is a schematic view showing the concept of an exciplex; a fluorescence spectrum of the first organic compound 221 (or the second organic compound 222), a phosphorescence spectrum of the first organic compound 221 (or the second organic compound 222), an absorption spectrum of the phosphorescent compound 223, and an emission spectrum of the exciplex are shown.

For example, in the light-emitting layer 213, the fluorescence spectrum of the first organic compound 221 and the fluorescence spectrum of the second organic compound 222 are converted into an emission spectrum of an exciplex which is located on the longer wavelength side. Moreover, when the first organic compound 221 and the second organic compound 222 are selected so that the emission spectrum of the exciplex largely overlaps with the absorption spectrum of the phosphorescent compound 223 (guest material), energy transfer from a singlet excited state can be maximized (see FIG. 2B).

Note that also in the case of a triplet excited state, energy transfer from the exciplex, not the host material, is considered to occur.

Thus, since the emission wavelength of the formed exciplex is longer than the emission wavelength (fluorescence wavelength) of each of the first organic compound 221 and the second organic compound 222, the fluorescence spectrum of the first organic compound 221 or the fluorescence spectrum of the second organic compound 222 can become an emission spectrum located on the longer wavelength side.

Furthermore, the exciplex is considered to have an extremely small difference between singlet excited energy and triplet excited energy. In other words, the emission spectrum of the exciplex from the single state and the emission spectrum thereof from the triplet state are highly close to each other. Accordingly, in the case where a design is implemented such that the emission spectrum of the exciplex (generally the emission spectrum of the exciplex from the singlet state) overlaps with the absorption band of the phosphorescent compound 223 (guest material) which is located on the longest wavelength side as described above, the emission spectrum of the exciplex from the triplet state (which is not observed at room temperature and not observed even at low temperature in many cases) also overlaps with the absorption band of the phosphorescent compound 223 (guest material) which is located on the longest wavelength side. In other words, the efficiency of the energy transfer from the triplet excited state as well as the efficiency of the energy transfer from the singlet excited state can be increased, and as a result, light emission can be efficiently obtained from both the singlet and triplet excited states.

In the above manner, the light-emitting element in one embodiment of the present invention transfers energy by utilizing an overlap between the emission spectrum of the exciplex formed in the light-emitting layer 213 and the absorption spectrum of the phosphorescent compound 223 (guest material) and thus has high energy transfer efficiency.

In addition, the exciplex exists only in an excited state and thus has no ground state capable of absorbing energy. Therefore, a phenomenon in which the phosphorescent compound 223 (guest material) is deactivated by energy transfer from the phosphorescent compound 223 (guest material) in the singlet excited state and triplet excited state to the exciplex before light emission (i.e., emission efficiency is lowered) is not considered to occur in principle.

Note that the above-described exciplex is formed by an interaction between dissimilar molecules in excited states. The exciplex is generally known to be easily formed between a material having a relatively deep LUMO level and a material having a relatively shallow highest occupied molecular orbital (HOMO) level.

Here, concepts of the energy levels of the first organic compound 221, the second organic compound 222, and the exciplex are described with reference to FIG. 2C. Note that FIG. 2C schematically illustrates the energy levels of the first organic compound 221, the second organic compound 222, and the exciplex.

The HOMO levels and the LUMO levels of the first organic compound 221 and the second organic compound 222 are different from each other. Specifically, the energy levels vary in the following order: the HOMO level of the second organic compound 222<the HOMO level of the first organic compound 221<the LUMO level of the second organic compound 222<the LUMO level of the first organic compound 221. When the exciplex is formed by these two organic compounds, the LUMO level and the HOMO level of the exciplex originate from the second organic compound 222 and the first organic compound 221, respectively (see FIG. 2C).

The emission wavelength of the exciplex depends on a difference in energy between the HOMO level and the LUMO level. As a general tendency, when the energy difference is large, the emission wavelength is short, and when the energy difference is small, the emission wavelength is long.

Therefore, the energy difference of the exciplex is smaller than the energy difference of the first organic compound 221 and the energy difference of the second organic compound 222. In other words, the emission wavelength of the exciplex is longer than the emission wavelengths of the first organic compound 221 and the second organic compound 222.

The process of the exciplex formation in one embodiment of the present invention can be either of the following two processes.

One process of the exciplex formation is that an exciplex is formed from the first organic compound 221 and the second organic compound 222 having carriers (cation or anion).

In general, when an electron and a hole are recombined in a host material, excitation energy is transferred from the host material in an excited state to a guest material, whereby the guest material is brought into an excited state to emit light. Before the excitation energy is transferred from the host material to the guest material, the host material itself emits light or the excitation energy turns into thermal energy, which leads to partial deactivation of the excitation energy.

However, in one embodiment of the present invention, an exciplex is formed from the first organic compound 221 and the second organic compound 222 having carriers (cation or anion); therefore, formation of singlet excitons of the first organic compound 221 and the second organic compound 222 can be suppressed. In other words, there can be a process where an exciplex is directly formed without formation of a singlet exciton. Thus, deactivation of the singlet excitation energy can be inhibited. Accordingly, a light-emitting element having a long lifetime can be obtained.

For example, in the case where the first organic compound 221 is a hole-trapping compound having the property of easily capturing holes (carrier) (having a shallow HOMO level) among hole-transport materials and the second organic compound 222 is an electron-trapping compound having the property of easily capturing electrons (carrier) (having a deep LUMO level) among electron-transport materials, an exciplex is formed directly from a cation of the first organic compound 221 and an anion of the second organic compound 222. An exciplex formed through such a process is particularly referred to as an electroplex.

A light-emitting element having high emission efficiency can be obtained by suppressing the generation of the singlet excited states of the first organic compound 221 and the second organic compound 222 and transferring energy from an electroplex to the phosphorescent compound 223 (guest material), in the above-described manner. Note that in this case, the generation of the triplet excited states of the first organic compound 221 and the second organic compound 222 is similarly suppressed and an exciplex is directly formed; therefore, energy transfer is considered to occur from the exciplex to the phosphorescent compound 223 (guest material).

The other process of the exciplex formation is an elementary process where one of the first organic compound 221 and the second organic compound 222 forms a singlet exciton and then interacts with the other in the ground state to form an exciplex. Unlike an electroplex, a singlet excited state of the first organic compound 221 or the second organic compound 222 is temporarily generated in this case, but this is rapidly converted into an exciplex, and thus, deactivation of singlet excitation energy, reaction from a singlet excited state, and the like can be inhibited. This makes it possible to inhibit deactivation of excitation energy of the first organic compound 221 or the second organic compound 222; thus, a light-emitting element having a long lifetime can be obtained. Note that in this case, it is considered that the triplet excited state of the first organic compound 221 or the second organic compound 222 is similarly rapidly converted into an exciplex and energy is transferred from the exciplex to the phosphorescent compound 223 (guest material).

Note that, in the case where the first organic compound 221 is a hole-trapping compound, the second organic compound 222 is an electron-trapping compound, and the difference between the HOMO levels and the difference between the LUMO levels of these compounds are large (specifically, 0.3 eV or more), holes are selectively injected into the first organic compound 221 and electrons are selectively injected into the second organic compound 222. In this case, it is thought that the process where an electroplex is formed takes precedence over the process where an exciplex is formed through a singlet exciton.

In general, energy transfer from the singlet excited state or triplet excited state of a host material to a phosphorescent compound is considered. On the other hand, one embodiment of the present invention greatly differs from a conventional technique in that an exciplex of a host material and another material is formed first and energy transfer from the exciplex is used. In addition, this difference provides unprecedentedly high emission efficiency.

Note that in general, the use of an exciplex for a light-emitting layer of a light-emitting element has a value such as being capable of controlling the emission color, but usually causes a significant decrease in emission efficiency. Therefore, the use of an exciplex has been considered unsuitable for obtaining a highly efficient light-emitting element. However, the use of an exciplex as a medium for energy transfer enables, on the contrary, emission efficiency to be maximized as shown in one embodiment of the present invention. This technical idea conflicts with the conventional fixed idea.

To make the emission spectrum of the exciplex and the absorption spectrum of the phosphorescent compound 223 (guest material) sufficiently overlap each other, the difference between the energy of a peak of the emission spectrum and the energy of a peak of the absorption band on the lowest energy side in the absorption spectrum is preferably 0.3 eV or less. The difference is more preferably 0.2 eV or less, even more preferably 0.1 eV or less.

In the light-emitting element in one embodiment of the present invention, it is also preferable that the excitation energy of the exciplex be sufficiently transferred to the phosphorescent compound 223 (guest material), and that light emission from the exciplex be not substantially observed. Therefore, energy is preferably transferred to the phosphorescent compound 223 (guest material) through the exciplex so that the phosphorescent compound 223 emits phosphorescence.

In the case where a phosphorescent compound is used as the host material in the light-emitting element in one embodiment of the present invention, the host material itself is likely to emit light and unlikely to allow energy to be transferred to the guest material. In this case, it is favorable if the phosphorescent compound used as the host material could emit light efficiently, but it is difficult to achieve high emission efficiency because the host material causes the problem of concentration quenching. Therefore, the case where at least one of the first organic compound 221 and the second organic compound 222 is a fluorescent compound (i.e., a compound which is likely to undergo light emission or thermal deactivation from the singlet excited state) is effective. Therefore, it is preferable that at least one of the first organic compound 221 and the second organic compound 222 be a fluorescent compound.

In the light-emitting element described in this embodiment, energy transfer efficiency can be improved owing to energy transfer utilizing an overlap between an emission spectrum of an exciplex and an absorption spectrum of a phosphorescent compound (guest material); accordingly, the light-emitting element can achieve high emission efficiency.

Note that the structure described in this embodiment can be combined as appropriate with any of the structures described in the other embodiments.

Embodiment 3

Figure 3A:
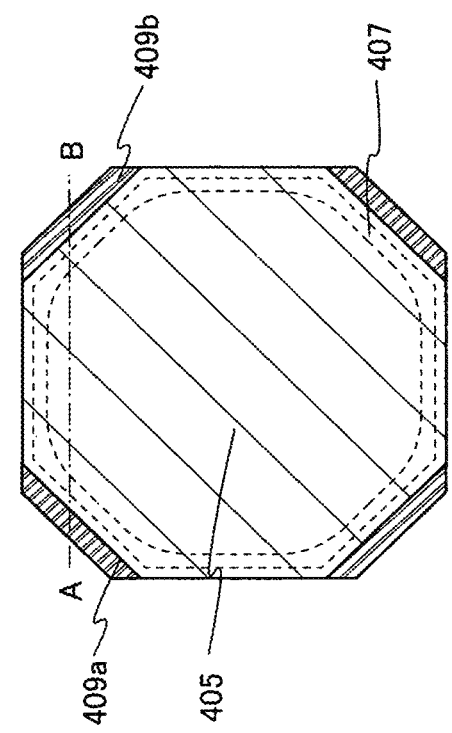
FIGS. 3A and 3B illustrate an example of a light-emitting device in one embodiment of the present invention.
Figure 3B:
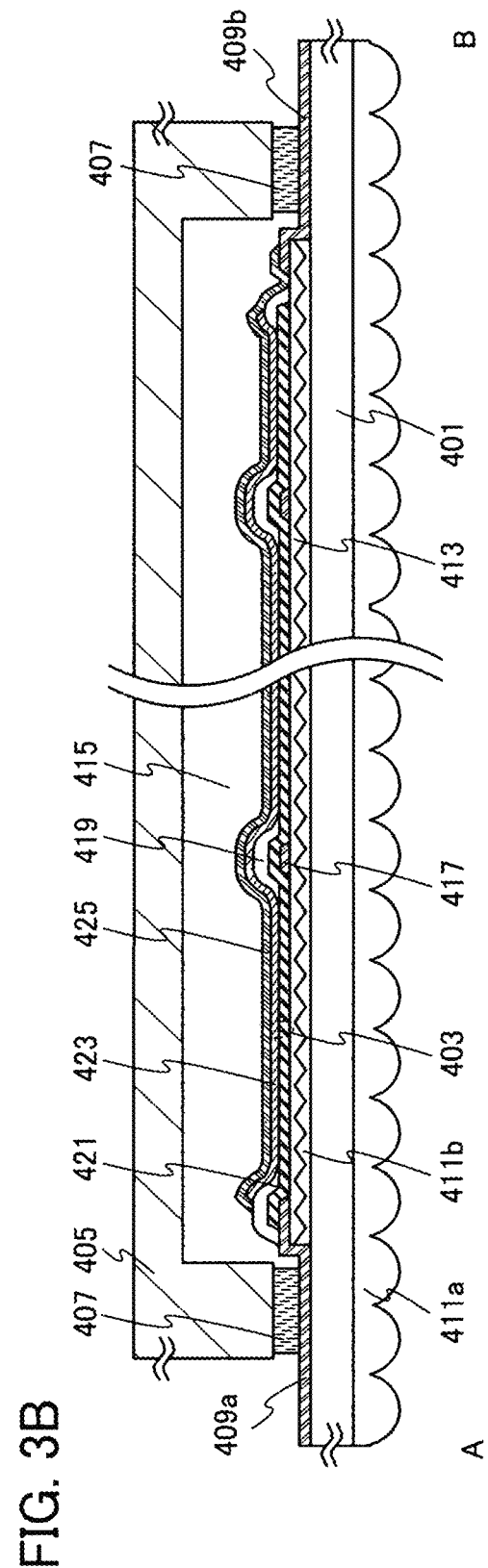

In this embodiment, a light-emitting device in one embodiment of the present invention will be described with reference to FIGS. 3A and 3B. FIG. 3A is a plan view of a light-emitting device in one embodiment of the present invention, and FIG. 3B is a cross-sectional view taken along dashed-dotted line A-B in FIG. 3A.

In the light-emitting device of this embodiment, a light-emitting element 403 (a first electrode 421, an EL layer 423, and a second electrode 425) is provided in a space 415 surrounded by a support substrate 401, a sealing substrate 405, and a sealing material 407. The light-emitting element 403 has a bottom-emission structure; specifically, the first electrode 421 which transmits visible light is provided over the support substrate 401, the EL layer 423 is provided over the first electrode 421, and the second electrode 425 which reflects visible light is provided over the EL layer 423.

As the light-emitting element 403 of this embodiment, the light-emitting element in one embodiment of the present invention is used. Since the light-emitting element in one embodiment of the present invention has a long lifetime, a light-emitting device having high reliability can be obtained. In addition, since the light-emitting element in one embodiment of the present invention exhibits high emission efficiency in a high luminance region, a light-emitting device with high emission efficiency can be obtained.

A first terminal 409a is electrically connected to an auxiliary wiring 417 and the first electrode 421. An insulating layer 419 is provided over the first electrode 421 in a region which overlaps with the auxiliary wiring 417. The first terminal 409a is electrically insulated from the second electrode 425 by the insulating layer 419. A second terminal 409b is electrically connected to the second electrode 425. Note that although the first electrode 421 is formed over the auxiliary wiring 417 in this embodiment, the auxiliary wiring 417 may be formed over the first electrode 421.

Since the organic EL element emits light in a region having a refractive index higher than that of the atmosphere, total reflection may occur inside the organic EL element or at the interface between the organic EL element and the atmosphere under a certain condition when light is extracted to the atmosphere, which results in a light extraction efficiency of the organic EL element lower than 100%.

Therefore, a light extraction structure 411a is preferably provided at the interface between the support substrate 401 and the atmosphere. The refractive index of the support substrate 401 is higher than that of the atmosphere. Therefore, when provided at the interface between the support substrate 401 and the atmosphere, the light extraction structure 411a can reduce light which cannot be extracted to the atmosphere due to total reflection, resulting in an increase in the light extraction efficiency of the light-emitting device.

In addition, a light extraction structure 411b is preferably provided at the interface between the light-emitting element 403 and the support substrate 401.

However, unevenness of the first electrode 421 might lead to generation of leakage current in the EL layer 423 formed over the first electrode 421. Therefore, in this embodiment, a planarization layer 413 having a refractive index higher than or equal to that of the EL layer 423 is provided in contact with the light extraction structure 411b. Accordingly, the first electrode 421 can be a flat film, and generation of leakage current in the EL layer 423 due to the unevenness of the first electrode 421 can be prevented. Further, because of the light extraction structure 411b at the interface between the planarization layer 413 and the support substrate 401, light which cannot be extracted to the atmosphere due to total reflection can be reduced, so that the light extraction efficiency of the light-emitting device can be increased.

The present invention is not limited to the structure in which the support substrate 401, the light extraction structure 411a, and the light extraction structure 411b are different components as in FIG. 3B. Two or all of these may be formed as one component. Further, the planarization layer 413 is not necessarily provided in the case where the light extraction structure 411b does not cause the first electrode 421 to have surface unevenness (e.g., in the case where the light extraction structure 411b does not have surface unevenness), for example.

The present invention is not limited to the structure in which the light-emitting device is octagonal as illustrated in FIG. 3A. The light-emitting device may have any other polygonal shape or a shape having a curved portion. In particular, the light-emitting device preferably has a triangular, quadrilateral, or hexagonal shape or the like so that a plurality of light-emitting devices can be provided in a limited area without a redundant space or so that a light-emitting device can be formed using a limited substrate area efficiently. Further, the number of light-emitting elements included in the light-emitting device is not limited to one and may be more than one.

The shape of the unevenness of the light extraction structure 411a and the light extraction structure 411b does not necessarily have regularity. When the shape of the unevenness is periodic, the unevenness functions as a diffraction grating depending on the size of the unevenness, so that an interference effect is increased and light with a certain wavelength is easily extracted to the atmosphere. Therefore, it is preferable that the shape of the unevenness be not periodic.

There is no particular limitation on the bottom shape of the unevenness; for example, the shape may be a polygon such a triangle or a quadrangle, a circle, or the like. When the bottom shape of the unevenness has regularity, the unevenness is preferably provided so that gaps are not formed between adjacent portions of the unevenness. A regular hexagon can be given as an example of a preferable bottom shape.

There is no particular limitation on the shape of the unevenness; for example, a hemisphere or a shape with a vertex such as a circular cone, a pyramid (e.g., a triangular pyramid or a quadrangular pyramid), or an umbrella shape can be used.

It is particularly preferable that the size or height of the unevenness be greater than or equal to 1 µm, in which case the influence of interference of light can be reduced.

The light extraction structure 411a and the light extraction structure 411b can be directly manufactured on the support substrate 401. For example, the light extraction structure 411a and the light extraction structure 411b can be formed using any of the following methods as appropriate: an etching method, a sand blasting method, a microblast processing method, a frost processing method, a droplet discharge method, a printing method (screen printing or offset printing by which a pattern is formed), a coating method such as a spin coating method, a dipping method, a dispenser method, an imprint method, a nanoimprint method, and the like.

As a material of the light extraction structure 411a and the light extraction structure 411b, a resin can be used, for example. Alternatively, for the light extraction structure 411a and the light extraction structure 411b, a hemispherical lens, a micro lens array, a film provided with an uneven surface structure, a light diffusing film, or the like can be used. For example, the light extraction structure 411a and the light extraction structure 411b can be formed by attaching the lens or film to the support substrate 401 with an adhesive or the like which has substantially the same refractive index as the support substrate 401 or the lens or film.

The surface of the planarization layer 413 which is in contact with the first electrode 421 is flatter than the surface of the planarization layer 413 which is in contact with the light extraction structure 411b. Therefore, the first electrode 421 can be a flat film. As a result, generation of leakage current in the EL layer 423 due to unevenness of the first electrode 421 can be suppressed. As a material of the planarization layer 413, glass, resin, or the like having a high refractive index can be used. The planarization layer 413 has a light-transmitting property.

This embodiment can be combined with any of other embodiments as appropriate.

Embodiment 4

Figure 4A:
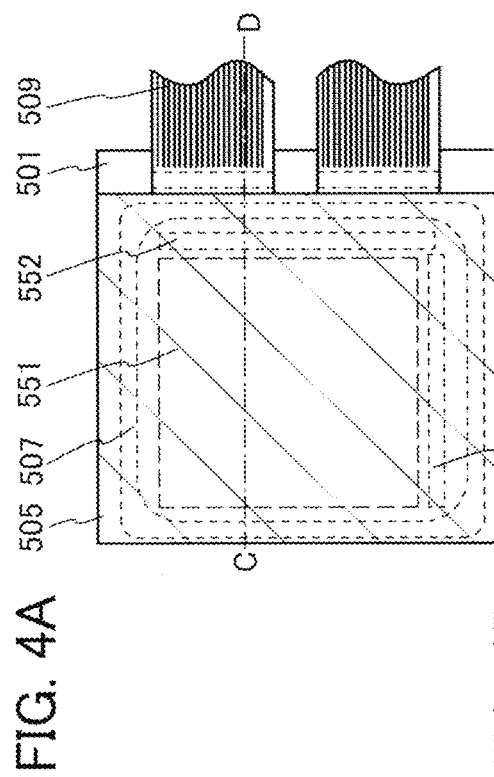
FIGS. 4A and 4B illustrate an example of a light-emitting device in one embodiment of the present invention.

In this embodiment, a light-emitting device in one embodiment of the present invention will be described with reference to FIGS. 4A and 4B. FIG. 4A is a plan view of a light-emitting device in one embodiment of the present invention, and FIG. 4B is a cross-sectional view taken along dashed-dotted line C-D in FIG. 4A.

An active matrix light-emitting device in this embodiment includes, over a support substrate 501, a light-emitting portion 551, a driver circuit portion 552 (gate side driver circuit portion), a driver circuit portion 553 (source side driver circuit portion), and a sealing material 507. The light-emitting portion 551 and the driver circuit portions 552 and 553 are sealed in a space 515 surrounded by the support substrate 501, the sealing substrate 505, and the sealing material 507.

Figure 4B:
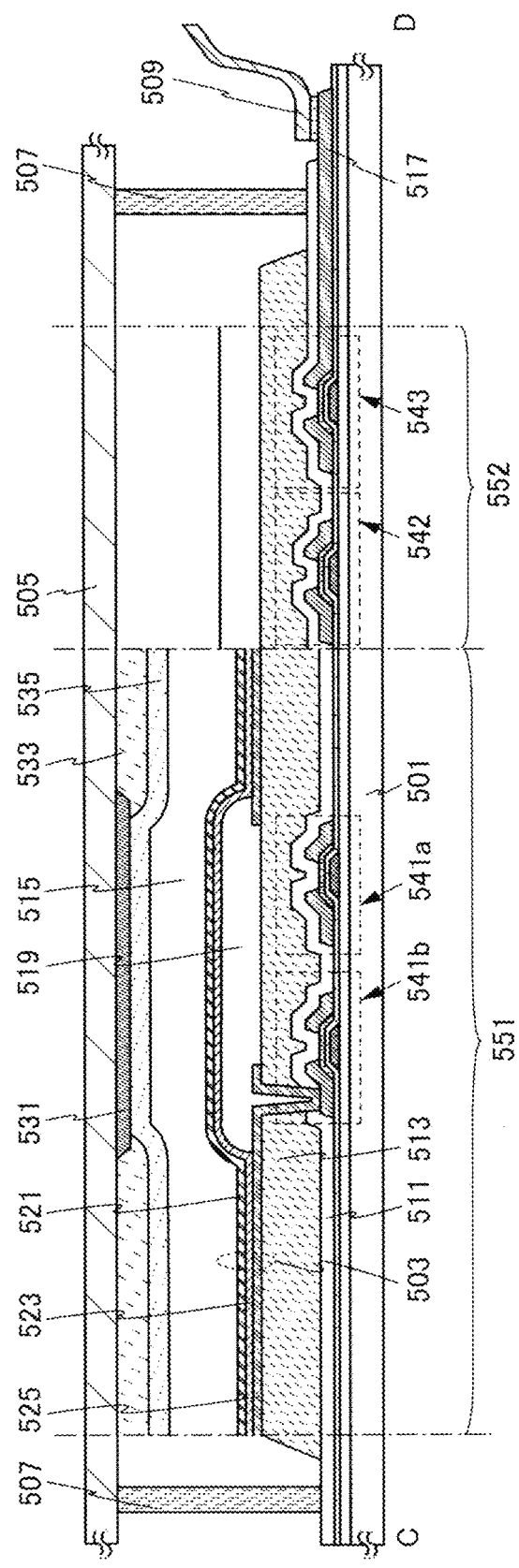

The light-emitting portion 551 illustrated in FIG. 4B includes a plurality of light-emitting units each including a switching transistor 541a, a current control transistor 541b, and a second electrode 525 electrically connected to a wiring (a source electrode or a drain electrode) of the transistor 541b.

A light-emitting element 503 has a top-emission structure and includes a first electrode 521 which transmits visible light, an EL layer 523, and the second electrode 525 which reflects visible light. Further, a partition 519 is formed so as to cover an end portion of the second electrode 525.

As the light-emitting element 503 of this embodiment, the light-emitting element in one embodiment of the present invention is used. Since the light-emitting element in one embodiment of the present invention has a long lifetime, a light-emitting device having high reliability can be obtained. In addition, since the light-emitting element in one embodiment of the present invention exhibits high emission efficiency in a high luminance region, a light-emitting device with high emission efficiency can be obtained.

Over the support substrate 501, a lead wiring 517 for connecting an external input terminal through which a signal (e.g., a video signal, a clock signal, a start signal, or a reset signal) or a potential from the outside is transmitted to the driver circuit portion 552 or 553 is provided. Here, an example is described in which a flexible printed circuit (FPC) 509 is provided as the external input terminal. Note that a printed wiring board (PWB) may be attached to the FPC 509. In this specification, the light-emitting device includes in its category the light-emitting device itself and the light-emitting device provided with the FPC or the PWB.

The driver circuit portions 552 and 553 include a plurality of transistors. FIG. 4B illustrates an example in which the driver circuit portion 552 has a CMOS circuit which is a combination of an n-channel transistor 542 and a p-channel transistor 543. A circuit included in the driver circuit portion can be formed with various types of circuits such as a CMOS circuit, a PMOS circuit, or an NMOS circuit. The present invention is not limited to a driver-integrated type described in this embodiment in which the driver circuit is formed over the substrate over which the light-emitting portion is formed. The driver circuit can be formed over a substrate that is different from the substrate over which the light-emitting portion is formed.

To prevent an increase in the number of manufacturing steps, the lead wiring 517 is preferably formed using the same material and the same step(s) as those of the electrode or the wiring in the light-emitting portion or the driver circuit portion.

Described in this embodiment is an example in which the lead wiring 517 is formed using the same material and the same step(s) as those of the source electrodes and the drain electrodes of the transistors included in the light-emitting portion 551 and the driver circuit portion 552.

In FIG. 4B, the sealing material 507 is in contact with a first insulating layer 511 over the lead wiring 517. The adhesion of the sealing material 507 to metal is low in some cases. Therefore, the sealing material 507 is preferably in contact with an inorganic insulating film over the lead wiring 517. Such a structure enables a light-emitting device to have high sealing capability, high adhesion, and high reliability. Examples of the inorganic insulating film include oxide films of metals and semiconductors, nitride films of metals and semiconductors, and oxynitride films of metals and semiconductors, and specifically, a silicon oxide film, a silicon nitride film, a silicon oxynitride film, a silicon nitride oxide film, an aluminum oxide film, a titanium oxide film, and the like.

The first insulating layer 511 has an effect of preventing diffusion of impurities into a semiconductor included in the transistor. As the second insulating layer 513, an insulating film having a planarization function is preferably selected in order to reduce surface unevenness due to the transistor.

There is no particular limitation on the structure of the transistor used in the light-emitting device of one embodiment of the present invention. A top-gate transistor may be used, or a bottom-gate transistor such as an inverted staggered transistor may be used. The transistor may be a channel-etched transistor or a channel-protective transistor. In addition, there is no particular limitation on a material used for the transistor.

A semiconductor layer can be formed using silicon or an oxide semiconductor. As silicon, single crystal silicon, polycrystalline silicon, or the like can be used as appropriate. As an oxide semiconductor, an In—Ga—Zn-based metal oxide or the like can be used as appropriate. Note that the transistor is preferably formed using an oxide semiconductor which is an In—Ga—Zn-based metal oxide for a semiconductor layer so as to have low off-state current, in which case an off-state leakage current of the light-emitting element can be reduced.

The sealing substrate 505 is provided with a color filter 533 which is a coloring layer overlapping with the light-emitting element 503 (its light-emitting region). The color filter 533 is provided to control the color of light emitted from the light-emitting element 503. For example, in a full-color display device using white light-emitting elements, a plurality of light-emitting units provided with color filters of different colors are used. In that case, three colors, red (R), green (G), and blue (B), may be used, or four colors, red (R), green (G), blue (B), and yellow (Y), may be used.

Further, a black matrix 531 is provided between adjacent color filters 533 (so as to overlap with the partition 519). The black matrix 531 shields a light-emitting unit from light emitted from the light-emitting elements 503 in adjacent light-emitting units and prevents color mixture between the adjacent light-emitting units. When the color filter 533 is provided so that its end portion overlaps with the black matrix 531, light leakage can be reduced. The black matrix 531 can be formed using a material that blocks light emitted from the light-emitting element 503, for example, a material such as a metal or a resin. Note that the black matrix 531 may be provided also in a region overlapping with the driver circuit portion 552 or the like besides the light-emitting portion 551.

Further, an overcoat layer 535 is formed so as to cover the color filter 533 and the black matrix 531. For the overcoat layer 535, a material which transmits light emitted from the light-emitting element 503 is used, and an inorganic insulating film or an organic insulating film can be used, for example. The overcoat layer 535 is not necessarily provided when not needed.

A structure of the present invention is not limited to the light-emitting device using a color filter method, which is described as an example in this embodiment. For example, a separate coloring method or a color conversion method may be used.

This embodiment can be combined with any of other embodiments as appropriate.

Embodiment 5

In this embodiment, examples of electronic devices and lighting devices to which the light-emitting device in one embodiment of the present invention is applied will be described with reference to FIGS. 5A to 5E and FIGS. 6A and 6B.

Electronic devices of this embodiment each include the light-emitting device of one embodiment of the present invention in a display portion. Lighting devices of this embodiment each include the light-emitting device of one embodiment of the present invention in a light-emitting portion (lighting portion). Highly reliable electronic devices and highly reliable lighting devices can be provided by adopting the light-emitting device of one embodiment of the present invention. In addition, electronic devices and lighting devices having high emission efficiency can be provided by adopting the light-emitting device of one embodiment of the present invention.

Examples of electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and lighting devices are illustrated in FIGS. 5A to 5E and FIGS. 6A and 6B.

FIG. 5A illustrates an example of a television device. In a television device 7100, a display portion 7102 is incorporated in a housing 7101. The display portion 7102 is capable of displaying images. The light-emitting device in one embodiment of the present invention can be used for the display portion 7102. In addition, here, the housing 7101 is supported by a stand 7103.

The television device 7100 can be operated with an operation switch provided in the housing 7101 or a separate remote controller 7111. With operation keys of the remote controller 7111, channels and volume can be controlled and images displayed on the display portion 7102 can be controlled. The remote controller 7111 may be provided with a display portion for displaying data output from the remote controller 7111.

Note that the television device 7100 is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 5B illustrates an example of a computer. A computer 7200 includes a main body 7201, a housing 7202, a display portion 7203, a keyboard 7204, an external connection port 7205, a pointing device 7206, and the like. Note that this computer is manufactured by using the light-emitting device of one embodiment of the present invention for the display portion 7203.

FIG. 5C illustrates an example of a portable game machine. A portable game machine 7300 has two housings, a housing 7301a and a housing 7301b, which are connected with a joint portion 7302 so that the portable game machine can be opened or closed. The housing 7301a incorporates a display portion 7303a, and the housing 7301b incorporates a display portion 7303b. In addition, the portable game machine illustrated in FIG. 5C includes a speaker portion 7304, a recording medium insertion portion 7305, an operation key 7306, a connection terminal 7307, a sensor 7308 (a sensor having a function of measuring or sensing force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), an LED lamp, a microphone, and the like. It is needless to say that the structure of the portable game machine is not limited to the above structure as long as the light-emitting device of one embodiment of the present invention is used for at least either the display portion 7303*a* or the display portion 7303*b*, or both, and may include other accessories as appropriate. The portable game machine illustrated in FIG. 5C has a function of reading out a program or data stored in a recoding medium to display it on the display portion, and a function of sharing information with another portable game machine by wireless communication. Note that functions of the portable game machine illustrated in FIG. 5C are not limited to them, and the portable game machine can have various functions.

FIG. 5D illustrates an example of a cellular phone. A cellular phone 7400 is provided with a display portion 7402 incorporated in a housing 7401, an operation button 7403, an external connection port 7404, a speaker 7405, a microphone 7406, and the like. Note that the cellular phone 7400 is manufactured by using the light-emitting device of one embodiment of the present invention for the display portion 7402.

When the display portion 7402 of the cellular phone 7400 illustrated in FIG. 5D is touched with a finger or the like, data can be input into the cellular phone. Further, operations such as making a call and creating an e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, a character input mode mainly for inputting characters is selected for the display portion 7402 so that characters displayed on the screen can be input.

When a sensing device including a sensor such as a gyroscope sensor or an acceleration sensor for detecting inclination is provided inside the cellular phone 7400, display on the screen of the display portion 7402 can be automatically changed in direction by determining the orientation of the cellular phone 7400 (whether the cellular phone 7400 is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by the display portion 7402 while in touch with the palm or the finger, whereby personal authentication can be performed. Further, when a backlight or a sensing light source which emits near-infrared light is provided in the display portion, an image of a finger vein, a palm vein, or the like can be taken.

FIG. 5E illustrates an example of a fordable tablet terminal (in an open state). A tablet terminal 7500 includes a housing 7501*a*, a housing 7501*b*, a display portion 7502*a*, and a display portion 7502*b*. The housing 7501*a* and the housing 7501*b* are connected by a hinge 7503 and can be opened and closed using the hinge 7503 as an axis. The housing 7501*a* includes a power switch 7504, operation keys 7505, a speaker 7506, and the like. Note that the tablet terminal 7500 is manufactured by using the light-emitting device of one embodiment of the present invention for either the display portion 7502*a* or the display portion 7502*b*, or both.

Part of the display portion 7502*a* or the display portion 7502*b* can be used as a touch panel region, where data can be input by touching displayed operation keys. For example, a keyboard can be displayed on the entire region of the display portion 7502*a* so that the display portion 7502*a* is used as a touch screen, and the display portion 7502*b* can be used as a display screen.

Figure 6A:
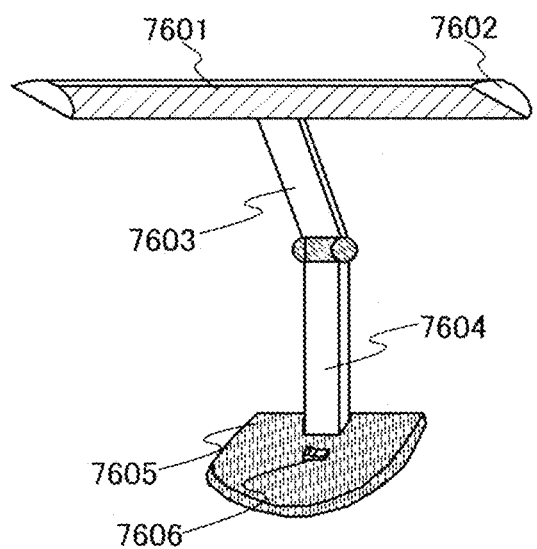
FIGS. 6A and 6B illustrate examples of lighting devices.

FIG. 6A illustrates a desk lamp, which includes a lighting portion 7601, a shade 7602, an adjustable arm 7603, a support 7604, a base 7605, and a power switch 7606. The desk lamp is manufactured by using the light-emitting device of one embodiment of the present invention for the lighting portion 7601. Note that the lamp also includes ceiling lights, wall lights, and the like in its category.

Figure 6B:
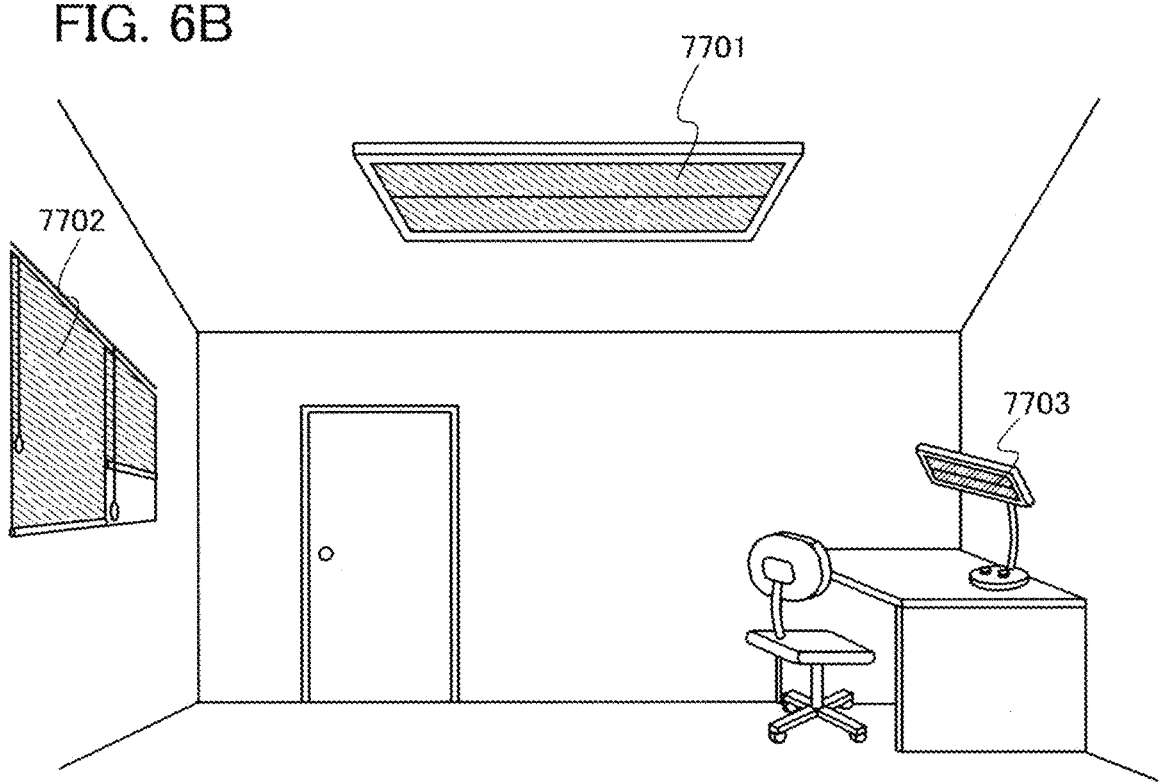

FIG. 6B illustrates an example in which the light-emitting device of one embodiment of the present invention is used for an indoor lamp 7701. Since the light-emitting device of one embodiment of the present invention can have a larger area, it can be used as a large-area lighting device. In addition, the light-emitting device can be used as a roll-type lamp 7702. As illustrated in FIG. 6B, a desk lamp 7703 described with reference to FIG. 6A may be used in a room provided with the indoor lamp 7701.

Example 1

Figure 7:
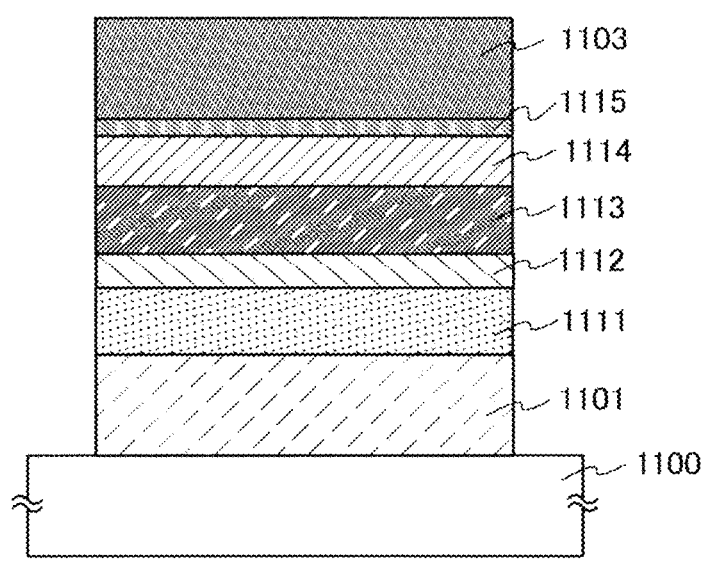
FIG. 7 illustrates a light-emitting element in examples.

In this example, a light-emitting element of one embodiment of the present invention will be described with reference to FIG. 7. Chemical formulae of materials used in this example are shown below.

[Chemical formula 24]

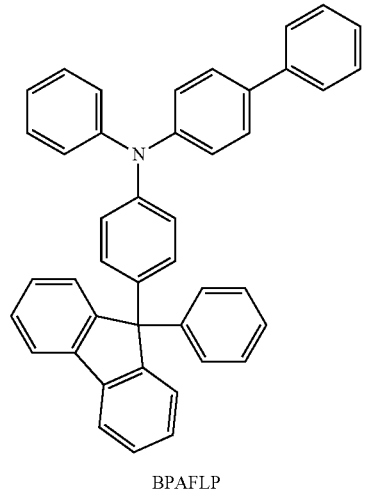

BPAFLP

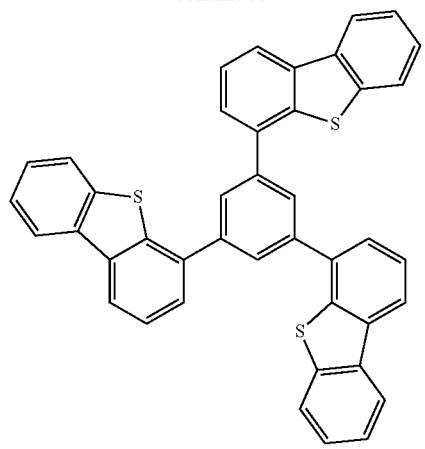
DBT3P-II
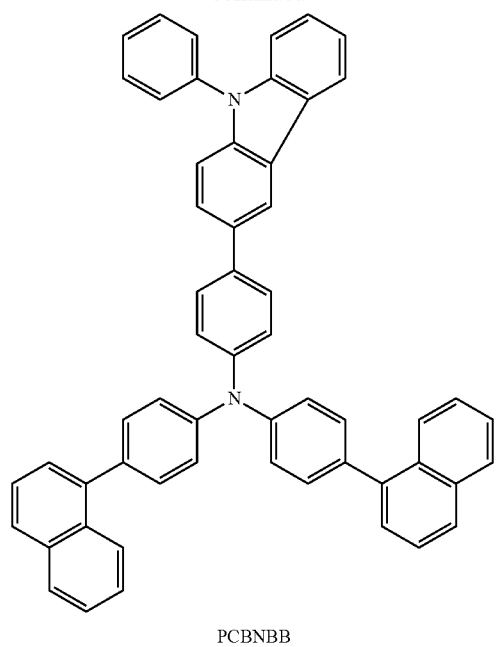
PCBNBB
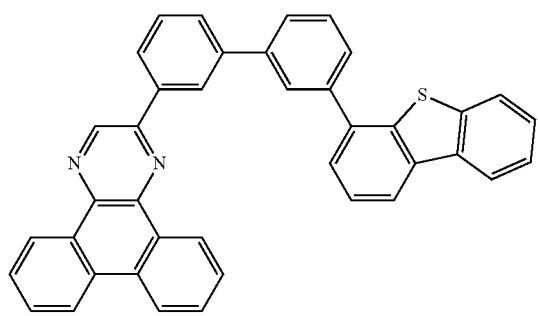
2mDBTBPDBq-II
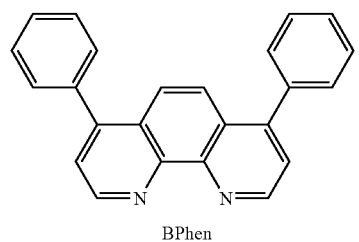
BPhen
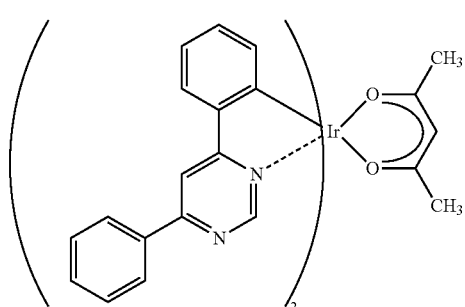
[Ir(dppm)₂(acac)]
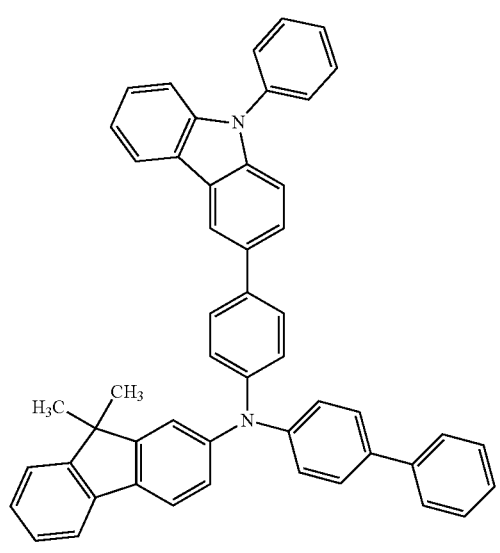
PCBBiF -continued

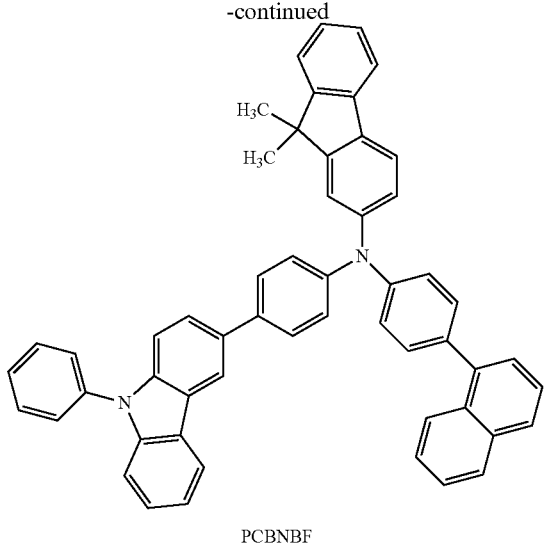

PCBNBF

Methods for manufacturing a light-emitting element 1, a comparative light-emitting element 2, and a comparative light-emitting element 3 of this example will be described below.

(Light-Emitting Element 1)

First, a film of indium tin oxide containing silicon oxide (ITSO) was formed over a glass substrate 1100 by a sputtering method, so that a first electrode 1101 was formed. The thickness thereof was 110 nm and the electrode area was 2 mm×2 mm. Here, the first electrode 1101 functions as an anode of the light-emitting element.

Next, as pretreatment for forming the light-emitting element over the glass substrate 1100, UV-ozone treatment was performed for 370 seconds after washing of a surface of the substrate with water and baking that was performed at 200° C. for 1 hour.

After that, the glass substrate 1100 was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the substrate was cooled down for about 30 minutes.

Then, the glass substrate 1100 over which the first electrode 1101 was formed was fixed to a substrate holder provided in the vacuum evaporation apparatus so that the surface on which the first electrode 1101 was formed faced downward. The pressure in the vacuum evaporation apparatus was reduced to about $10^{-4}$ Pa. After that, over the first electrode 1101, 4,4',4''-(1,3,5-benzenetriyl)tri(dibenzothiophene) (abbreviation: DBT3P-II) and molybdenum(VI) oxide were deposited by co-evaporation by an evaporation method using resistance heating, so that a hole-injection layer 1111 was formed. The thickness of the hole-injection layer 1111 was set to 40 nm, and the weight ratio of DBT3P-II to molybdenum oxide was adjusted to 4:2 (=DBT3P-II:molybdenum oxide). Note that the co-evaporation method refers to an evaporation method in which evaporation is carried out from a plurality of evaporation sources at the same time in one treatment chamber.

Next, a film of 4-phenyl-4'-(9-phenylfluoren-9-yl)triphenylamine (abbreviation: BPAFLP) was formed to a thickness of 20 nm over the hole-injection layer 1111 to form a hole-transport layer 1112.

Further, a light-emitting layer 1113 was formed over the hole-transport layer 1112 by co-evaporation of 2-[3'-(dibenzothiophen-4-yl)biphenyl-3-yl]dibenzo[f,h]quinoxaline (abbreviation: 2mDBTBPDBq-II), N-(1,1'-biphenyl-4-yl)-N-[4-(9-phenyl-9H-carbazol-3-yl)phenyl]-9,9-dimethyl-9H-fluor en-2-amine (abbreviation: PCBBiF), and (acetylacetonato)bis(4,6-diphenylpyrimidinato)iridium(III) (abbreviation: [Ir(dppm)$_2$(acac)]). Here, the weight ratio of 2mDBTBPDBq-II to PCBBiF and [Ir(dppm)$_2$(acac)] was adjusted to 0.8:0.2:0.05 (=2mDBTBPDBq-II:PCBBiF:[Ir(dppm)$_2$(acac)]). The thickness of the light-emitting layer 1113 was set to 40 nm.

Then, an electron-transport layer 1114 was formed over the light-emitting layer 1113 in such a way that a 15 nm thick film of 2mDBTBPDBq-II was formed and a 15 nm thick film of bathophenanthroline (abbreviation: BPhen) was formed.

After that, over the electron-transport layer 1114, a film of lithium fluoride (LiF) was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 1 of this example was fabricated.

Note that in all the above evaporation steps, evaporation was performed by a resistance-heating method.

(Comparative Light-Emitting Element 2)

A light-emitting layer 1113 of the comparative light-emitting element 2 was formed by co-evaporation of 2mDBTBPDBq-II, 4,4'-di(1-naphthyl)-4''-(9-phenyl-9H-carbazol-3-yl)triphenylamine (abbreviation: PCBNBB), and [Ir(dppm)$_2$(acac)]. Here, the weight ratio of 2mDBTBPDBq-II to PCBNBB and [Ir(dppm)$_2$(acac)] was adjusted to 0.8:0.2:0.05 (=2mDBTBPDBq-II:PCBNBB:[Ir(dppm)$_2$(acac)]). The thickness of the light-emitting layer 1113 was set to 40 nm. Components other than the light-emitting layer 1113 were manufactured in a manner similar to that of the light-emitting element 1.

(Comparative Light-Emitting Element 3)

A light-emitting layer 1113 of the comparative light-emitting element 3 was formed by co-evaporation of 2mDBTBPDBq-II, N-[4-(9-phenyl-9H-carbazol-3-yl)phenyl]-9,9-dimethyl-N-[4-(1-naphthyl)phenyl]-9H-fluoren-2-amine (abbreviation: PCBNBF), and [Ir(dppm)$_2$(acac)]. Here, the weight ratio of 2mDBTBPDBq-II to PCBNBF and [Ir(dppm)$_2$(acac)] was adjusted to 0.8:0.2:0.05 (=2mDBTBPDBq-II:PCBNBF:[Ir(dppm)$_2$(acac)]). The thickness of the light-emitting layer 1113 was set to 40 nm. Components other than the light-emitting layer 1113 were manufactured in a manner similar to that of the light-emitting element 1.

Table 1 shows element structures of the light-emitting elements obtained as described above in this example.

TABLE 1

| | first electrode | hole-injection layer | hole-transport layer | light-emitting layer | electron-transport layer | electron-injection layer | second electrode |
|---|---|---|---|---|---|---|---|
| light-emitting element 1 | ITSO 110 nm | DBT3P-II:MoOx (=4:2) | BPAFLP 20 nm | 2mDBTBPDBq-II:PCBBiF:[Ir(dppm)$_2$(acac)] (=0.8:0.2:0.05) 40 nm | 2mDBTBPDBq-II 15 nm | BPhen 15 nm | LiF 1 nm | Al 200 nm |

TABLE 1-continued

| | first electrode | hole-injection layer | hole-transport layer | light-emitting layer | electron-transport layer | electron-injection layer | second electrode |
|---|---|---|---|---|---|---|---|
| comparative light-emitting element 2 | | 40 nm | | 2mDBTBPDBq-II:PCBNBB:[Ir(dppm)$_2$(acac)] (=0.8:0.2:0.05) 40 nm | | | |
| comparative light-emitting element 3 | | | | 2mDBTBPDBq-II:PCBNBF:[Ir(dppm)$_2$(acac)] (=0.8:0.2:0.05) 40 nm | | | |

The light-emitting element 1, the comparative light-emitting element 2, and the comparative light-emitting element 3 were each sealed using a glass substrate in a glove box containing a nitrogen atmosphere so as not to be exposed to the air. Then, operational characteristics of these light-emitting elements were measured. Note that the measurements were carried out at room temperature (in an atmosphere kept at 25° C.).

Figure 8:
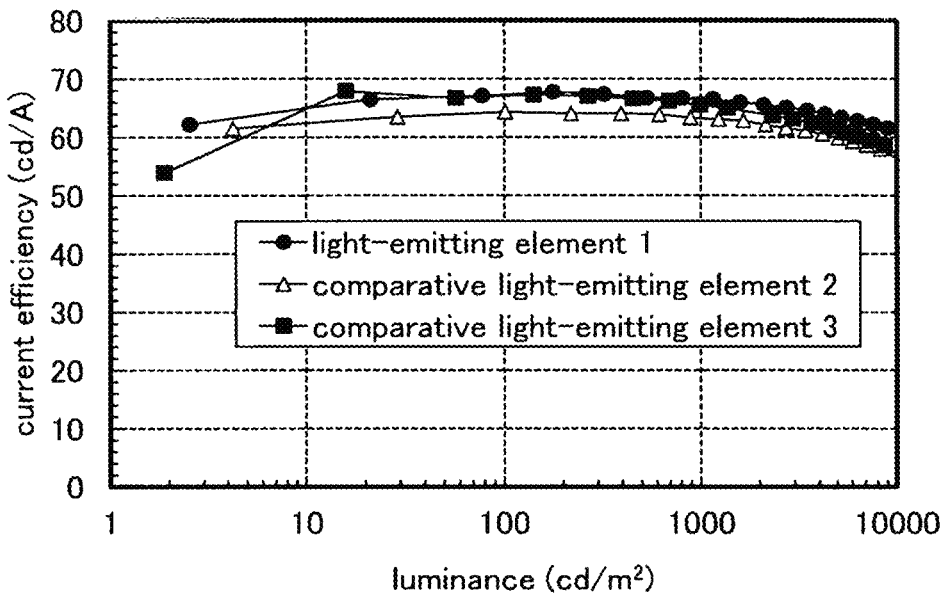
FIG. 8 shows luminance-current efficiency characteristics of light-emitting elements in Example 1.
Figure 9:
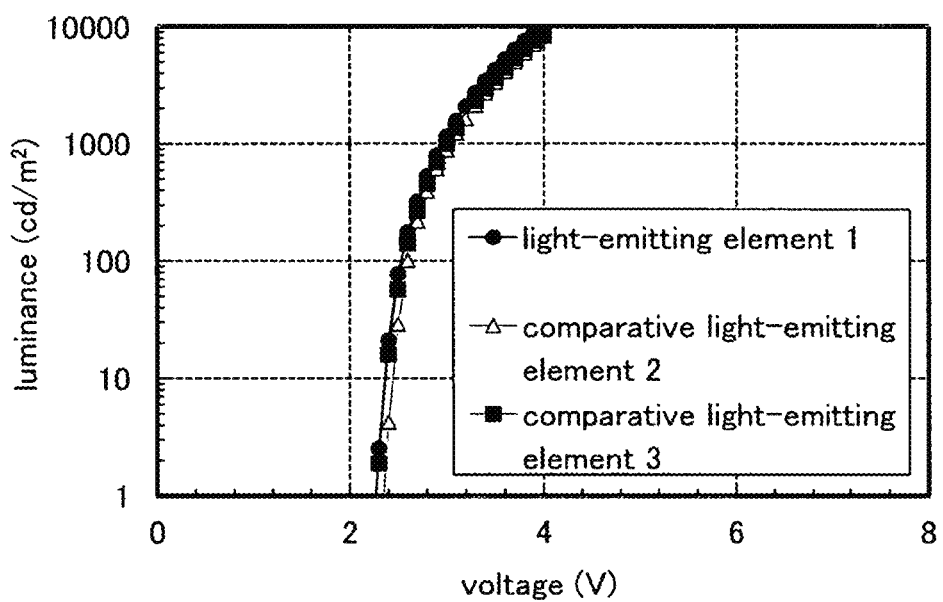
FIG. 9 shows voltage-luminance characteristics of the light-emitting elements in Example 1.
Figure 10:
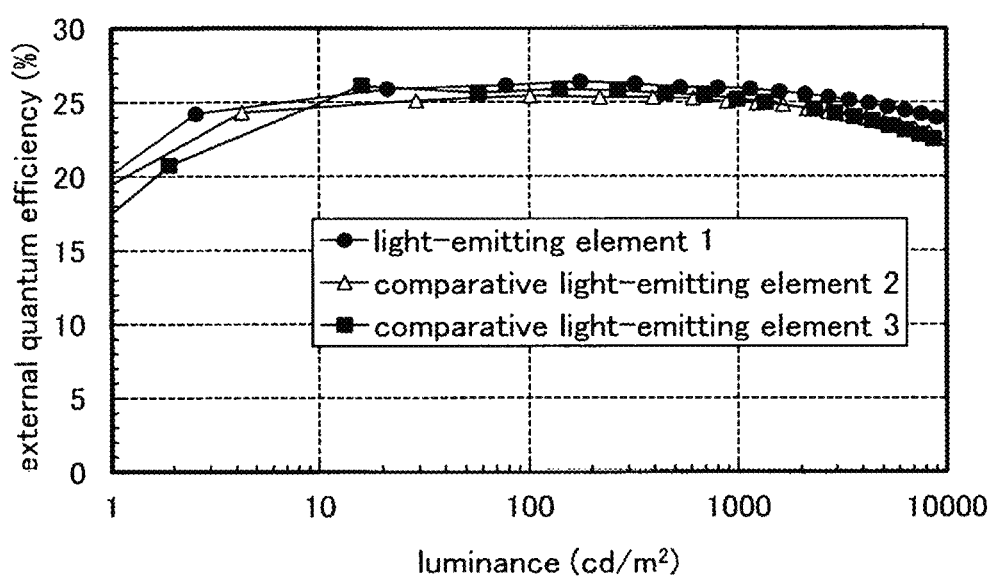
FIG. 10 shows luminance-external quantum efficiency characteristics of the light-emitting elements in Example 1.

FIG. 8 shows luminance-current efficiency characteristics of the light-emitting elements of this example. In FIG. 8, the horizontal axis represents luminance (cd/m$^2$), and the vertical axis represents current efficiency (cd/A). FIG. 9 shows voltage-luminance characteristics. In FIG. 9, the horizontal axis represents voltage (V), and the vertical axis represents luminance (cd/m$^2$). FIG. 10 shows luminance-external quantum efficiency characteristics. In FIG. 10, the horizontal axis represents luminance (cd/m$^2$), and the vertical axis represents external quantum efficiency (%). Table 2 shows the voltage (V), current density (mA/cm$^2$), CIE chromaticity coordinates (x, y), current efficiency (cd/A), power efficiency (lm/W), and external quantum efficiency (%) of each of the light-emitting elements at a luminance of around 1000 cd/m$^2$.

TABLE 2

| | voltage (V) | current density (mA/cm$^2$) | chromaticity x | chromaticity y | luminance (cd/m$^2$) | current efficiency (cd/A) | power efficiency (lm/W) | external quantum efficiency (%) |
|---|---|---|---|---|---|---|---|---|
| light-emitting element 1 | 3.0 | 1.7 | 0.55 | 0.45 | 1200 | 67 | 70 | 26 |
| comparative light-emitting element 2 | 3.0 | 1.4 | 0.55 | 0.44 | 900 | 63 | 66 | 25 |
| comparative light-emitting element 3 | 3.0 | 1.5 | 0.55 | 0.45 | 1000 | 66 | 69 | 25 |

As shown in Table 2, the CIE chromaticity coordinates of the light-emitting element 1 at a luminance of 1200 cd/m$^2$ were (x, y)=(0.55, 0.45). The CIE chromaticity coordinates of the comparative light-emitting element 2 at a luminance of 900 cd/m$^2$ were (x, y)=(0.55, 0.44). The CIE chromaticity coordinates of the comparative light-emitting element 3 at a luminance of 1000 cd/m$^2$ were (x, y)=(0.55, 0.45). It has been found that orange light emission originating from [Ir(dppm)$_2$(acac)] was obtained from the light-emitting elements of this example.

FIGS. 8 to 10 and Table 2 show that the light-emitting element 1, the comparative light-emitting element 2, and the comparative light-emitting element 3 can each be driven at low voltage and have high current efficiency, high power efficiency, and high external quantum efficiency.

It has also been found that the current efficiency and the external quantum efficiency in a high luminance region are higher in the light-emitting element 1 than in the comparative light-emitting element 2 and the comparative light-emitting element 3 (see the current efficiency or the external quantum efficiency at a luminance of 1000 cd/m$^2$ to 10000 cd/m$^2$ in FIG. 8 or FIG. 10). In the light-emitting element 1, the light-emitting layer contains PCBBiF which has a fluorenyl group, a biphenyl group, and a substituent including a carbazole skeleton. In the comparative light-emitting element 2, the light-emitting layer contains PCBNBB which has two naphthyl groups and a substituent including a carbazole skeleton. In the comparative light-emitting element 3, the light-emitting layer contains PCBNBF which has a fluorenyl group, a naphthyl group, and a substituent including a carbazole skeleton. That is, a major difference between the light-emitting element 1 and the comparative light-emitting element 2 or 3 is whether or not the tertiary amine in the light-emitting layer has a naphthyl group. Since the tertiary amine used in the light-emitting element 1 of one embodiment of the present invention has a biphenylamine skeleton and a fluorenylamine skeleton, it has a high hole-transport property and a high electron-blocking property. In addition, since the tertiary amine has a higher triplet excitation energy than an amine including a naphthalene skeleton or the like, it has an excellent exciton-blocking property. Therefore, electron leakage and exciton diffusion can be prevented even in a high luminance region, and thus a light-emitting element exhibiting high emission efficiency can be obtained.

Figure 11A:
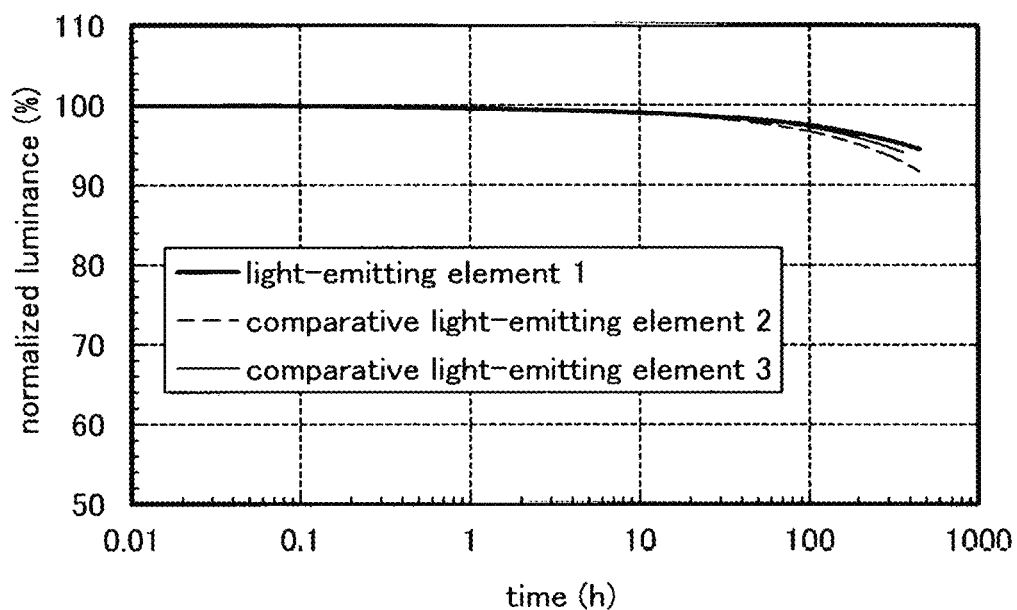
FIGS. 11A and 11B show results of reliability tests of the light-emitting elements in Example 1.
Figure 11B:
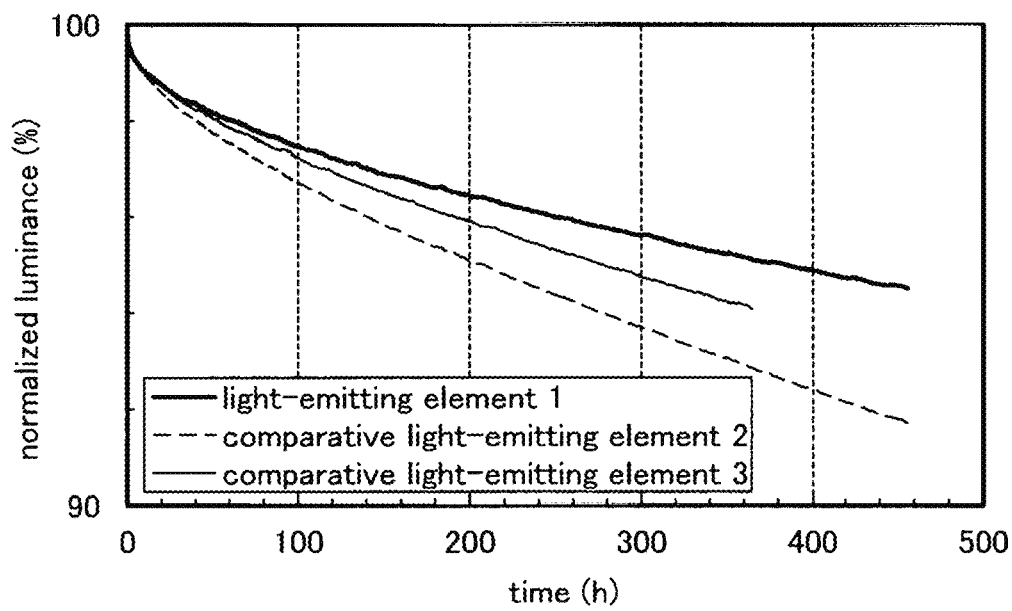

Next, the light-emitting element 1, the comparative light-emitting element 2, and the comparative light-emitting element 3 were subjected to reliability tests. Results of the reliability tests are shown in FIGS. 11A and 11B. In FIGS. 11A and 11B, the vertical axis represents normalized luminance (%) with an initial luminance of 100%, and the horizontal axis represents driving time (h) of the elements. In the reliability tests, the light-emitting elements of this example were driven at room temperature under the conditions where the initial luminance was set to 5000 cd/m$^2$ and the current density was constant. FIGS. 11A and 11B show that the light-emitting element 1 kept 95% of the initial luminance after 460 hours elapsed, the comparative light-emitting element 2 kept 92% of the initial luminance after 460 hours elapsed, and the comparative light-emitting element 3 kept 94% of the initial luminance after 370 hours elapsed. The results of the reliability tests have revealed that the light-emitting element 1 has a longer lifetime than the comparative light-emitting element 2 and the comparative light-emitting element 3.

As described above, in the light-emitting element 1 of one embodiment of the present invention, electron leakage and exciton diffusion can be prevented even in a high luminance region; thus, there are few deactivation pathways (non-radiative deactivation) other than transition by light emission of the light-emitting substance (radiative deactivation). Therefore, luminance degradation of the element can be reduced. In addition, such a light-emitting element with little degradation can be obtained easily and stably with high reproducibility.

As described above, it has been found that a light-emitting element exhibiting high emission efficiency in a high luminance region can be obtained in accordance with one embodiment of the present invention. It has also been found that a light-emitting element having a long lifetime can be obtained in accordance with one embodiment of the present invention.

Example 2

In this example, a light-emitting element of one embodiment of the present invention will be described with reference to FIG. 7. Chemical formulae of materials used in this example are shown below. Note that the chemical formulae of the materials already shown above are omitted.

[Chemical formula 25]

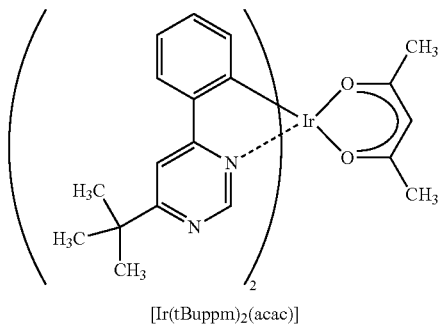

[Ir(tBuppm)₂(acac)]

Methods for manufacturing a light-emitting element 4 and a comparative light-emitting element 5 of this example will be described below.

(Light-Emitting Element 4)

First, in a manner similar to that of the light-emitting element 1, a first electrode 1101 and a hole-injection layer 1111 were formed over a glass substrate 1100.

Next, over the hole-injection layer 1111, a him of PCBBiF was formed to a thickness of 20 nm to form a hole-transport layer 1112.

Further, a light-emitting layer 1113 was formed over the hole-transport layer 1112 by co-evaporation of 2mDBTBPDBq-II, PCBBiF, and (acetylacetonato)bis(6-tert-butyl-4-phenylpyrimidinato)iridium(III) (abbreviation: [Ir(tBuppm)₂(acac)]). Here, a 20 nm thick layer formed with the weight ratio of 2mDBTBPDBq-II to PCBBiF and [Ir(tBuppm)₂(acac)] adjusted to 0.7:0.3:0.05 (=2mDBTBPDBq-II:PCBBiF:[Ir(tBuppm)₂(acac)]) and a 20 nm thick layer formed with the weight ratio of 2mDBTBPDBq-II to PCBBiF and [Ir(tBuppm)₂(acac)] adjusted to 0.8:0.2:0.05 (=2mDBTBPDBq-II:PCBBiF:[Ir(tBuppm)₂(acac)]) were stacked.

Then, an electron-transport layer 1114 was formed over the light-emitting layer 1113 in such a way that a 5 nm thick film of 2mDBTBPDBq-II was formed and a 15 nm thick film of BPhen was formed.

Further, over the electron-transport layer 1114, a film of LiF was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 4 of this example was fabricated.

Note that in all the above evaporation steps, evaporation was performed by a resistance-heating method.

(Comparative Light-Emitting Element 5)

A hole-transport layer 1112 of the comparative light-emitting element 5 was formed by forming a film of PCBNBB to a thickness of 20 nm. A light-emitting layer 1113 was formed by co-evaporation of 2mDBTBPDBq-II, PCBNBB, and [Ir(tBuppm)₂(acac)]. Here, a 20 nm thick layer formed with the weight ratio of 2mDBTBPDBq-II to PCBNBB and [Ir(tBuppm)₂(acac)] adjusted to 0.7:0.3:0.05 (=2mDBTBPDBq-II:PCBNBB:[Ir(tBuppm)₂(acac)]) and a 20 nm thick layer formed with the weight ratio of 2mDBTBPDBq-II to PCBNBB and [Ir(tBuppm)₂(acac)] adjusted to 0.8:0.2:0.05 (=2mDBTBPDBq-II:PCBNBB:[Ir(tBuppm)₂(acac)]) were stacked. Components other than the hole-transport layer 1112 and the light-emitting layer 1113 were manufactured in a manner similar to that of the light-emitting element 4.

Table 3 shows element structures of the light-emitting elements obtained as described above in this example.

TABLE 3

| | first electrode | hole-injection layer | hole-transport layer | light-emitting layer | | | electron-transport layer | electron-injection layer | second electrode |
|---|---|---|---|---|---|---|---|---|---|
| light-emitting element 4 | ITSO 110 nm | DBT3P-II:MoOx (=4:2) 20 nm | PCBBiF 20 nm | 2mDBTBPDBq-II:PCBBiF:[Ir(tBuppm)₂(acac)] (=0.7:0.3:0.05) 20 nm | (=0.8:0.2:0.05) 20 nm | | 2mDBTBPDBq-II 5 nm | BPhen 15 nm | LiF 1 nm | Al 200 nm |
| comparative light-emitting element 5 | | | PCBNBB 20 nm | 2mDBTBPDBq-II:PCBNBB:[Ir(tBuppm)₂(acac)] (=0.7:0.3:0.05) 20 nm | (=0.8:0.2:0.05) 20 nm | | | | | |

The light-emitting element 4 and the comparative light-emitting element 5 were each sealed using a glass substrate in a glove box containing a nitrogen atmosphere so as not to be exposed to the air. Then, operational characteristics of these light-emitting elements were measured. Note that the measurements were carried out at room temperature (in an atmosphere kept at 25° C.).

Figure 12:
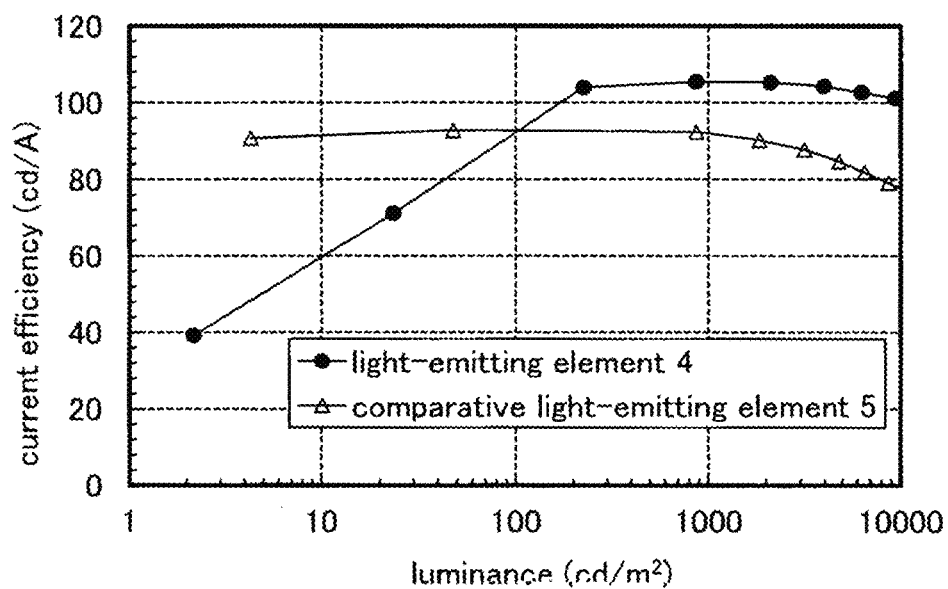
FIG. 12 shows luminance-current efficiency characteristics of light-emitting elements in Example 2.
Figure 13:
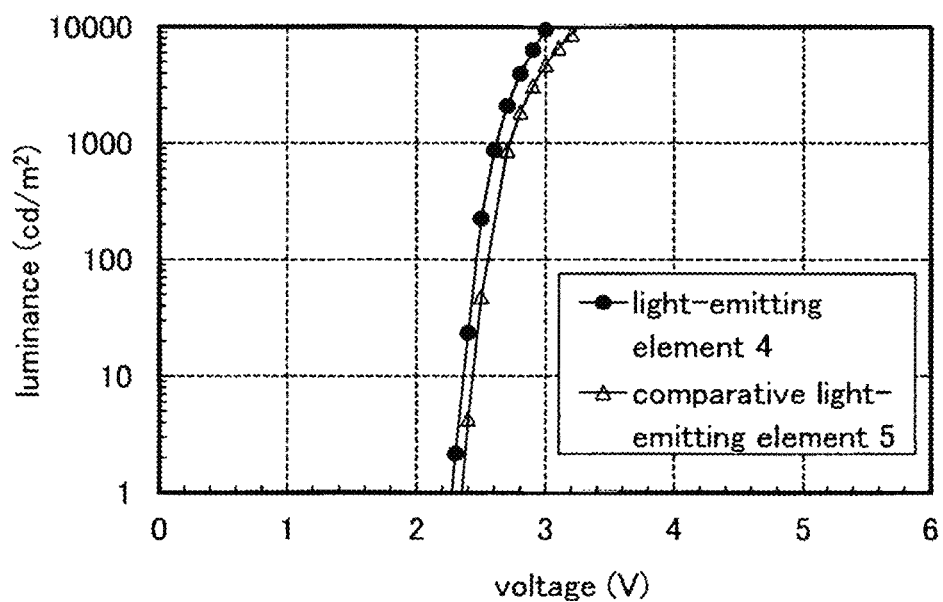
FIG. 13 shows voltage-luminance characteristics of the light-emitting elements in Example 2.
Figure 14:
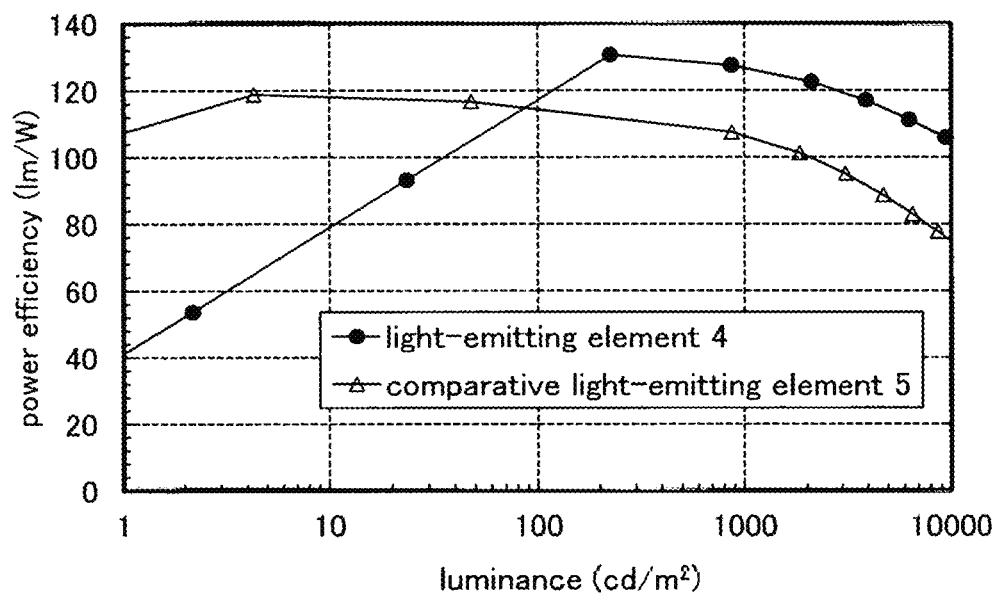
FIG. 14 shows luminance-power efficiency characteristics of the light-emitting elements in Example 2.
Figure 15:
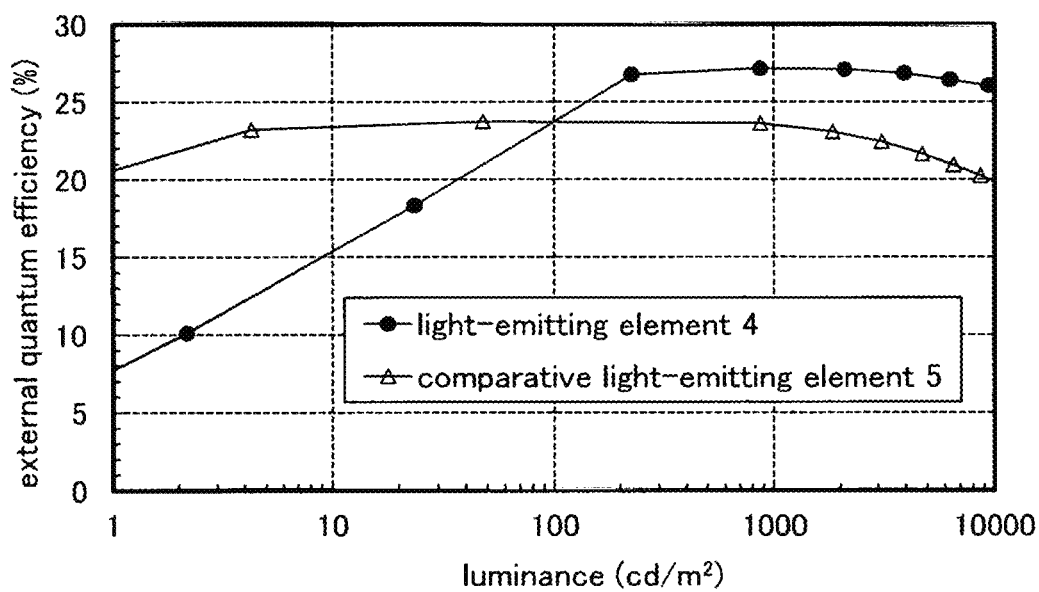
FIG. 15 shows luminance-external quantum efficiency characteristics of the light-emitting elements in Example 2.

FIG. 12 shows luminance-current efficiency characteristics of the light-emitting elements of this example. In FIG. 12, the horizontal axis represents luminance (cd/m$^2$), and the vertical axis represents current efficiency (cd/A). FIG. 13 shows voltage-luminance characteristics. In FIG. 13, the horizontal axis represents voltage (V), and the vertical axis represents luminance (cd/m$^2$). FIG. 14 shows luminance-power efficiency characteristics. In FIG. 14, the horizontal axis represents luminance (cd/m$^2$), and the vertical axis represents power efficiency (lm/W). FIG. 15 shows luminance-external quantum efficiency characteristics. In FIG. 15, the horizontal axis represents luminance (cd/m$^2$), and the vertical axis represents external quantum efficiency (%). Table 4 shows the voltage (V), current density (mA/cm$^2$), CIE chromaticity coordinates (x, y), current efficiency (cd/A), power efficiency (lm/W), and external quantum efficiency (%) of the light-emitting element 4 and the comparative light-emitting element 5 at a luminance of 900 cd/m$^2$.

TABLE 4

| | voltage (V) | current density (mA/cm$^2$) | chromaticity x | chromaticity y | luminance (cd/m$^2$) | current efficiency (cd/A) | power efficiency (lm/W) | external quantum efficiency (%) |
|---|---|---|---|---|---|---|---|---|
| light-emitting element 4 | 2.6 | 0.82 | 0.41 | 0.59 | 900 | 106 | 128 | 27 |
| comparative light-emitting element 5 | 2.7 | 0.94 | 0.40 | 0.59 | 900 | 92 | 108 | 24 |

As shown in Table 4, at a luminance of 900 cd/m$^2$, the CIE chromaticity coordinates of the light-emitting element 4 were (x, y)=(0.41, 0.59), and the CIE chromaticity coordinates of the comparative light-emitting element 5 were (x, y)=(0.40, 0.59). It has been found that green light emission originating from [Ir(tBuppm)$_2$(acac)] was obtained from the light-emitting element 4 and the comparative light-emitting element 5.

FIGS. 12 to 15 and Table 4 show that the light-emitting element 4 and the comparative light-emitting element 5 can each be driven at extremely low voltage. It has also been found that the light-emitting element 4 has higher current efficiency, higher power efficiency, and higher external quantum efficiency than the comparative light-emitting element 5 (see the current efficiency, the power efficiency, or the external quantum efficiency at a luminance of 1000 cd/m$^2$ to 10000 cd/m$^2$ in FIG. 12, FIG. 14, or FIG. 15).

In the light-emitting element 4, the light-emitting layer and the hole-transport layer contain PCBBiF which has a fluorenyl group, a biphenyl group, and a substituent including a carbazole skeleton. In the comparative light-emitting element 5, the light-emitting layer and the hole-transport layer contain PCBNBB which has two naphthyl groups and a substituent including a carbazole skeleton. That is, a major difference between the light-emitting element 4 and the comparative light-emitting element 5 is whether or not the tertiary amine in the light-emitting layer has a naphthyl group. Since the tertiary amine used in the light-emitting element 4 of one embodiment of the present invention has a biphenylamine skeleton and a fluorenylamine skeleton, it has a high hole-transport property and a high electron-blocking property. In addition, since the tertiary amine has a higher triplet excitation energy than an amine including a naphthalene skeleton or the like, it has an excellent exciton-blocking property. Therefore, electron leakage and exciton diffusion can be prevented even in a high luminance region, and thus a light-emitting element exhibiting high emission efficiency can be obtained. The emission efficiency becomes higher when the same compound as the tertiary amine contained in the light-emitting layer is used for the hole-transport layer. That is, although the drive voltage can be decreased by the use of the same compound as the tertiary amine contained in the light-emitting layer for the hole-transport layer as in the light-emitting element 4 and the comparative light-emitting element 5, the emission efficiency is lowered as in the comparative light-emitting element 5 unless one embodiment of the present invention is applied (unless the tertiary amine represented by the above general formula (G0) is used).

As described above, it has been found that a light-emitting element exhibiting high emission efficiency in a high luminance region can be obtained in accordance with one embodiment of the present invention. It has also been found that a light-emitting element which can be driven at low voltage can be obtained in accordance with one embodiment of the present invention. It has been found that a light-emitting element having particularly high emission efficiency can be obtained by the use of the first organic compound (the compound represented by the general formula (G0) shown in Embodiment 1) for a hole-transport layer as well as a light-emitting layer.

Figure 16:
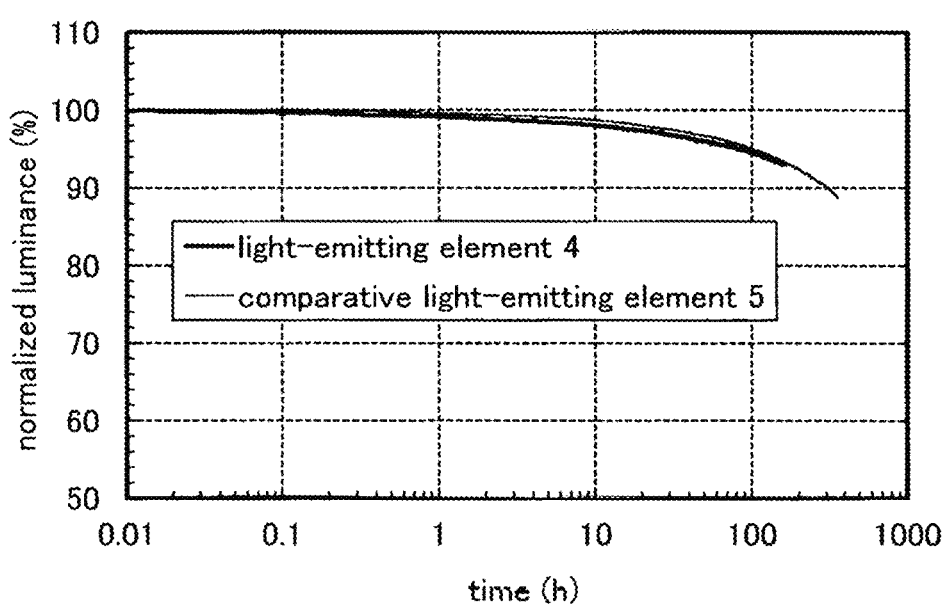
FIG. 16 shows results of reliability tests of the light-emitting elements in Example 2.

Next, the light-emitting element 4 and the comparative light-emitting element 5 were subjected to reliability tests. Results of the reliability tests are shown in FIG. 16. In FIG. 16, the vertical axis represents normalized luminance (%) with an initial luminance of 100%, and the horizontal axis represents driving time (h) of the elements. In the reliability tests, the light-emitting elements of this example were driven at room temperature under the conditions where the initial luminance was set to 5000 cd/m$^2$ and the current density was constant. FIG. 16 shows that the light-emitting element 4 kept 93% of the initial luminance after 160 hours elapsed and the comparative light-emitting element 5 kept 89% of the initial luminance after 360 hours elapsed.

Example 3

In this example, a light-emitting element of one embodiment of the present invention will be described with reference to FIG. 7. Chemical formulae of materials used in this example are shown below. Note that the chemical formulae of the materials already shown above are omitted.

[Chemical formula 26]

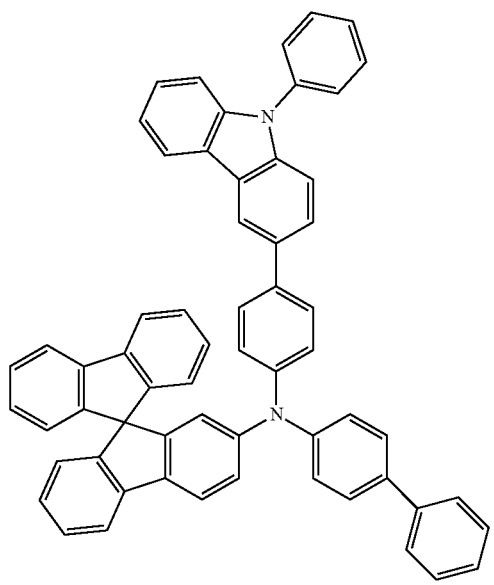

PCBBiSF

Methods for manufacturing a light-emitting element 6 and a light-emitting element 7 of this example will be described below.

(Light-Emitting Element 6)

First, in a manner similar to that of the light-emitting element 1, a first electrode 1101 and a hole-injection layer 1111 were formed over a glass substrate 1100.

Next, over the hole-injection layer 1111, a film of N-(1,1'-biphenyl-4-yl)-N-[4-(9-phenyl-9H-carbazol-3-yl)phenyl]-9,9'-spirobi[9H-fluoren]-2-amine (abbreviation: PCBBiSF) was formed to a thickness of 20 nm to form a hole-transport layer 1112.

Further, a light-emitting layer 1113 was formed over the hole-transport layer 1112 by co-evaporation of 2mDBTBPDBq-II, PCBBiSF, and [Ir(dppm)$_2$(acac)]. Here, a 20 nm thick layer formed with the weight ratio of 2mDBTBPDBq-II to PCBBiSF and [Ir(dppm)$_2$(acac)] adjusted to 0.7:0.3:0.05 (=2mDBTBPDBq-II:PCBBiSF:[Ir(dppm)$_2$(acac)]) and a 20 nm thick layer formed with the weight ratio of 2mDBTBPDBq-II to PCBBiSF and [Ir(dppm)$_2$(acac)] adjusted to 0.8:0.2:0.05 (=2mDBTBPDBq-II:PCBBiSF:[Ir(dppm)$_2$(acac)]) were stacked.

Then, an electron-transport layer 1114 was formed over the light-emitting layer 1113 in such a way that a 20 nm thick film of 2mDBTBPDBq-II was formed and a 20 nm thick film of BPhen was formed.

Further, over the electron-transport layer 1114, a film of LiF was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 6 of this example was fabricated.

Note that in all the above evaporation steps, evaporation was performed by a resistance-heating method.

(Light-Emitting Element 7)

A hole-transport layer 1112 of the light-emitting element 7 was formed by forming a film of BPAFLP to a thickness of 20 nm. Components other than the hole-transport layer 1112 were manufactured in a manner similar to that of the light-emitting element 6.

Table 5 shows element structures of the light-emitting elements obtained as described above in this example.

TABLE 5

| | first electrode | hole-injection layer | hole-transport layer | light-emitting layer | | electron-transport layer | | electron-injection layer | second electrode |
|---|---|---|---|---|---|---|---|---|---|
| light-emitting element 6 | ITSO 110 nm | DBT3P-II:MoOx (=4:2) 20 nm | PCBBiSF 20 nm | 2mDBTBPDBq-II:PCBBiSF:[Ir(dppm)$_2$(acac)] (=0.7:0.3:0.05) 20 nm | (=0.8:0.2:0.05) 20 nm | 2mDBTBPDBq-II 20 nm | BPhen 20 nm | LiF 1 nm | Al 200 nm |
| light-emitting element 7 | | | BPAFLP 20 nm | | | | | | |

The light-emitting element 6 and the light-emitting element 7 were each sealed using a glass substrate in a glove box containing a nitrogen atmosphere so as not to be exposed to the air. Then, operational characteristics of these light-emitting elements were measured. Note that the measurements were carried out at room temperature (in an atmosphere kept at 25° C.).

Figure 17:
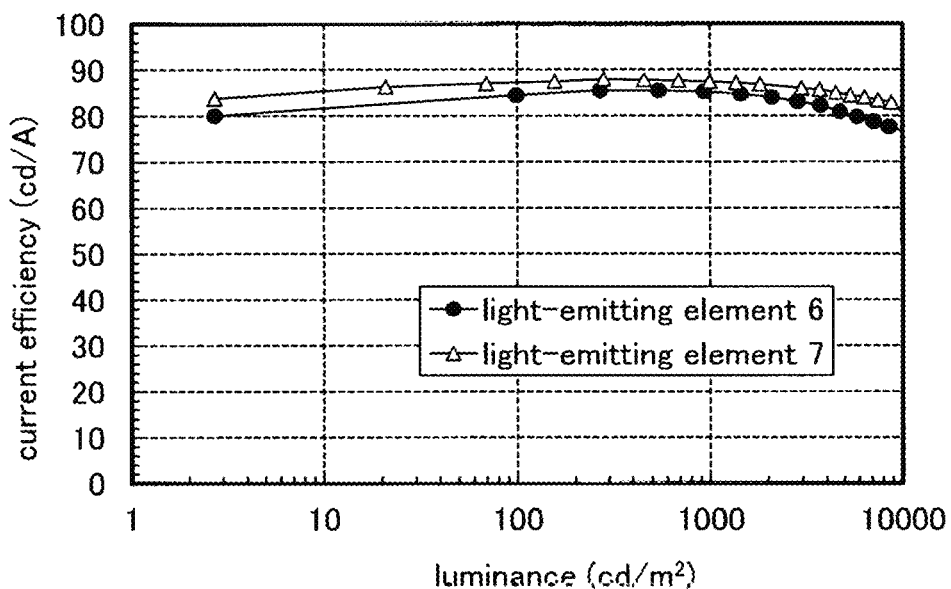
FIG. 17 shows luminance-current efficiency characteristics of light-emitting elements in Example 3.
Figure 18:
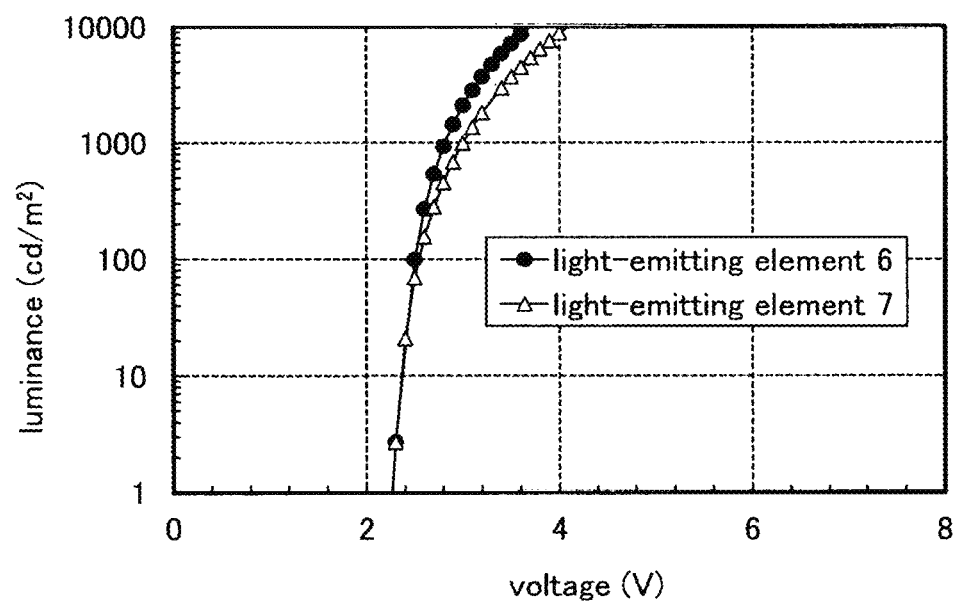
FIG. 18 shows voltage-luminance characteristics of the light-emitting elements in Example 3.
Figure 19:
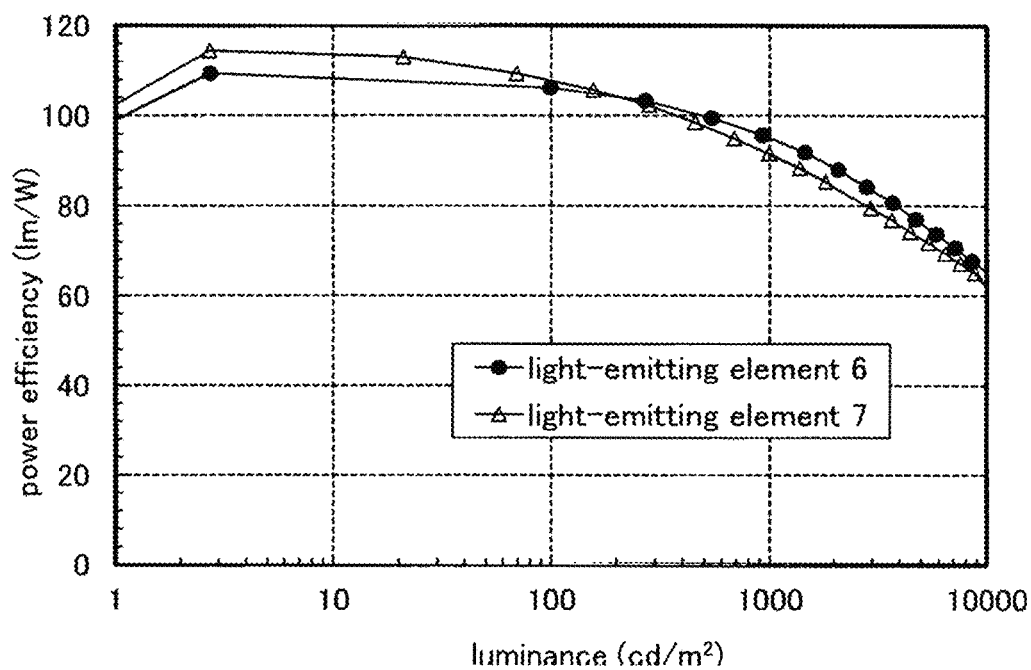
FIG. 19 shows luminance-power efficiency characteristics of the light-emitting elements in Example 3.
Figure 20:
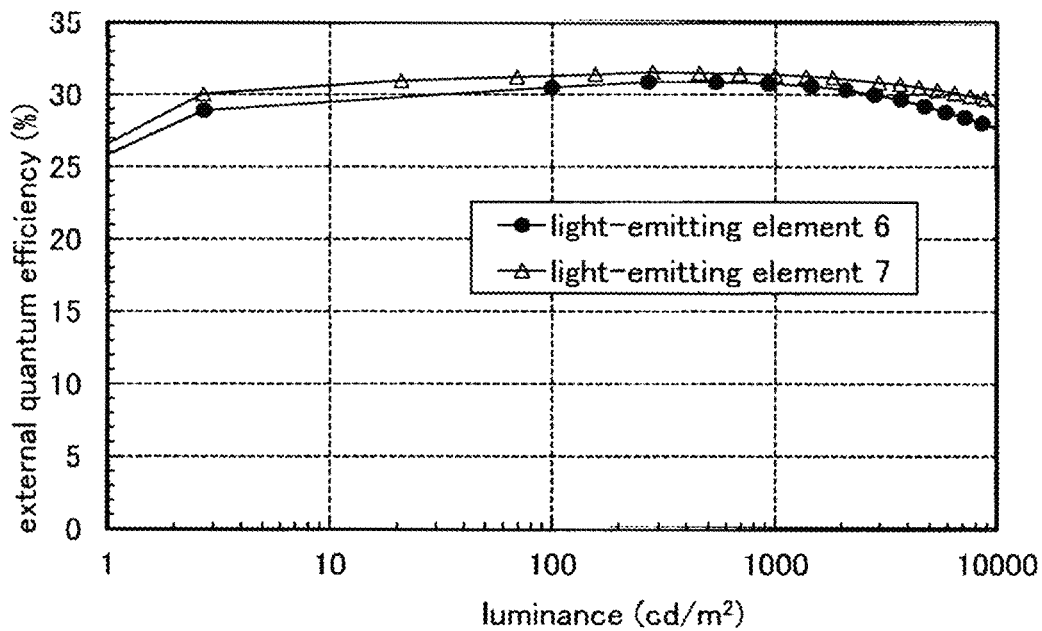
FIG. 20 shows luminance-external quantum efficiency characteristics of the light-emitting elements in Example 3.

FIG. 17 shows luminance-current efficiency characteristics of the light-emitting elements of this example. In FIG. 17, the horizontal axis represents luminance (cd/m$^2$), and the vertical axis represents current efficiency (cd/A). FIG. 18 shows voltage-luminance characteristics. In FIG. 18, the horizontal axis represents voltage (V), and the vertical axis represents luminance (cd/m$^2$). FIG. 19 shows luminance-power efficiency characteristics. In FIG. 19, the horizontal axis represents luminance (cd/m$^2$), and the vertical axis represents power efficiency (lm/W). FIG. 20 shows luminance-external quantum efficiency characteristics. In FIG. 20, the horizontal axis represents luminance (cd/m$^2$), and the vertical axis represents external quantum efficiency (%). Table 6 shows the voltage (V), current density (mA/cm$^2$), CIE chromaticity coordinates (x, y), current efficiency (cd/A), power efficiency (lm/W), and external quantum efficiency (%) of the light-emitting element 6 and the light-emitting element 7 at a luminance of around 1000 cd/m$^2$.

TABLE 6

|  | voltage (V) | current density (mA/cm$^2$) | chromaticity x | chromaticity y | luminance (cd/m$^2$) | current efficiency (cd/A) | power efficiency (lm/W) | external quantum efficiency (%) |
|---|---|---|---|---|---|---|---|---|
| light-emitting element 6 | 2.8 | 1.1 | 0.56 | 0.44 | 900 | 85 | 96 | 31 |
| comparative light-emitting element 7 | 3.0 | 1.1 | 0.55 | 0.44 | 1000 | 87 | 92 | 31 |

As shown in Table 6, the CIE chromaticity coordinates of the light-emitting element 6 at a luminance of 900 cd/m$^2$ were (x, y)=(0.56, 0.44), and the CIE chromaticity coordinates of the light-emitting element 7 at a luminance of 1000 cd/m$^2$ were (x, y)=(0.55, 0.44). It has been found that orange light emission originating from [Ir(dppm)$_2$(acac)] was obtained from the light-emitting element 6 and the light-emitting element 7.

FIGS. 17 to 20 and Table 6 show that the light-emitting element 6 and the light-emitting element 7 can each be driven at low voltage and have high current efficiency, high power efficiency, and high external quantum efficiency. Since the tertiary amine used for the light-emitting layer of each of the light-emitting element 6 and the light-emitting element 7 of one embodiment of the present invention has a biphenylamine skeleton and a spirofluorenylamine skeleton, it has a high hole-transport property and a high electron-blocking property and also an excellent exciton-blocking property. Therefore, electron leakage and exciton diffusion can be prevented even in a high luminance region, and thus a light-emitting element exhibiting high emission efficiency can be obtained. Further, in accordance with one embodiment of the present invention, the drive voltage can be decreased with high emission efficiency maintained (without lowering emission efficiency) by the use of the same compound as the tertiary amine contained in the light-emitting layer for the hole-transport layer as in the light-emitting element 6.

Example 4

In this example, a light-emitting element of one embodiment of the present invention will be described with reference to FIG. 7. Note that chemical formulae of materials used in this example are already shown.

Methods for manufacturing a light-emitting element 8 and a comparative light-emitting element 9 of this example will be described below.

(Light-Emitting Element 8)

First, in a manner similar to that of the light-emitting element 1, a first electrode 1101, a hole-injection layer 1111, and a hole-transport layer 1112 were formed over a glass substrate 1100. The thickness of the hole-injection layer 1111 was set to 20 nm.

Further, a light-emitting layer 1113 was formed over the hole-transport layer 1112 by co-evaporation of 2mDBTBPDBq-II, PCBBiF, and [Ir(dppm)$_2$(acac)]. Here, a 20 nm thick layer formed with the weight ratio of 2mDBTBPDBq-II to PCBBiF and [Ir(dppm)$_2$(acac)] adjusted to 0.7:0.3:0.05 (=2mDBTBPDBq-II:PCBBiF:[Ir(dppm)$_2$(acac)]) and a 20 nm thick layer formed with the weight ratio of 2mDBTBPDBq-II to PCBBiF and [Ir(dppm)$_2$(acac)] adjusted to 0.8:0.2:0.05 (=2mDBTBPDBq-II:PCBBiF:[Ir(dppm)$_2$(acac)]) were stacked.

Then, an electron-transport layer 1114 was formed over the light-emitting layer 1113 in such a way that a 20 nm thick film of 2mDBTBPDBq-II was formed and a 20 nm thick film of BPhen was formed.

After that, over the electron-transport layer 1114, a film of LiF was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 8 of this example was fabricated.

Note that in all the above evaporation steps, evaporation was performed by a resistance-heating method.

(Comparative Light-Emitting Element 9)

A light-emitting layer 1113 of the comparative light-emitting element 9 was formed by co-evaporation of 2mDBTBPDBq-II and [Ir(dppm)$_2$(acac)]. Here, the weight ratio of 2mDBTBPDBq-II to [Ir(dppm)$_2$(acac)] was adjusted to 1:0.05 (=2mDBTBPDBq-II:[Ir(dppm)$_2$(acac)]). The thickness of the light-emitting layer 1113 was set to 40 nm. An electron-transport layer 1114 of the comparative light-emitting element 9 was formed in such a way that a 10 nm thick film of 2mDBTBPDBq-II was formed and furthermore a 15 nm thick film of BPhen was formed. Components other than the light-emitting layer 1113 and the electron-transport layer 1114 were manufactured in a manner similar to that of the light-emitting element 8.

Table 7 shows element structures of the light-emitting elements obtained as described above in this example.

TABLE 7

| | first electrode | hole-injection layer | hole-transport layer | light-emitting layer | | electron-transport layer | electron-injection layer | second electrode |
|---|---|---|---|---|---|---|---|---|
| light-emitting element 8 | ITSO 110 nm | DBT3P-II:MoOx (=4:2) 20 nm | BPAFLP 20 nm | 2mDBTBPDBq-II:PCBBiF:[Ir(dppm)$_2$(acac)] (=0.7:0.3:0.05) 20 nm | (=0.8:0.2:0.05) 20 nm | 2mDBTBPDBq-II 20 nm | BPhen 20 nm | LiF 1 nm | Al 200 nm |
| comparative light-emitting element 9 | | 20 nm | | 2mDBTBPDBq-II:[Ir(dppm)$_2$(acac)] (=1:0.05) 40 nm | | 2mDBTBPDBq-II 10 nm | BPhen 15 nm | | |

The light-emitting element 8 and the comparative light-emitting element 9 were each sealed using a glass substrate in a glove box containing a nitrogen atmosphere so as not to be exposed to the air. Then, operational characteristics of these light-emitting elements were measured. Note that the measurements were carried out at room temperature (in an atmosphere kept at 25° C.).

Figure 27:
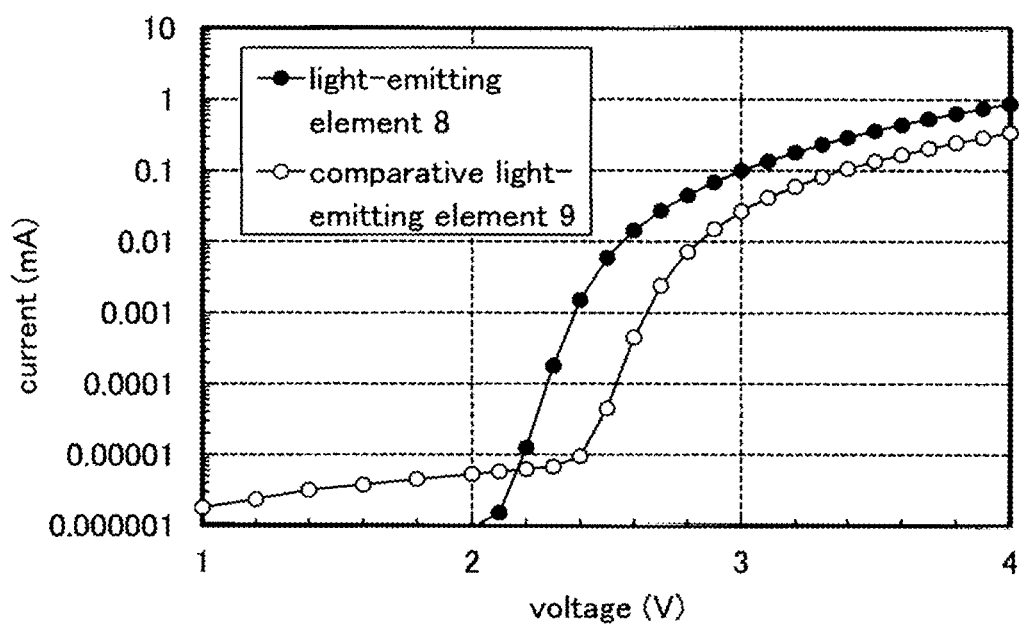
FIG. 27 shows voltage-current characteristics of light-emitting elements in Example 4.
Figure 28:
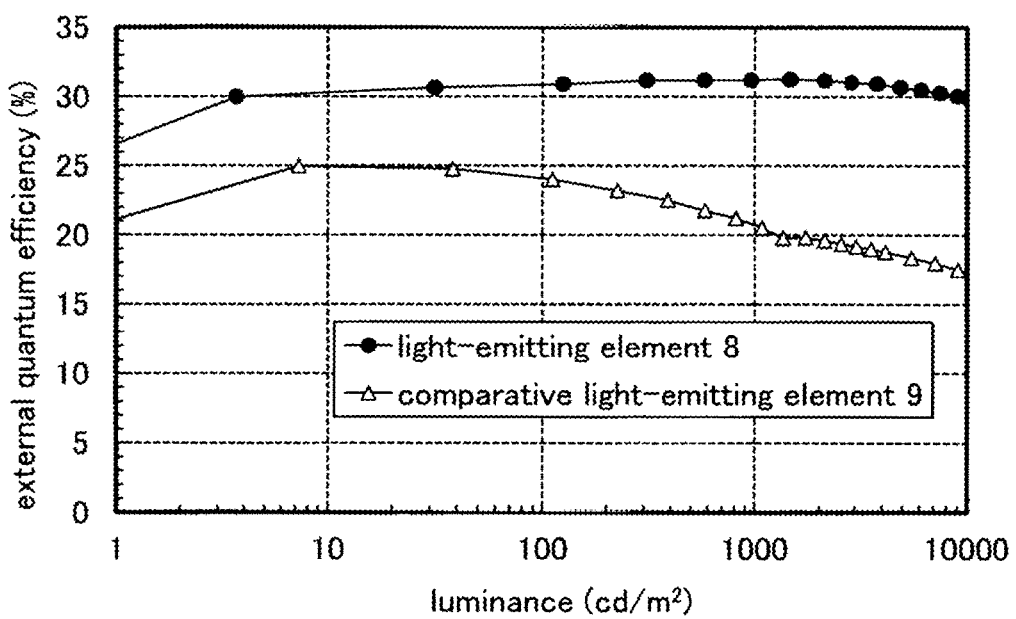
FIG. 28 shows luminance-external quantum efficiency characteristics of the light-emitting elements in Example 4.
Figure 29:
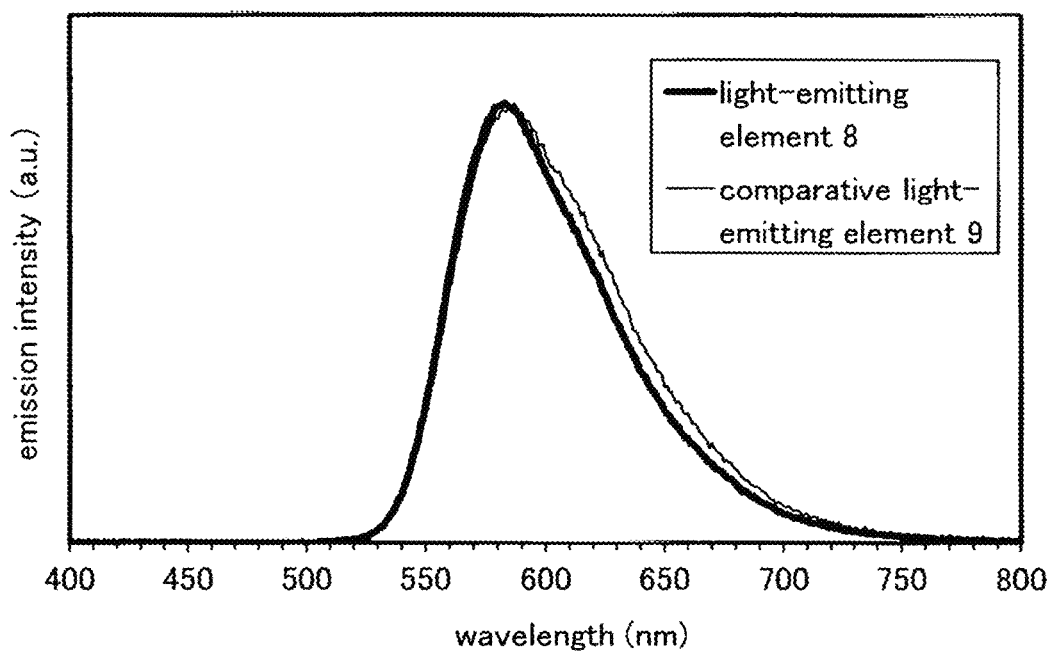
FIG. 29 shows emission spectra of the light-emitting elements in Example 4.

FIG. 27 shows voltage-current characteristics of the light-emitting elements of this example. In FIG. 27, the horizontal axis represents voltage (V), and the vertical axis represents current (mA). FIG. 28 shows luminance-external quantum efficiency characteristics. In FIG. 28, the horizontal axis represents luminance (cd/m$^2$), and the vertical axis represents external quantum efficiency (%). FIG. 29 shows emission spectra of the light-emitting elements of this example. Table 8 shows the voltage (V), current density (mA/cm$^2$), CIE chromaticity coordinates (x, y), current efficiency (cd/A), power efficiency (lm/W), and external quantum efficiency (%) of each of the light-emitting elements at a luminance of around 1000 cd/m$^2$.

TABLE 8

| | voltage (V) | current density (mA/cm$^2$) | chromaticity x | chromaticity y | luminance (cd/m$^2$) | current efficiency (cd/A) | power efficiency (lm/W) | external quantum efficiency (%) |
|---|---|---|---|---|---|---|---|---|
| light-emitting element 8 | 2.8 | 1.1 | 0.56 | 0.44 | 960 | 85 | 95 | 31 |
| comparative light-emitting element 9 | 3.3 | 2.1 | 0.56 | 0.44 | 1100 | 53 | 50 | 21 |

As shown in Table 8, the CIE chromaticity coordinates of the light-emitting element 8 at a luminance of 960 cd/m$^2$ were (x, y)=(0.56, 0.44). The CIE chromaticity coordinates of the comparative light-emitting element 9 at a luminance of 1100 cd/m$^2$ were (x, y)=(0.56, 0.44). It has been found that orange light emission originating from [Ir(dppm)$_2$(acac)] was obtained from the light-emitting elements of this example.

The light-emitting element 8 shows an extremely high external quantum efficiency of 31% (corresponding to a current efficiency of 85 cd/A) at around 1000 cd/m$^2$, which is higher than that of the comparative light-emitting element 9 that does not involve energy transfer from an exciplex.

In addition, the light-emitting element 8 shows an extremely low voltage of 2.8 V at around 1000 cd/m$^2$, and the voltage is lower than that of the comparative light-emitting element 9.

Figure 30:
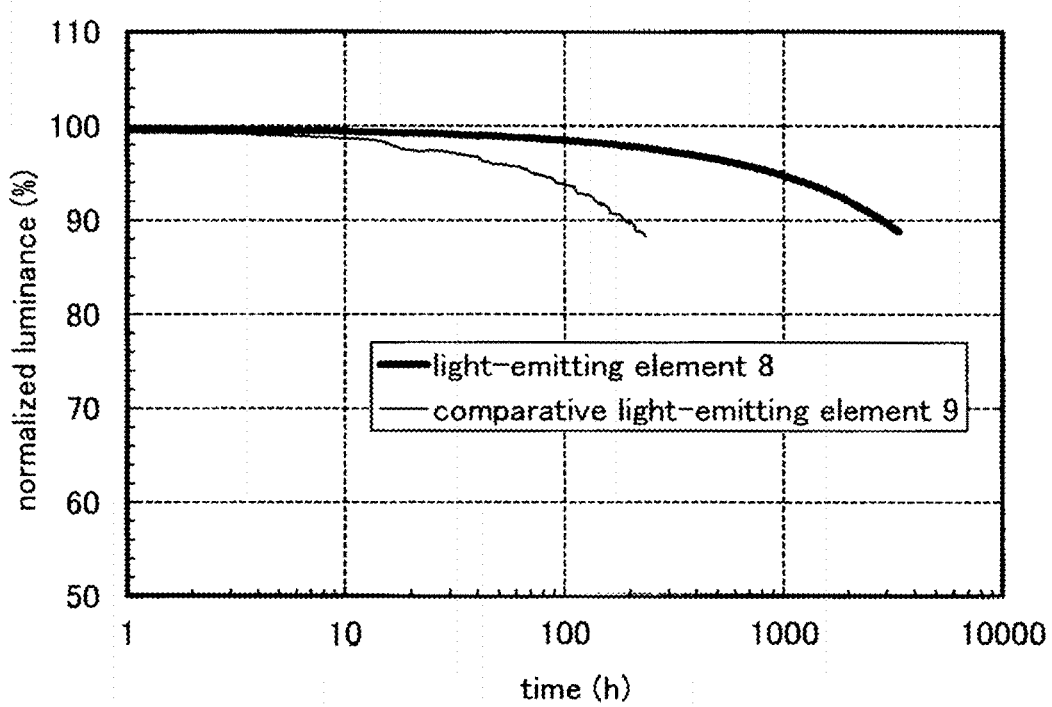
FIG. 30 shows results of reliability tests of the light-emitting elements in Example 4.

Next, the light-emitting element 8 and the comparative light-emitting element 9 were subjected to reliability tests. Results of the reliability tests are shown in FIG. 30. In FIG. 30, the vertical axis represents normalized luminance (%) with an initial luminance of 100%, and the horizontal axis represents driving time (h) of the elements. In the reliability tests, the light-emitting elements of this example were driven at room temperature under the conditions where the initial luminance was set to 5000 cd/m$^2$ and the current density was constant. FIG. 30 shows that the light-emitting element 8 kept 89% of the initial luminance after 3400 hours elapsed and the luminance of the comparative light-emitting element 9 was less than 89% of the initial luminance after 230 hours elapsed. The results of the reliability tests have revealed that the light-emitting element 8 has a longer lifetime than the comparative light-emitting element 9.

As described above, it has been found that a light-emitting element exhibiting high emission efficiency can be obtained in accordance with one embodiment of the present invention. It has also been found that a light-emitting element having a long lifetime can be obtained in accordance with one embodiment of the present invention.

Example 5

In this example, a light-emitting element of one embodiment of the present invention will be described with reference to FIG. 7. Chemical formulae of materials used in this example are shown below. Note that the chemical formulae of the materials already shown above are omitted.

[Chemical formula 27]

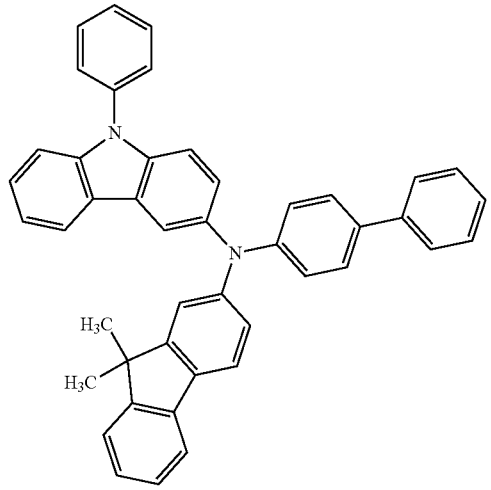

PCBiF

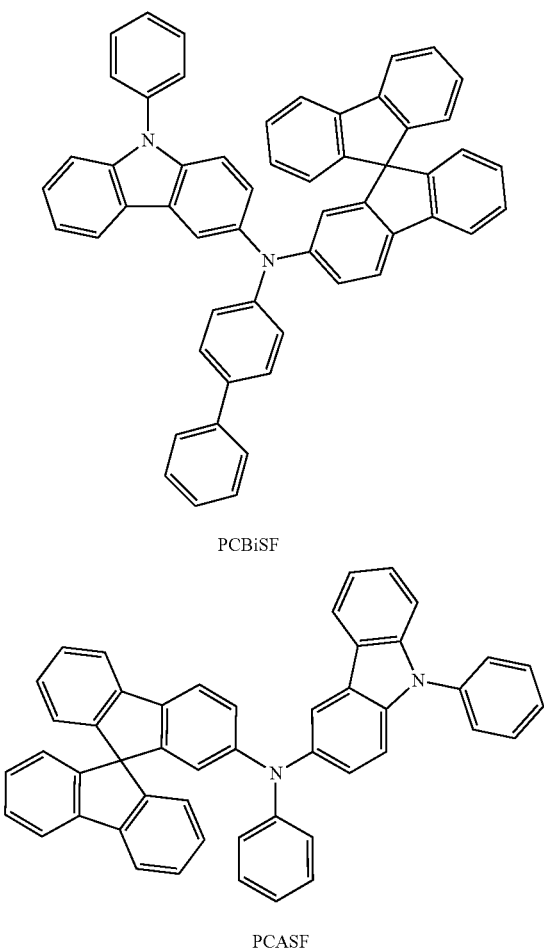

PCBiSF

PCASF dimethyl-9H-fluoren-2-yl)-9-phenyl-9H-carbazol-3-amine (abbreviation: PCBiF), and [Ir(dppm)$_2$(acac)]. Here, a 20 nm thick layer formed with the weight ratio of 2mDBTBPDBq-II to PCBiF and [Ir(dppm)$_2$(acac)] adjusted to 0.7:0.3:0.05 (=2mDBTBPDBq-II:PCBiF:[Ir(dppm)$_2$(acac)]) and a 20 nm thick layer formed with the weight ratio of 2mDBTBPDBq-II to PCBiF and [Ir(dppm)$_2$(acac)] adjusted to 0.8:0.2:0.05 (=2mDBTBPDBq-II:PCBiF:[Ir(dppm)$_2$(acac)]) were stacked.

(Light-Emitting Element 11)

In the light-emitting element 11, a light-emitting layer 1113 was formed over a hole-transport layer 1112 by co-evaporation of 2mDBTBPDBq-II, N-(4-biphenyl)-N-(9,9'-spirobi[9H-fluoren]-2-yl)-9-phenyl-9H-carbazol-3-amine (abbreviation: PCBiSF), and [Ir(dppm)$_2$(acac)]. Here, a 20 nm thick layer formed with the weight ratio of 2mDBTBPDBq-II to PCBiSF and [Ir(dppm)$_2$(acac)] adjusted to 0.7:0.3:0.05 (=2mDBTBPDBq-II:PCBiSF:[Ir(dppm)$_2$(acac)]) and a 20 nm thick layer formed with the weight ratio of 2mDBTBPDBq-II to PCBiSF and [Ir(dppm)$_2$(acac)] adjusted to 0.8:0.2:0.05 (=2mDBTBPDBq-II:PCBiSF:[Ir(dppm)$_2$(acac)]) were stacked.

(Comparative Light-Emitting Element 12)

In the comparative light-emitting element 12, a light-emitting layer 1113 was formed over a hole-transport layer 1112 by co-evaporation of 2mDBTBPDBq-II, 2-[N-(9-phenylcarbazol-3-yl)-N-phenylamino]-spiro-9,9'-bifluorene (abbreviation: PCASF), and [Ir(dppm)$_2$(acac)]. Here, a 20 nm thick layer formed with the weight ratio of 2mDBTBPDBq-II to PCASF and [Ir(dppm)$_2$(acac)] adjusted to 0.7:0.3:0.05 (=2mDBTBPDBq-II:PCASF:[Ir(dppm)$_2$(acac)]) and a 20 nm thick layer formed with the weight ratio of 2mDBTBPDBq-II to PCASF and [Ir(dppm)$_2$(acac)] adjusted to 0.8:0.2:0.05 (=2mDBTBPDBq-II:PCASF:[Ir(dppm)$_2$(acac)]) were stacked.

Table 9 shows element structures of the light-emitting elements obtained as described above in this example.

TABLE 9

| | first electrode | hole-injection layer | hole-transport layer | light-emitting layer | | electron-transport layer | electron-injection layer | second electrode |
|---|---|---|---|---|---|---|---|---|
| light-emitting element 10 | ITSO 110 nm | DBT3P-II:MoOx (=4:2) 20 nm | BPAFLP 20 nm | 2mDBTBPDBq-II:PCBiF:[Ir(dppm)$_2$(acac)] (=0.7:0.3:0.05) 20 nm | (=0.8:0.2:0.05) 20 nm | 2mDBTBPDBq-II 20 nm | BPhen 20 nm | LiF 1 nm | Al 200 nm |
| light-emitting element 11 | | | | 2mDBTBPDBq-II:PCBiSF:[Ir(dppm)$_2$(acac)] (=0.7:0.3:0.05) 20 nm | (=0.8:0.2:0.05) 20 nm | | | | |
| comparative light-emitting element 12 | | | | 2mDBTBPDBq-II:PCASF:[Ir(dppm)$_2$(acac)] (=0.7:0.3:0.05) 20 nm | (=0.8:0.2:0.05) 20 nm | | | | |

Methods for manufacturing a light-emitting element 10, a light-emitting element 11, and a comparative light-emitting element 12 of this example will be described below. Note that components other than a light-emitting layer of each light-emitting element of this example and manufacturing methods thereof are similar to those of the light-emitting element 8; thus, the description is omitted here. The light-emitting layer of each light-emitting element of this example and the manufacturing method thereof will be described below.

(Light-Emitting Element 10)

In the light-emitting element 10, a light-emitting layer 1113 was formed over a hole-transport layer 1112 by co-evaporation of 2mDBTBPDBq-II, N-(4-biphenyl)-N-(9,9-

The light-emitting element 10, the light-emitting element 11, and the comparative light-emitting element 12 were each sealed using a glass substrate in a glove box containing a nitrogen atmosphere so as not to be exposed to the air. Then, operational characteristics of these light-emitting elements were measured. Note that the measurements were carried out at room temperature (in an atmosphere kept at 25° C.).

Figure 31:
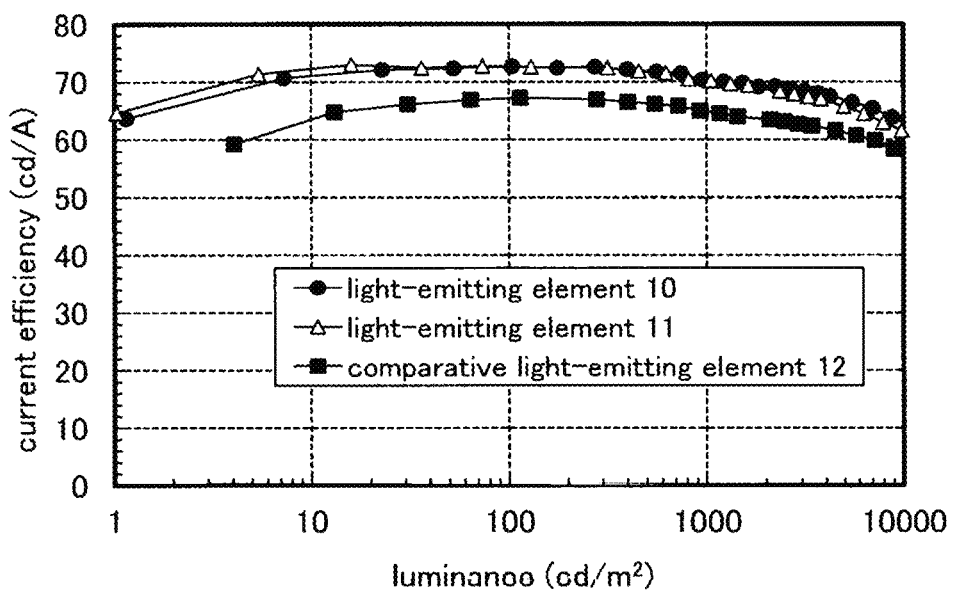
FIG. 31 shows luminance-current efficiency characteristics of light-emitting elements in Example 5.
Figure 32:
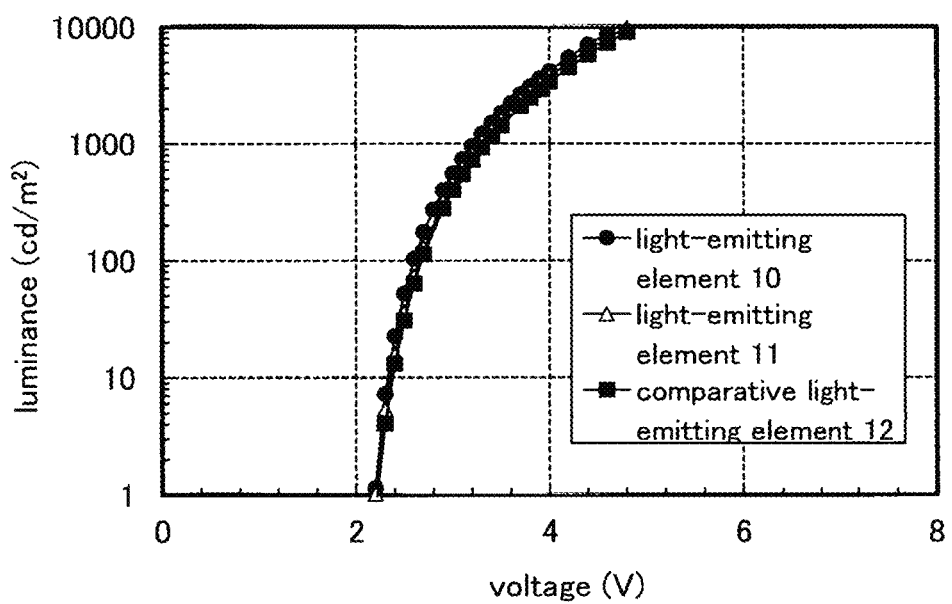
FIG. 32 shows voltage-luminance characteristics of the light-emitting elements in Example 5.
Figure 33:
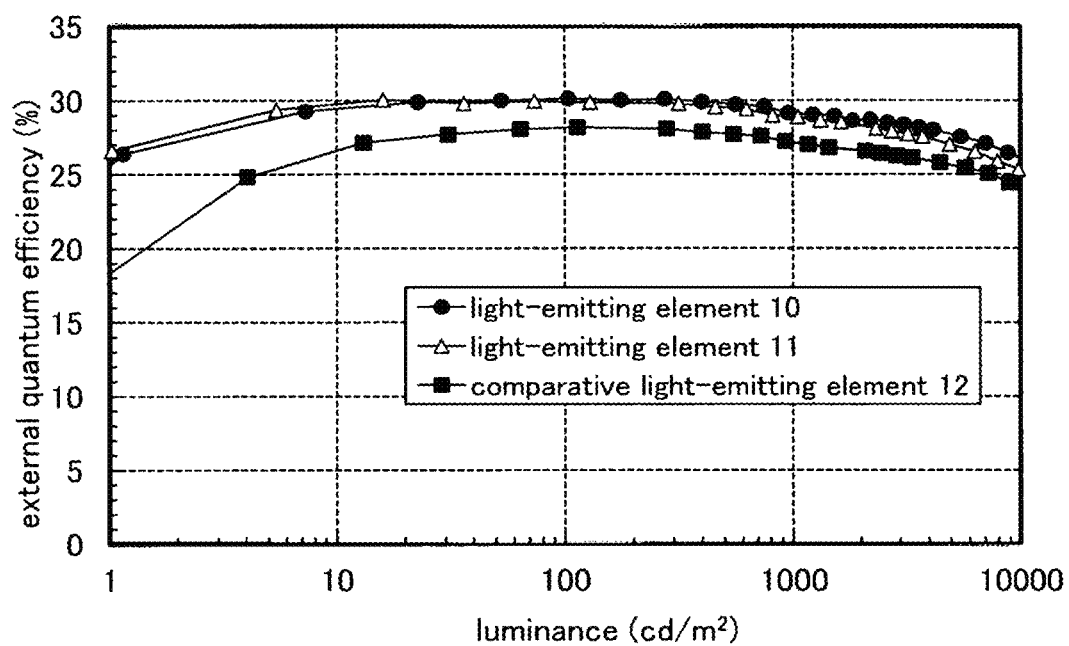
FIG. 33 shows luminance-external quantum efficiency characteristics of the light-emitting elements in Example 5.

FIG. 31 shows luminance-current efficiency characteristics of the light-emitting elements of this example. In FIG. 31, the horizontal axis represents luminance (cd/m$^2$), and the vertical axis represents current efficiency (cd/A). FIG. 32 shows voltage-luminance characteristics. In FIG. 32, the horizontal axis represents voltage (V), and the vertical axis represents luminance (cd/m$^2$). FIG. 33 shows luminance-external quantum efficiency characteristics. In FIG. 33, the horizontal axis represents luminance (cd/m$^2$), and the vertical axis represents external quantum efficiency (%). Further, Table 10 shows the voltage (V), current density (mA/cm$^2$), CIE chromaticity coordinates (x, y), current efficiency (cd/A), power efficiency (lm/W), and external quantum efficiency (%) of each of the light-emitting elements at a luminance of around 1000 cd/m$^2$.

TABLE 10

| | voltage (V) | current density (mA/cm$^2$) | chromaticity x | chromaticity y | luminance (cd/m$^2$) | current efficiency (cd/A) | power efficiency (lm/W) | external quantum efficiency (%) |
|---|---|---|---|---|---|---|---|---|
| light-emitting element 10 | 3.2 | 1.4 | 0.57 | 0.43 | 960 | 70 | 69 | 29 |
| light-emitting element 11 | 3.3 | 1.5 | 0.57 | 0.43 | 1000 | 70 | 67 | 29 |
| comparative light-emitting element 12 | 3.3 | 1.4 | 0.57 | 0.43 | 930 | 65 | 62 | 27 |

As shown in Table 10, the CIE chromaticity coordinates of each light-emitting element at a luminance of around 1000 cd/m$^2$ were (x, y)=(0.57, 0.43). It has been found that orange light emission originating from [Ir(dppm)$_2$(acac)] was obtained from the light-emitting elements of this example.

FIG. 32 and Table 10 show that the light-emitting element 10, the light-emitting element 11, and the comparative light-emitting element 12 are driven at comparable voltages. FIG. 31, FIG. 33, and Table 10 show that the light-emitting element 10 and the light-emitting element 11 have higher current efficiency, higher power efficiency, and higher external quantum efficiency than the comparative light-emitting element 12.

Figure 34:
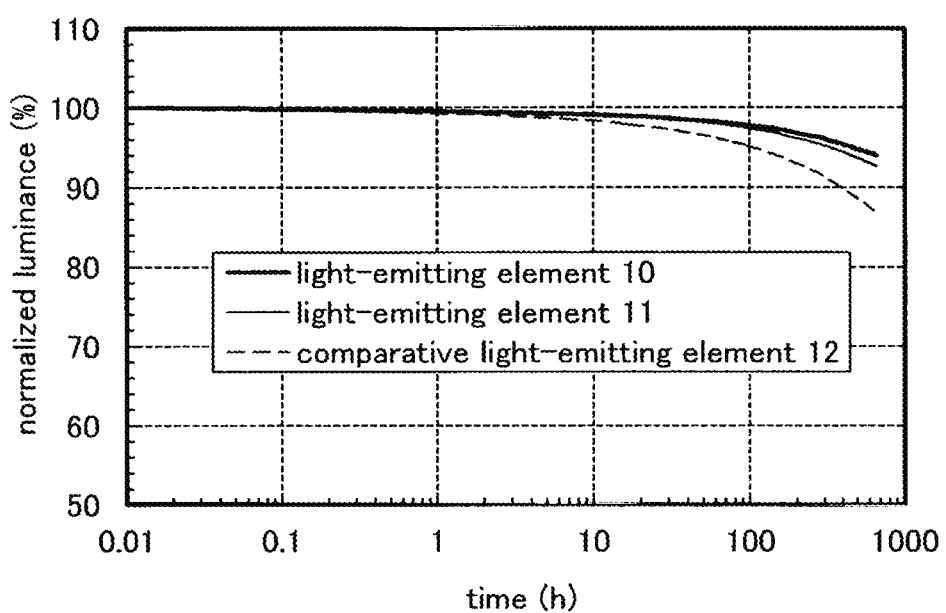
FIG. 34 shows results of reliability tests of the light-emitting elements in Example 5.

Next, the light-emitting element 10, the light-emitting element 11, and the comparative light-emitting element 12 were subjected to reliability tests. Results of the reliability tests are shown in FIG. 34. In FIG. 34, the vertical axis represents normalized luminance (%) with an initial luminance of 100%, and the horizontal axis represents driving time (h) of the elements. In the reliability tests, the light-emitting elements of this example were driven at room temperature under the conditions where the initial luminance was set to 5000 cd/m$^2$ and the current density was constant. FIG. 34 shows that the light-emitting element 10 kept 94% of the initial luminance after 660 hours elapsed, the light-emitting element 11 kept 93% of the initial luminance after 660 hours elapsed, and the luminance of the comparative light-emitting element 12 was less than 87% of the initial luminance after 660 hours elapsed. The results of the reliability tests have revealed that the light-emitting element 10 and the light-emitting element 11 have a longer lifetime than the comparative light-emitting element 12.

In the light-emitting element 11, the light-emitting layer contains PCBiSF which has a spirofluorenyl group, a biphenyl group, and a substituent including a carbazole skeleton. In the comparative light-emitting element 12, the light-emitting layer contains PCASF which has a spirofluorenyl group, a phenyl group, and a substituent including a carbazole skeleton. That is, the only difference between the light-emitting element 11 and the comparative light-emitting element 12 is whether the substituent of the tertiary amine contained in the light-emitting layer is a biphenyl group or a phenyl group. The tertiary amine used in the light-emitting element 11 of one embodiment of the present invention forms a p-biphenylamine skeleton in which the 4-position of the phenyl group of the highly reactive phenylamine skeleton is capped with the phenyl group. Thus, a highly reliable light-emitting element can be obtained.

As described above, it has been found that a light-emitting element exhibiting high emission efficiency can be obtained in accordance with one embodiment of the present invention. It has also been found that a light-emitting element having a long lifetime can be obtained in accordance with one embodiment of the present invention.

Example 6

In this example, a light-emitting element of one embodiment of the present invention will be described with reference to FIG. 7. Note that chemical formulae of materials used in this example are already shown.

Methods for manufacturing a light-emitting element 13, a light-emitting element 14, a light-emitting element 15, and a comparative light-emitting element 16 of this example will be described below. Note that components other than a light-emitting layer and an electron-transport layer of each light-emitting element of this example and manufacturing methods thereof are similar to those of the light-emitting element 8; thus, the description is omitted here. The light-emitting layer and the electron-transport layer of each light-emitting element of this example and the manufacturing method thereof will be described below.

(Light-Emitting Element 13)

In the light-emitting element 13, a light-emitting layer 1113 was formed over a hole-transport layer 1112 by co-evaporation of 2mDBTBPDBq-II, PCBBiF, and [Ir(tBuppm)$_2$(acac)]. Here, a 20 nm thick layer formed with the weight ratio of 2mDBTBPDBq-II to PCBBiF and [Ir(tBuppm)$_2$(acac)] adjusted to 0.7:0.3:0.05 (=2mDBTBPDBq-II:PCBBiF:[Ir(tBuppm)$_2$(acac)]) and a 20 nm thick layer formed with the weight ratio of 2mDBTBPDBq-II to PCBBiF and [Ir(tBuppm)$_2$(acac)] adjusted to 0.8:0.2:0.05 (=2mDBTBPDBq-II:PCBBiF:[Ir(tBuppm)$_2$(acac)]) were stacked.

(Light-Emitting Element 14)

In the light-emitting element 14, a light-emitting layer 1113 was formed over a hole-transport layer 1112 by co-evaporation of 2mDBTBPDBq-II, PCBiF, and [Ir(tBuppm)$_2$(acac)]. Here, a 20 nm thick layer formed with the weight ratio of 2mDBTBPDBq-II to PCBiF and [Ir(tBuppm)$_2$(acac)] adjusted to 0.7:0.3:0.05 (=2mDBTBPDBq-II:PCBiF:[Ir(tBuppm)$_2$(acac)]) and a 20 nm thick layer formed with the weight ratio of 2mDBTBPDBq-II to PCBiF and [Ir(tBuppm)$_2$(acac)] adjusted to 0.8:0.2:0.05 (=2mDBTBPDBq-II:PCBiF:[Ir(tBuppm)$_2$(acac)]) were stacked.

(Light-Emitting Element 15)

In the light-emitting element 15, a light-emitting layer 1113 was formed over a hole-transport layer 1112 by co-evaporation of 2mDBTBPDBq-II, PCBiSF, and [Ir(tBuppm)$_2$(acac)]. Here, a 20 nm thick layer formed with the weight ratio of 2mDBTBPDBq-II to PCBiSF and [Ir(tBuppm)$_2$(acac)] adjusted to 0.7:0.3:0.05 (=2mDBTBPDBq-II:PCBiSF:[Ir(tBuppm)$_2$(acac)]) and a 20 nm thick layer formed with the weight ratio of 2mDBTBPDBq-II to PCBiSF and [Ir(tBuppm)$_2$(acac)] adjusted to 0.8:0.2:0.05 (=2mDBTBPDBq-II:PCBiSF:[Ir(tBuppm)$_2$(acac)]) were stacked.

(Comparative Light-Emitting Element 16)

In the comparative light-emitting element 16, a light-emitting layer 1113 was formed over a hole-transport layer 1112 by co-evaporation of 2mDBTBPDBq-II, PCASF, and [Ir(tBuppm)$_2$(acac)]. Here, a 20 nm thick layer formed with the weight ratio of 2mDBTBPDBq-II to PCASF and [Ir(tBuppm)$_2$(acac)] adjusted to 0.7:0.3:0.05 (=2mDBTBPDBq-II:PCASF:[Ir(tBuppm)$_2$(acac)]) and a 20 nm thick layer formed with the weight ratio of 2mDBTBPDBq-II to PCASF and [Ir(tBuppm)$_2$(acac)] adjusted to 0.8:0.2:0.05 (=2mDBTBPDBq-II:PCASF:[Ir(tBuppm)$_2$(acac)]) were stacked.

Further, in each of the light-emitting element 13, the light-emitting element 14, the light-emitting element 15, and the comparative light-emitting element 16, an electron-transport layer 1114 was formed over the light-emitting layer 1113 in such a way that a 10 nm thick film of 2mDBTBPDBq-II was formed and a 15 nm thick film of BPhen was formed.

Table 11 shows element structures of the light-emitting elements obtained as described above in this example.

TABLE 11

| | first electrode | hole-injection layer | hole-transport layer | light-emitting layer | | electron-transport layer | | electron-injection layer | second electrode |
|---|---|---|---|---|---|---|---|---|---|
| light-emitting element 13 | ITSO 110 nm | DBT3P-II:MoOx (=4:2) 20 nm | BPAFLP 20 nm | 2mDBTBPDBq-II:PCBBiF:[Ir(tBuppm)$_2$(acac)] (=0.7:0.3:0.05) 20 nm | (=0.8:0.2:0.05) 20 nm | 2mDBTBPDBq-II 10 nm | BPhen 15 nm | LiF 1 nm | Al 200 nm |
| light-emitting element 14 | | | | 2mDBTBPDBq-II:PCBiF:[Ir(tBuppm)$_2$(acac)] (=0.7:0.3:0.05) 20 nm | (=0.8:0.2:0.05) 20 nm | | | | |
| light-emitting element 15 | | | | 2mDBTBPDBq-II:PCBiSF:[Ir(tBuppm)$_2$(acac)] (=0.7:0.3:0.05) 20 nm | (=0.8:0.2:0.05) 20 nm | | | | |
| comparative light-emitting element 16 | | | | 2mDBTBPDBq-II:PCaSF:[Ir(tBuppm)$_2$(acac)] (=0.7:0.3:0.05) 20 nm | (=0.8:0.2:0.05) 20 nm | | | | |

The light-emitting element 13, the light-emitting element 14, the light-emitting element 15, and the comparative light-emitting element 16 were each sealed using a glass substrate in a glove box containing a nitrogen atmosphere so as not to be exposed to the air. Then, operational characteristics of these light-emitting elements were measured. Note that the measurements were carried out at room temperature (in an atmosphere kept at 25° C.).

Figure 35:
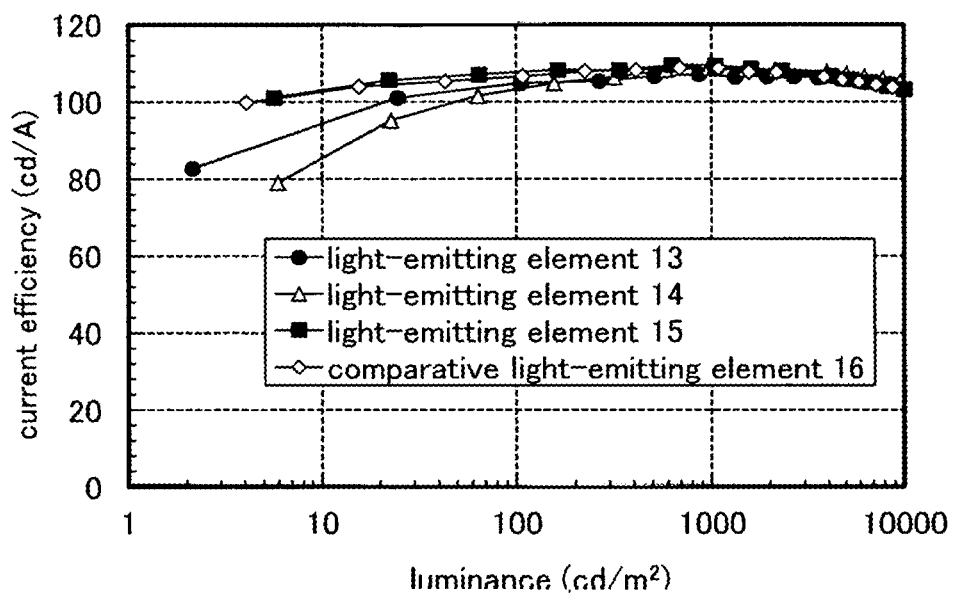
FIG. 35 shows luminance-current efficiency characteristics of light-emitting elements in Example 6.
Figure 36:
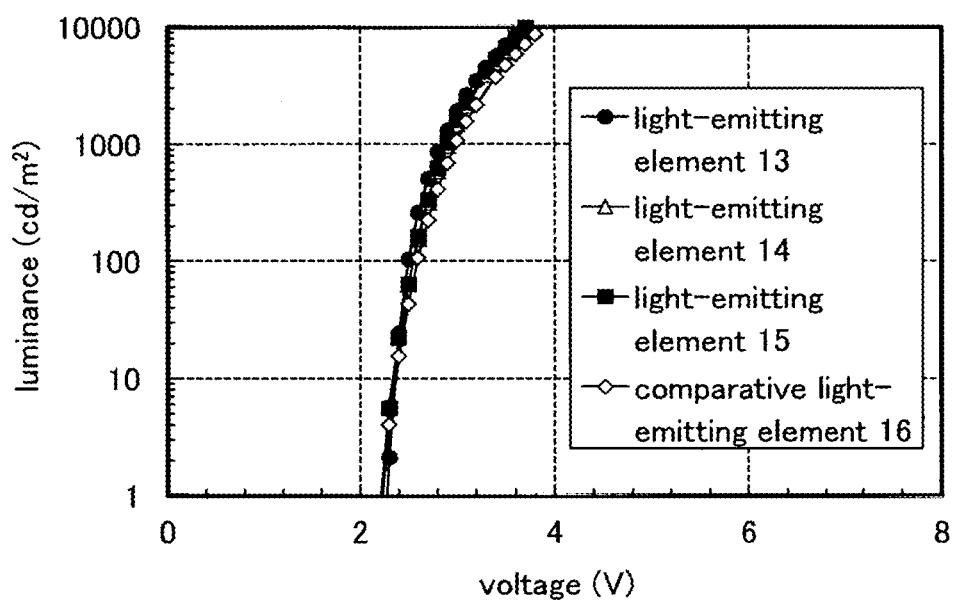
FIG. 36 shows voltage-luminance characteristics of the light-emitting elements in Example 6.
Figure 37:
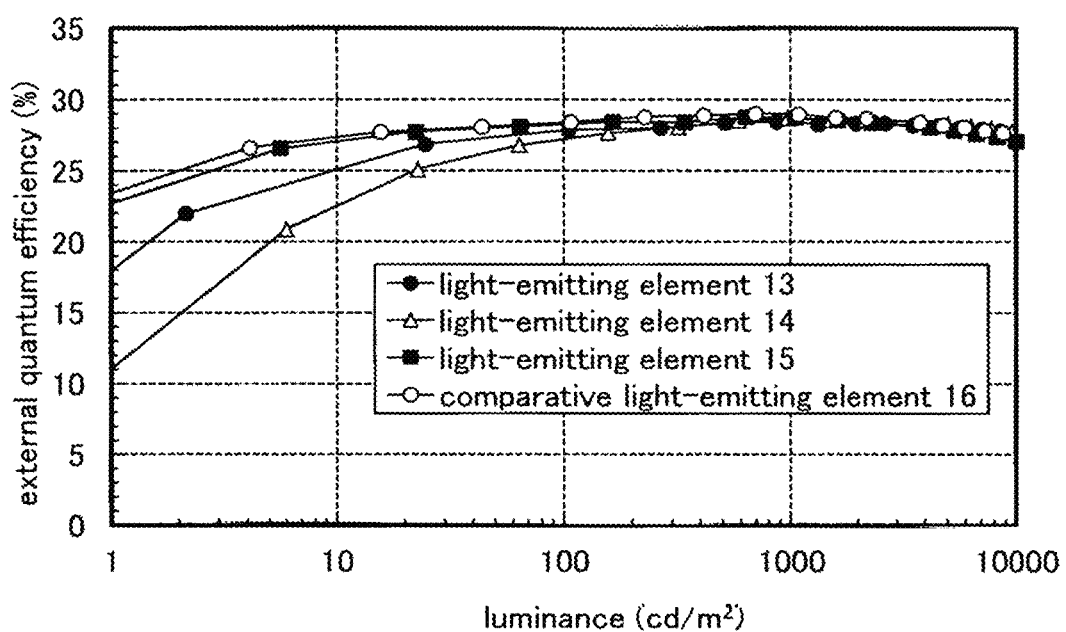
FIG. 37 shows luminance-external quantum efficiency characteristics of the light-emitting elements in Example 6.

FIG. 35 shows luminance-current efficiency characteristics of the light-emitting elements of this example. In FIG. 35, the horizontal axis represents luminance (cd/m$^2$), and the vertical axis represents current efficiency (cd/A). FIG. 36 shows voltage-luminance characteristics. In FIG. 36, the horizontal axis represents voltage (V), and the vertical axis represents luminance (cd/m$^2$). FIG. 37 shows luminance-external quantum efficiency characteristics. In FIG. 37, the horizontal axis represents luminance (cd/m$^2$), and the vertical axis represents external quantum efficiency (%). Further, Table 12 shows the voltage (V), current density (mA/cm$^2$), CIE chromaticity coordinates (x, y), current efficiency (cd/A), power efficiency (lm/W), and external quantum efficiency (%) of each light-emitting element at a luminance of around 1000 cd/m$^2$.

TABLE 12

| | voltage (V) | current density (mA/cm$^2$) | chromaticity | | luminance (cd/m$^2$) | current efficiency (cd/A) | power efficiency (lm/W) | external quantum efficiency (%) |
|---|---|---|---|---|---|---|---|---|
| | | | x | y | | | | |
| light-emitting element 13 | 2.8 | 0.80 | 0.41 | 0.58 | 860 | 107 | 120 | 28 |
| light-emitting element 14 | 2.9 | 0.89 | 0.41 | 0.58 | 970 | 109 | 118 | 29 |

TABLE 12-continued

| | voltage (V) | current density (mA/cm$^2$) | chromaticity x | chromaticity y | luminance (cd/m$^2$) | current efficiency (cd/A) | power efficiency (lm/W) | external quantum efficiency (%) |
|---|---|---|---|---|---|---|---|---|
| light-emitting element 15 | 2.9 | 0.95 | 0.42 | 0.57 | 1000 | 109 | 119 | 29 |
| comparative light-emitting element 16 | 3.0 | 0.10 | 0.42 | 0.57 | 1100 | 109 | 114 | 29 |

As shown in Table 12, the CIE chromaticity coordinates of the light-emitting element 13 at a luminance of 860 cd/m$^2$ were (x, y)=(0.41, 0.58). The CIE chromaticity coordinates of the light-emitting element 14 at a luminance of 970 cd/m$^2$ were (x, y)=(0.41, 0.58). The CIE chromaticity coordinates of the light-emitting element 15 at a luminance of 1000 cd/m$^2$ were (x, y)=(0.42, 0.57). The CIE chromaticity coordinates of the comparative light-emitting element 16 at a luminance of 1100 cd/m$^2$ were (x, y)=(0.42, 0.57). It has been found that yellow-green light emission originating from [Ir(tBuppm)$_2$(acac)] was obtained from the light-emitting elements of this example.

FIGS. 35 to 37 and Table 12 show that the light-emitting element 13, the light-emitting element 14, the light-emitting element 15, and the comparative light-emitting element 16 can each be driven at low voltage and have high current efficiency, high power efficiency, and high external quantum efficiency.

Figure 38:
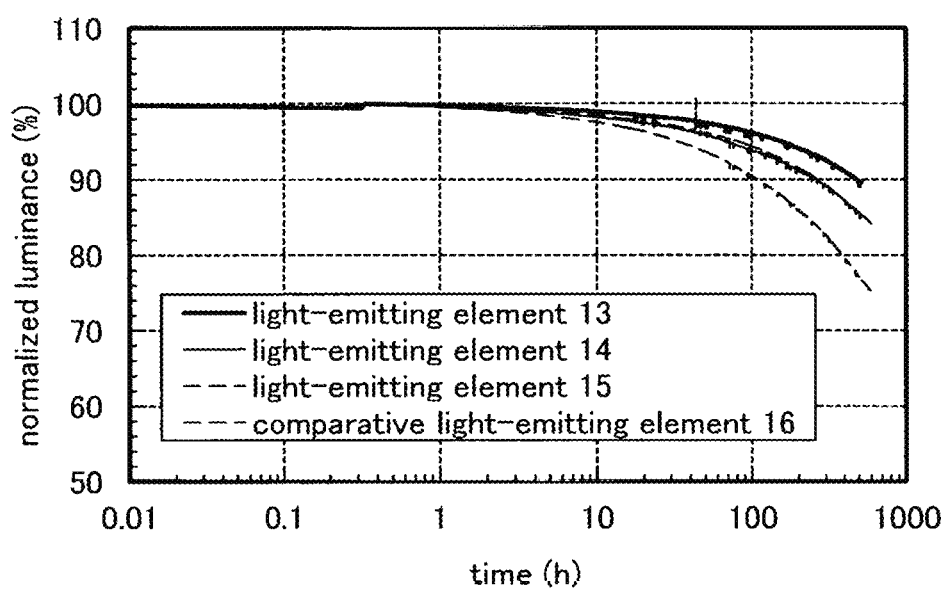
FIG. 38 shows results of reliability tests of the light-emitting elements in Example 6.

Next, the light-emitting element 13, the light-emitting element 14, the light-emitting element 15, and the comparative light-emitting element 16 were subjected to reliability tests. Results of the reliability tests are shown in FIG. 38. In FIG. 38, the vertical axis represents normalized luminance (%) with an initial luminance of 100%, and the horizontal axis represents driving time (h) of the elements. In the reliability tests, the light-emitting elements of this example were driven at room temperature under the conditions where the initial luminance was set to 5000 cd/m$^2$ and the current density was constant. FIG. 38 shows that the light-emitting element 13 kept 90% of the initial luminance after 520 hours elapsed, the light-emitting element 14 kept 84% of the initial luminance after 600 hours elapsed, the light-emitting element 15 kept 85% of the initial luminance after 520 hours elapsed, and the luminance of the comparative light-emitting element 16 was less than 75% of the initial luminance after 600 hours elapsed. The results of the reliability tests have revealed that the light-emitting element 13, the light-emitting element 14, and the light-emitting element 15 have a longer lifetime than the comparative light-emitting element 16.

As described above, the light-emitting element 15 kept 85% of the initial luminance after 520 hours elapsed, but the luminance of the comparative light-emitting element 16 is less than 77% of the initial luminance after 520 hours elapsed. In the light-emitting element 15, the light-emitting layer contains PCBiSF which has a spirofluorenyl group, a biphenyl group, and a substituent including a carbazole skeleton. In the comparative light-emitting element 16, the light-emitting layer contains PCASF which has a spirofluorenyl group, a phenyl group, and a substituent including a carbazole skeleton. That is, the only difference between the light-emitting element 15 and the comparative light-emitting element 16 is whether the substituent of the tertiary amine contained in the light-emitting layer is a biphenyl group or a phenyl group. The tertiary amine used in the light-emitting element 15 of one embodiment of the present invention forms a p-biphenylamine skeleton in which the 4-position of the phenyl group of the highly reactive phenylamine skeleton is capped with the phenyl group. Thus, a highly reliable light-emitting element can be obtained.

As described above, it has been found that a light-emitting element exhibiting high emission efficiency can be obtained in accordance with one embodiment of the present invention. It has also been found that a light-emitting element having a long lifetime can be obtained in accordance with one embodiment of the present invention.

Example 7

In this example, a light-emitting element of one embodiment of the present invention will be described with reference to FIG. 7. Chemical formulae of materials used in this example are shown below. Note that the chemical formulae of the materials already shown above are omitted.

[Chemical formula 28]

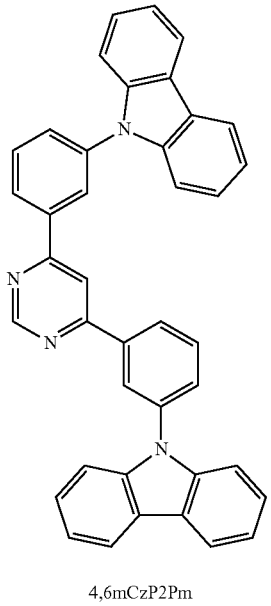

4,6mCzP2Pm

A method for manufacturing a light-emitting element 17 of this example will be described below.
(Light-Emitting Element 17)

First, in a manner similar to that of the light-emitting element 8, a first electrode 1101, a hole-injection layer 1111, and a hole-transport layer 1112 were formed over a glass substrate 1100.

Next, a light-emitting layer 1113 was formed over the hole-transport layer 1112 by co-evaporation of 4,6-bis[3-(9H-carbazol-9-yl)phenyl]pyrimidine (abbreviation: 4,6mCzP2Pm), PCBBiF, and [Ir(tBuppm)$_2$(acac)]. Here, a 20 nm thick layer formed with the weight ratio of 4,6mCzP2Pm to PCBBiF and [Ir(tBuppm)$_2$(acac)] adjusted to 0.7:0.3:0.05 (=4,6mCzP2Pm:PCBBiF:[Ir(tBuppm)$_2$(acac)]) and a 20 nm thick layer formed with the weight ratio of 4,6mCzP2Pm to PCBBiF and [Ir(tBuppm)$_2$(acac)] adjusted to 0.8:0.2:0.05 (=4,6mCzP2Pm:PCBBiF:[Ir(tBuppm)$_2$(acac)]) were stacked.

Then, an electron-transport layer 1114 was formed over the light-emitting layer 1113 in such a way that a 15 nm thick film of 4,6mCzP2Pm was formed and a 10 nm thick film of BPhen was formed.

After that, over the electron-transport layer 1114, a film of LiF was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 17 of this example was fabricated.

Note that in all the above evaporation steps, evaporation was performed by a resistance-heating method.

Table 13 shows an element structure of the light-emitting element obtained as described above in this example.

As shown in Table 14, the CIE chromaticity coordinates of the light-emitting element 17 at a luminance of 760 cd/m$^2$ were (x, y)=(0.41, 0.58). It has been found that orange light emission originating from [Ir(tBuppm)$_2$(acac)] was obtained from the light-emitting element of this example.

Figure 39:
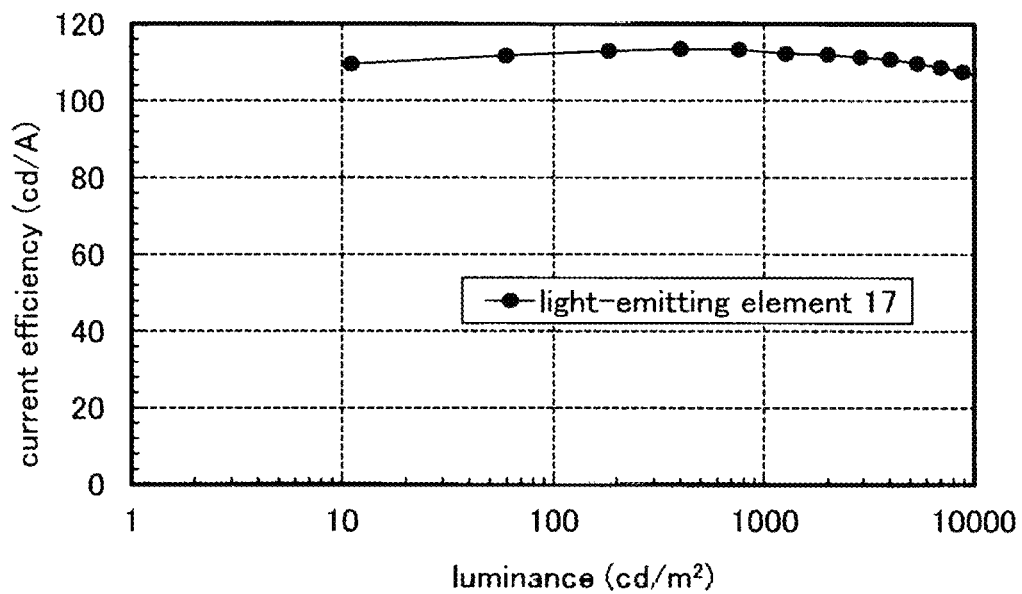
FIG. 39 shows luminance-current efficiency characteristics of a light-emitting element in Example 7.
Figure 40:
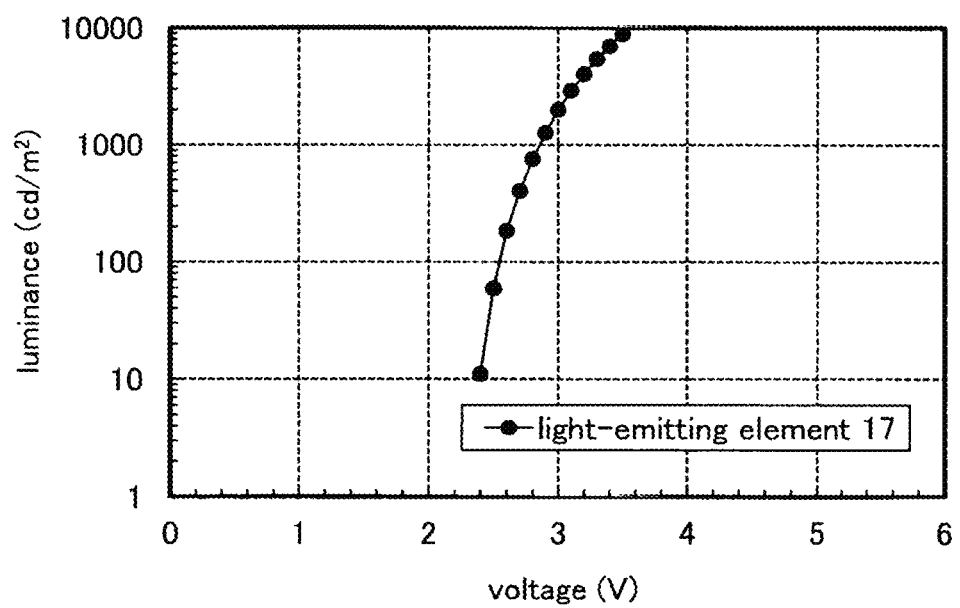
FIG. 40 shows voltage-luminance characteristics of the light-emitting element in Example 7.
Figure 41:
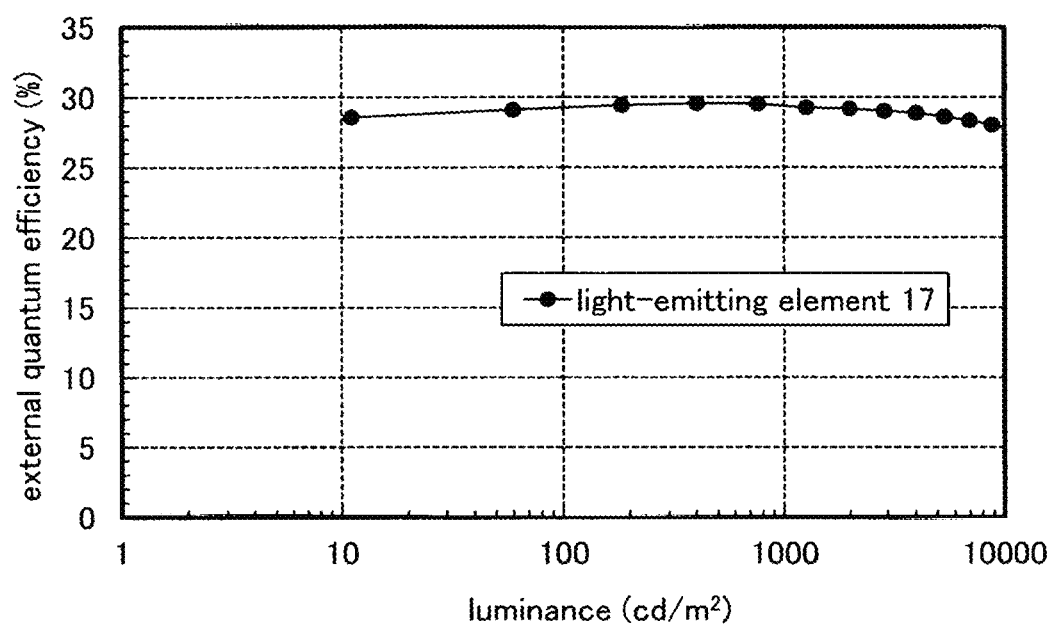
FIG. 41 shows luminance-external quantum efficiency characteristics of the light-emitting element in Example 7.

FIGS. 39 to 41 and Table 14 show that the light-emitting element 17 can be driven at low voltage and has high current efficiency, high power efficiency, and high external quantum efficiency.

Figure 42:
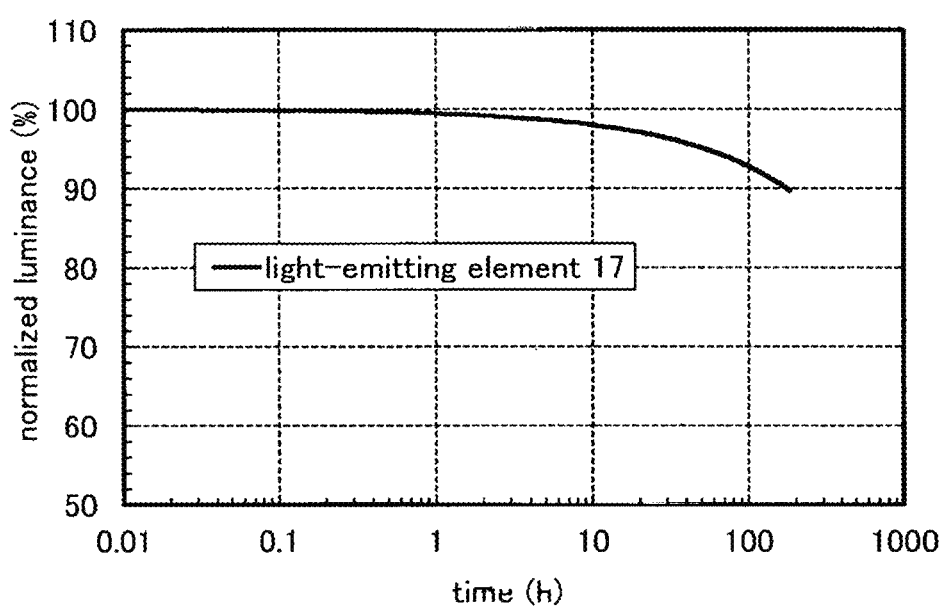
FIG. 42 shows results of a reliability test of the light-emitting element in Example 7.

Next, the light-emitting element 17 was subjected to a reliability test. Results of the reliability test are shown in FIG. 42. In FIG. 42, the vertical axis represents normalized luminance (%) with an initial luminance of 100%, and the horizontal axis represents driving time (h) of the element. In the reliability test, the light-emitting element of this example was driven at room temperature under the conditions where the initial luminance was set to 5000 cd/m$^2$ and the current

TABLE 13

| | first electrode | hole-injection layer | hole-transport layer | light-emitting layer | | | electron-transport layer | electron-injection layer | second electrode |
|---|---|---|---|---|---|---|---|---|---|
| light-emitting element 17 | ITSO 110 nm | DBT3P-II:MoOx (=4:2) 20 nm | BPAFLP 20 nm | 4,6mCzP2Pm:PCBBiF:[Ir(tBuppm)$_2$(acac)] (=0.7:0.3:0.05) 20 nm | 4,6mCzP2Pm:PCBBiF:[Ir(tBuppm)$_2$(acac)] (=0.8:0.2:0.05) 20 nm | 4,6mCzP2Pm 10 nm | BPhen 10 nm | LiF 1 nm | Al 200 nm |

The light-emitting element 17 was sealed using a glass substrate in a glove box containing a nitrogen atmosphere so as not to be exposed to the air. Then, operational characteristics of the light-emitting element were measured. Note that the measurements were carried out at room temperature (in an atmosphere kept at 25° C.).

FIG. 39 shows luminance-current efficiency characteristics of the light-emitting element of this example. In FIG. 39, the horizontal axis represents luminance (cd/m$^2$), and the vertical axis represents current efficiency (cd/A). FIG. 40 shows voltage-luminance characteristics. In FIG. 40, the horizontal axis represents voltage (V), and the vertical axis represents luminance (cd/m$^2$). FIG. 41 shows luminance-external quantum efficiency characteristics. In FIG. 41, the horizontal axis represents luminance (cd/m$^2$), and the vertical axis represents external quantum efficiency (%). Table 14 shows the voltage (V), current density (mA/cm$^2$), CIE chromaticity coordinates (x, y), current efficiency (cd/A), power efficiency (lm/W), and external quantum efficiency (%) of the light-emitting element 17 at a luminance of 760 cd/m$^2$.

density was constant. FIG. 42 shows that the light-emitting element 17 kept 90% of the initial luminance after 180 hours elapsed.

As described above, it has been found that a light-emitting element exhibiting high emission efficiency can be obtained in accordance with one embodiment of the present invention. It has also been found that a light-emitting element having a long lifetime can be obtained in accordance with one embodiment of the present invention.

Reference Example 1

A method for synthesizing N-(1,1'-biphenyl-4-yl)-N-[4-(9-phenyl-9H-carbazol-3-yl)phenyl]-9,9-dimethyl-9H-fluoren-2-amine (abbreviation: PCBBiF) used in Examples 1, 2, and 4 and represented by the following structural formula (128) will be described.

TABLE 14

| | voltage (V) | current density (mA/cm$^2$) | chromaticity x | chromaticity y | current efficiency (cd/A) | power efficiency (lm/W) | external quantum efficiency (%) |
|---|---|---|---|---|---|---|---|
| light-emitting element 17 | 2.8 | 0.67 | 0.41 | 0.58 | 113 | 127 | 30 |

[Chemical formula 29]

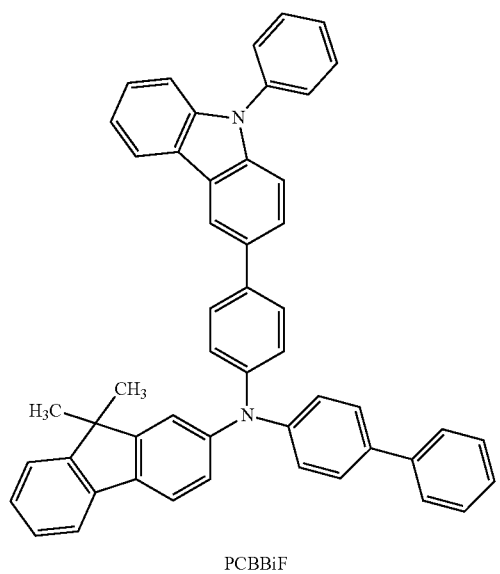

PCBBiF

Step 1: Synthesis of N-(1,1'-biphenyl-4-yl)-9,9-dimethyl-N-phenyl-9H-fluoren-2-amine A synthesis scheme of Step 1 is shown in (x-1).

[Chemical formula 30]

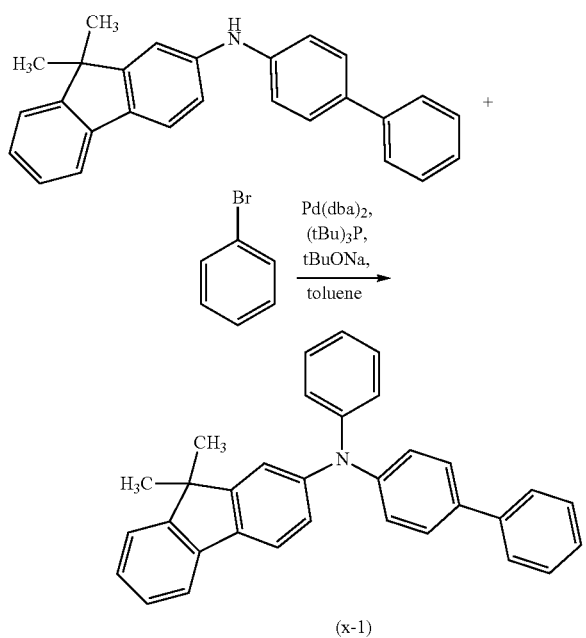

(x-1)

In a 1 L three-neck flask were placed 45 g (0.13 mol) of N-(1,1'-biphenyl-4-yl)-9,9-dimethyl-9H-fluoren-2-amine, 36 g (0.38 mol) of sodium tert-butoxide, 21 g (0.13 mol) of bromobenzene, and 500 mL of toluene. The mixture was degassed by being stirred while the pressure was being reduced, and after the degassing, the atmosphere in the flask was replaced with nitrogen. Then, 0.8 g (1.4 mmol) of bis(dibenzylideneacetone)palladium(0) and 12 mL (5.9 mmol) of tri(tert-butyl)phosphine (a 10 wt % hexane solution) were added.

The mixture was stirred under a nitrogen stream at 90° C. for 2 hours. Then, the mixture was cooled to room temperature, and a solid was separated by suction filtration. The obtained filtrate was concentrated to give about 200 mL of a brown liquid. The brown liquid was mixed with toluene, and the resulting solution was purified using Celite (manufactured by Wako Pure Chemical Industries, Ltd., Catalog No. 531-16855 (the same applies to Celite in the following description and the description is repeated)), alumina, Florisil (manufactured by Wako Pure Chemical Industries, Ltd., Catalog No. 540-00135 (the same applies to Florisil in the following description and the description is repeated)). The resulting filtrate was concentrated to give a light yellow liquid. The light yellow liquid was recrystallized from hexane to give 52 g of target light yellow powder in a yield of 95%.

Step 2: Synthesis of N-(1,1'-biphenyl-4-yl)-N-(4-bromophenyl)-9,9-dimethyl-9H-fluoren-2-amine A synthesis scheme of Step 2 is shown in (x-2).

[Chemical formula 31]

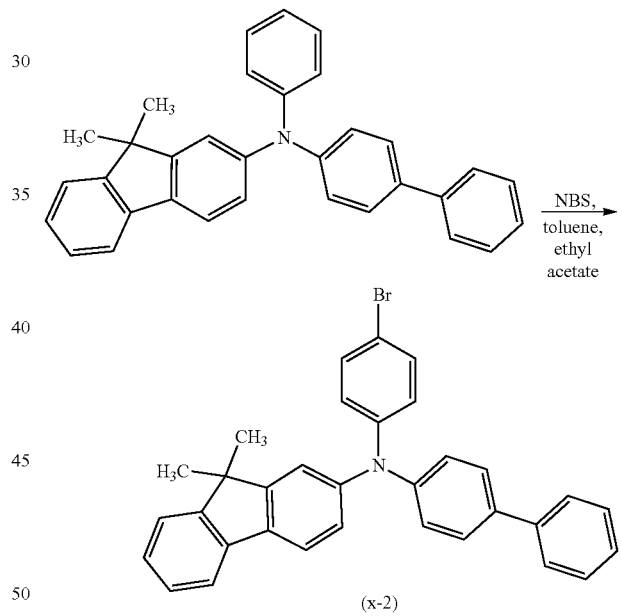

(x-2)

In a 1 L Mayer flask was placed 45 g (0.10 mol) of N-(1,1'-biphenyl-4-yl)-9,9-dimethyl-N-phenyl-9H-fluoren-2-amine, which was dissolved in 225 mL of toluene by stirring while being heated. After the solution was naturally cooled to room temperature, 225 mL of ethyl acetate and 18 g (0.10 mol) of N-bromosuccinimide (abbreviation: NBS) were added, and the mixture was stirred at room temperature for 2.5 hours. After the stirring, the mixture was washed three times with a saturated aqueous solution of sodium hydrogen carbonate and once with a saturated aqueous solution of sodium chloride. Magnesium sulfate was added to the resulting organic layer, and the mixture was left still for 2 hours for drying. The mixture was subjected to gravity filtration to remove magnesium sulfate, and the resulting filtrate was concentrated to give a yellow liquid. The yellow liquid was mixed with toluene, and the solution was purified using Celite, alumina, and Florisil. The resulting solution was concentrated to give a light yellow solid. The light yellow solid was recrystallized from toluene/ethanol to give 47 g of target white powder in a yield of 89%.

Step 3: Synthesis of PCBBiF

A synthesis scheme of Step 3 is shown in (x-3).

[Chemical formula 32]

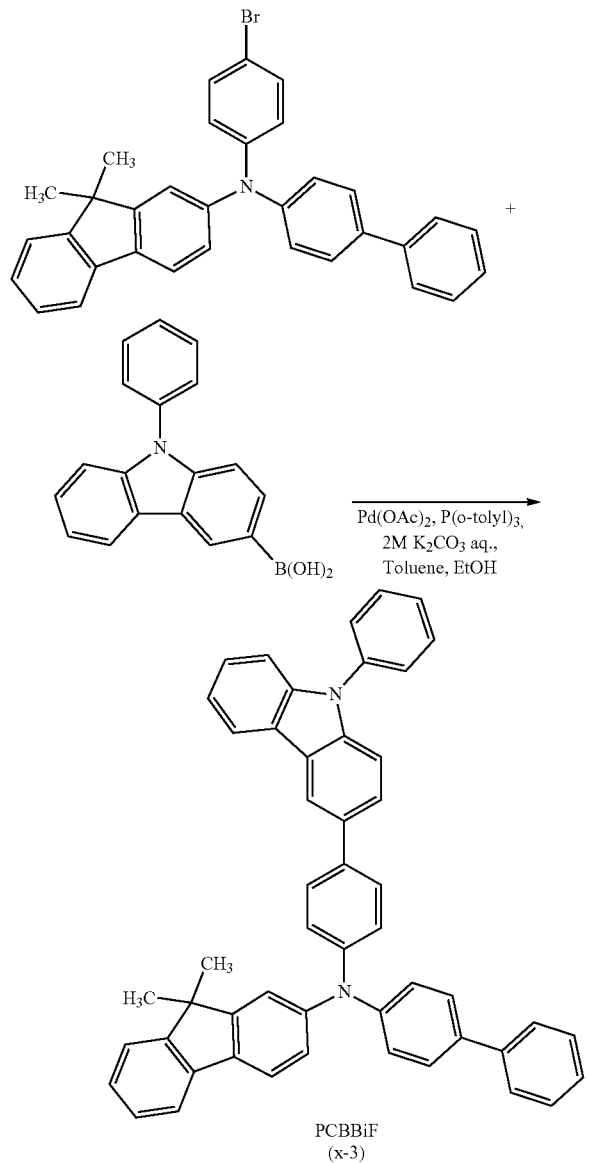

PCBBiF
(x-3)

In a 1 L three-neck flask were placed 41 g (80 mmol) of N-(1,1'-biphenyl-4-yl)-N-(4-bromophenyl)-9,9-dimethyl-9H-fluoren-2-amine and 25 g (88 mmol) of 9-phenyl-9H-carbazole-3-boronic acid, to which 240 mL of toluene, 80 mL of ethanol, and 120 mL of an aqueous solution of potassium carbonate (2.0 mol/L) were added. The mixture was degassed by being stirred while the pressure was being reduced, and after the degassing, the atmosphere in the flask was replaced with nitrogen. Further, 27 mg (0.12 mmol) of palladium(II) acetate and 154 mg (0.5 mmol) of tri(ortho-tolyl)phosphine were added. The mixture was degassed again by being stirred while the pressure was being reduced, and after the degassing, the atmosphere in the flask was replaced with nitrogen. The mixture was stirred under a nitrogen stream at 110° C. for 1.5 hours.

After the mixture was naturally cooled to room temperature while being stirred, the aqueous layer of the mixture was extracted twice with toluene. The resulting solution of the extract and the organic layer were combined and washed twice with water and twice with a saturated aqueous solution of sodium chloride. Magnesium sulfate was added to the solution, and the mixture was left still for drying. The mixture was subjected to gravity filtration to remove magnesium sulfate, and the resulting filtrate was concentrated to give a brown solution. The brown solution was mixed with toluene, and the resulting solution was purified using Celite, alumina, and Florisil. The resulting filtrate was concentrated to give a light yellow solid. The light yellow solid was recrystallized from ethyl acetate/ethanol to give 46 g of target light yellow powder in a yield of 88%.

By a train sublimation method, 38 g of the obtained light yellow powder was purified by sublimation. In the sublimation purification, the light yellow powder was heated at 345° C. under a pressure of 3.7 Pa with an argon flow rate of 15 mL/min. After the sublimation purification, 31 g of a target light yellow solid was obtained at a collection rate of 83%.

This compound was identified as N-(1,1'-biphenyl-4-yl)-N-[4-(9-phenyl-9H-carbazol-3-yl)phenyl]-9,9-dimethyl-9H-fluor en-2-amine (abbreviation: PCBBiF), which was the target of the synthesis, by nuclear magnetic resonance (NMR) spectroscopy.

$^1$H NMR data of the obtained light yellow solid are shown below.

$^1$H NMR (CDCl$_3$, 500 MHz): δ=1.45 (s, 6H), 7.18 (d, J=8.0 Hz, 1H), 7.27-7.32 (m, 8H), 7.40-7.50 (m, 7H), 7.52-7.53 (m, 2H), 7.59-7.68 (m, 12H), 8.19 (d, J=8.0 Hz, 1H), 8.36 (d, J=1.1 Hz, 1H).

Figure 21A:
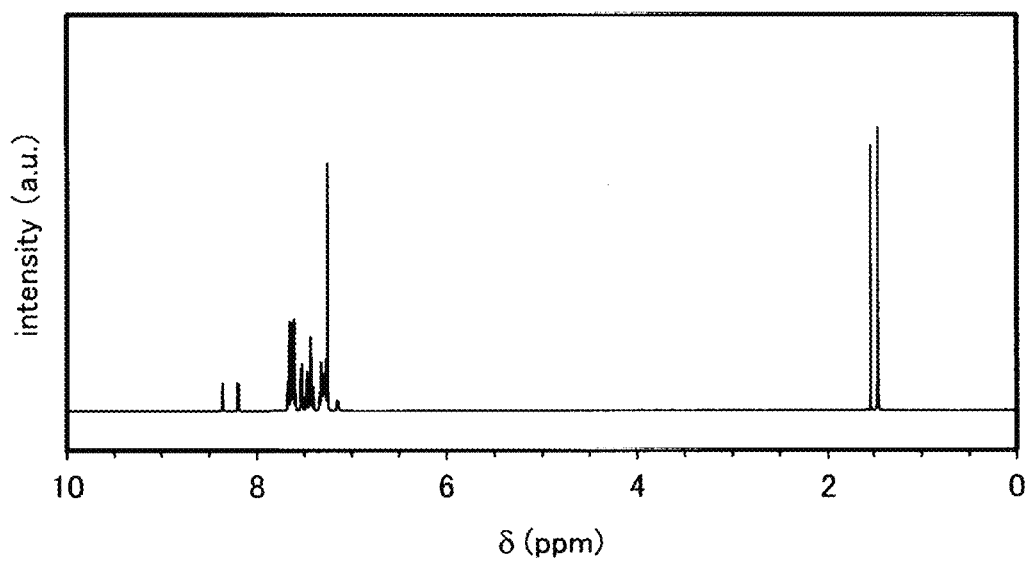
FIGS. 21A and 21B show $^1$H NMR charts of N-(1,1'-biphenyl-4-yl)-N-[4-(9-phenyl-9H-carbazol-3-yl)phenyl]-9,9-dimethyl-9H-fluor en-2-amine (abbreviation: PCBBiF).
Figure 21B:
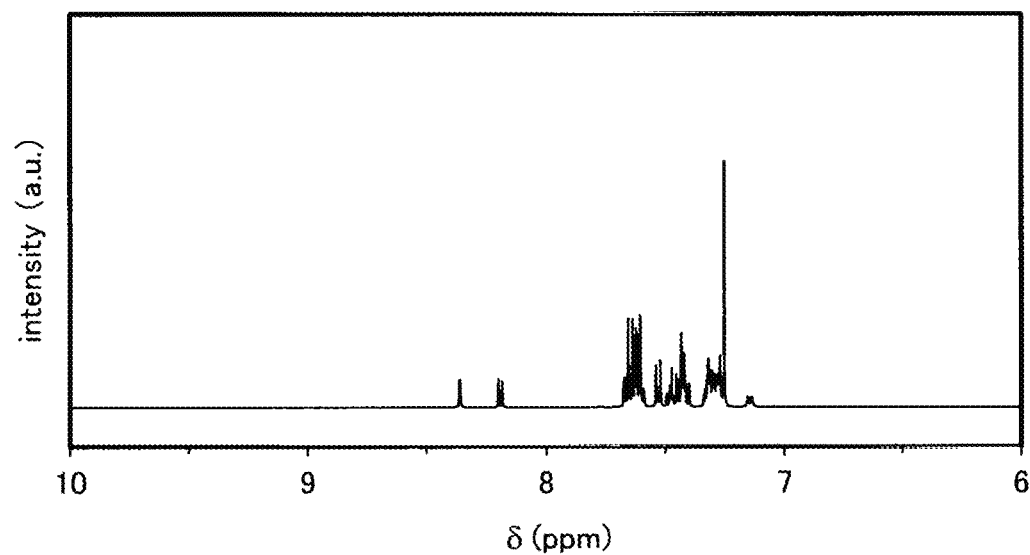

FIGS. 21A and 21B show NMR charts. Note that FIG. 21B is a chart where the range of from 6.00 ppm to 10.0 ppm in FIG. 21A is enlarged.

Figure 22A:
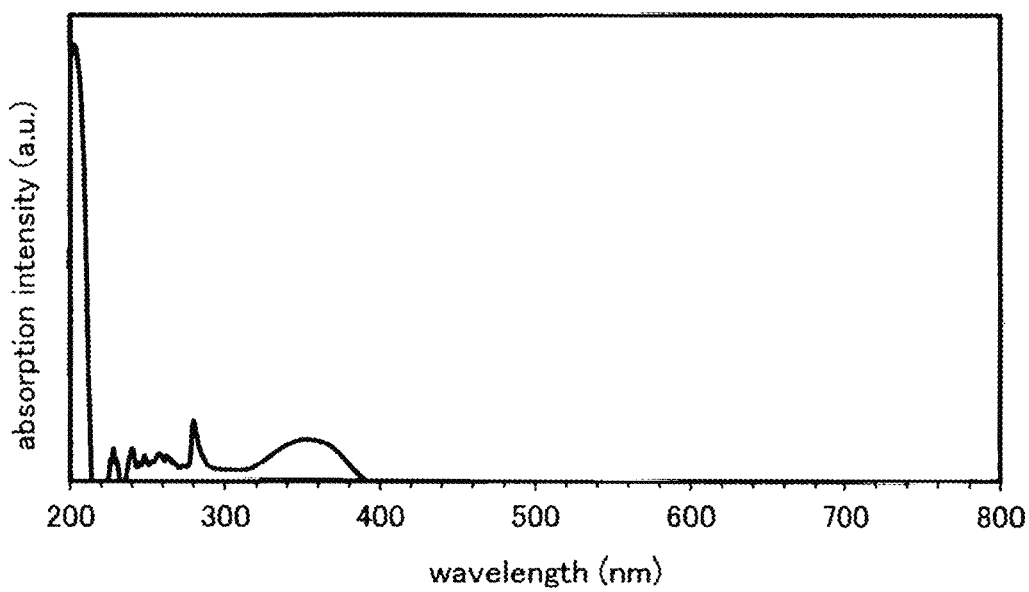
FIGS. 22A and 22B show an absorption spectrum and an emission spectrum of PCBBiF in a toluene solution of PCBBiF.
Figure 22B:
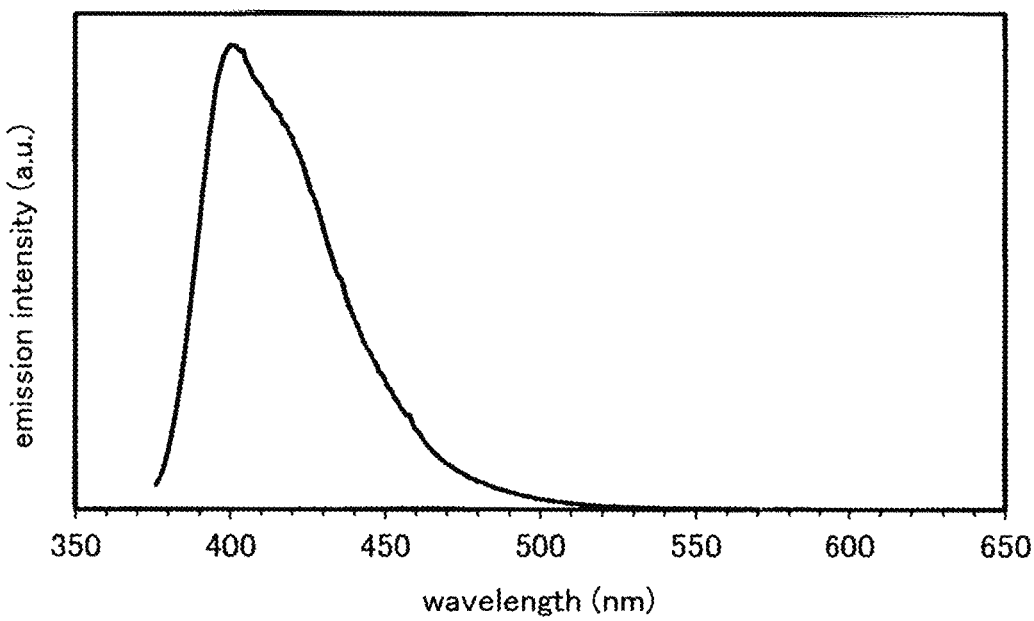
Figure 23A:
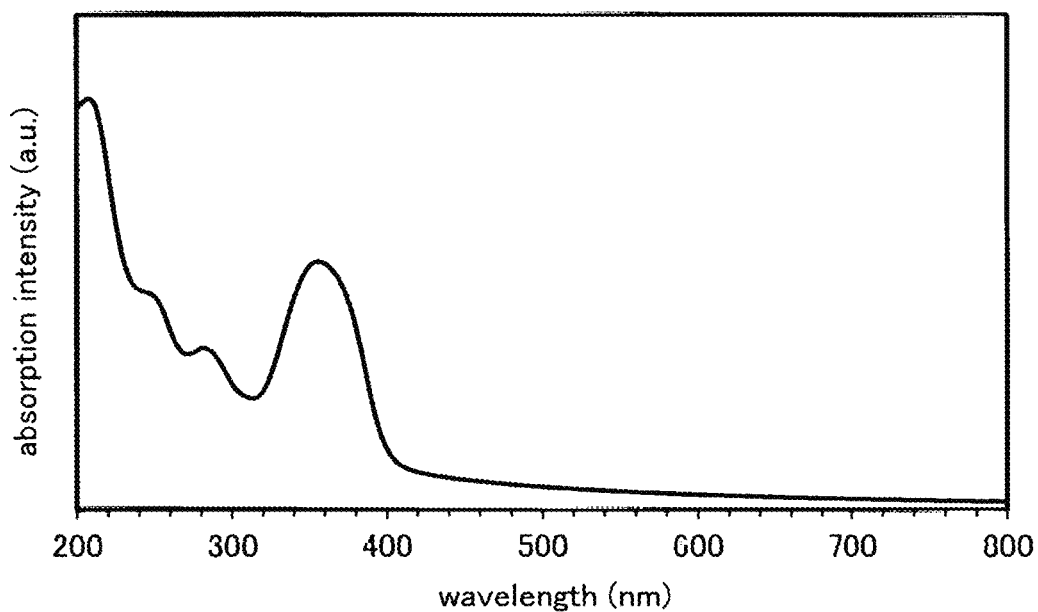
FIGS. 23A and 23B show an absorption spectrum and an emission spectrum of a thin film of PCBBiF.
Figure 23B:
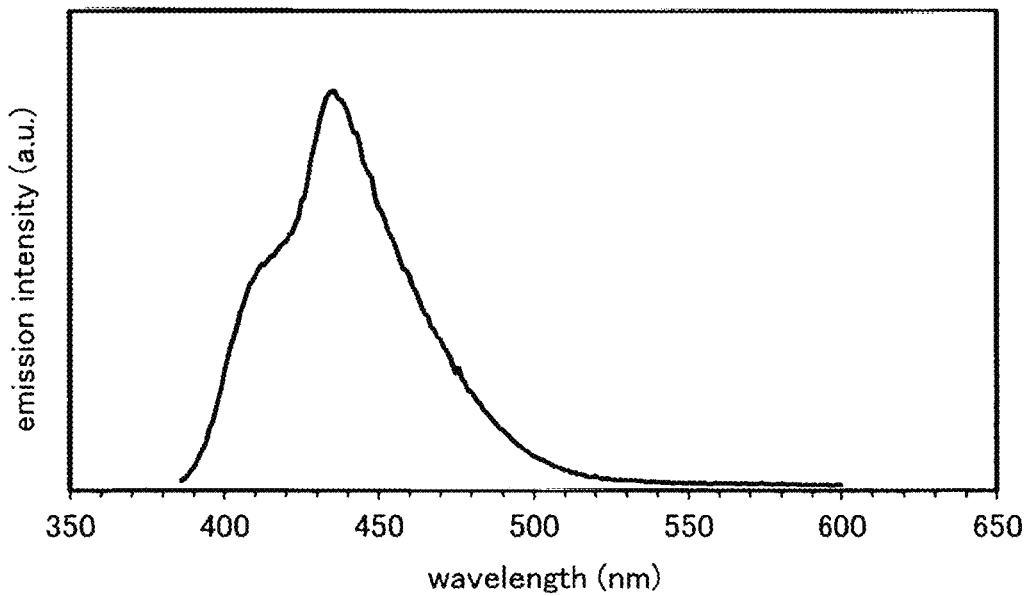

Further, FIG. 22A shows the absorption spectrum of PCBBiF in a toluene solution of PCBBiF, and FIG. 22B shows the emission spectrum thereof. In addition, FIG. 23A shows the absorption spectrum of a thin film of PCBBiF, and FIG. 23B shows the emission spectrum thereof. An ultraviolet-visible spectrophotometer (V-550, manufactured by JASCO Corporation) was used for the measurements. Samples were prepared in such a way that the solution was put in a quartz cell and the thin film was formed on a quartz substrate by evaporation. Here are shown the absorption spectrum for the solution which was obtained by subtracting the absorption spectra of quartz and toluene from those of quartz and the solution, and the absorption spectrum for the thin film which was obtained by subtracting the absorption spectrum of the quartz substrate from those of the quartz substrate and the thin film. In FIGS. 22A and 22B and FIGS. 23A and 23B, the horizontal axis represents wavelength (nm) and the vertical axis represents intensity (arbitrary unit). In the case of the toluene solution, an absorption peak was found at around 350 nm, and peaks of the emission wavelengths were at 401 nm and 420 nm (at an excitation wavelength of 360 nm). In the case of the thin film, an absorption peak was found at around 356 nm, and peaks of the emission wavelengths were at 415 nm and 436 nm (at an excitation wavelength of 370 nm).

Reference Example 2

A method for synthesizing 9,9-dimethyl-N-[4-(1-naphthyl)phenyl]-N-[4-(9-phenyl-9H-carbazol-3-yl)phenyl]-9H-fluoren-2-amine (abbreviation: PCBNBF) used in Example 1 will be described.

95

[Chemical formula 33]

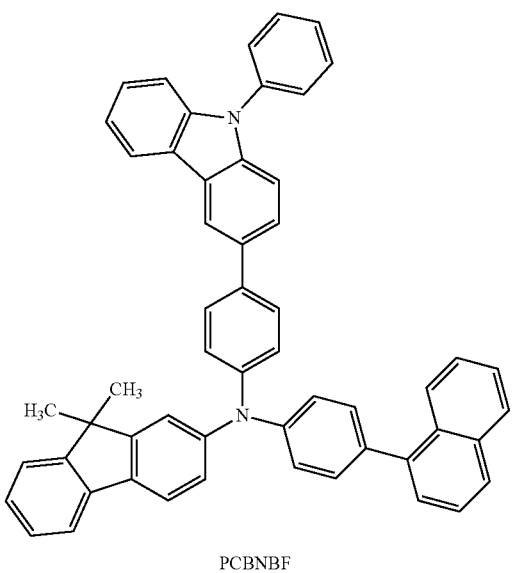

PCBNBF

Step 1: Synthesis of
1-(4-bromophenyl)-naphthalene

A synthesis scheme of Step 1 is shown in (y-1).

[Chemical formula 34]

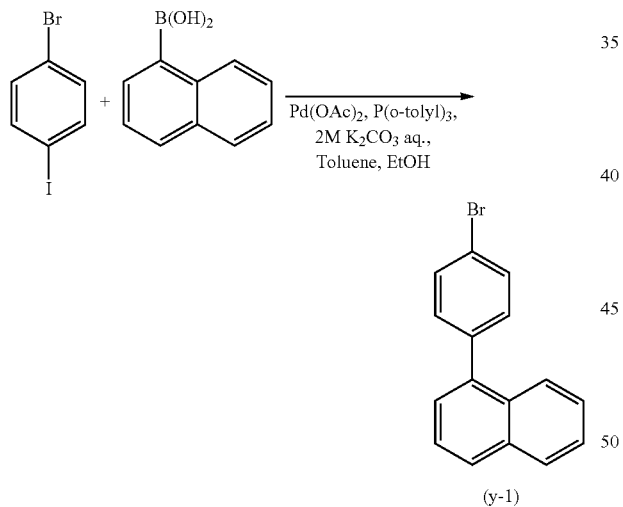

(y-1)

To a 3 L three-neck flask were added 47 g (0.28 mol) of 1-naphthaleneboronic acid and 82 g (0.29 mol) of 4-bromoiodobenzene and added 750 mL of toluene and 250 mL of ethanol. The mixture was degassed by being stirred while the pressure was being reduced, and after the degassing, the atmosphere in the flask was replaced with nitrogen. To the solution was added 415 mL of an aqueous solution of potassium carbonate (2.0 mol/L). The mixture was degassed again by being stirred while the pressure was being reduced, and after the degassing, the atmosphere in the flask was replaced with nitrogen. Further, 4.2 g (14 mmol) of tri(ortho-tolyl)phosphine and 0.7 g (2.8 mmol) of palladium(II) acetate were added. This mixture was stirred at 90° C. for 1 hour under a nitrogen stream.

96

After the stirring, the mixture was naturally cooled to room temperature, and the aqueous layer of the mixture was extracted three times with toluene. The resulting solution of the extract and the organic layer were combined and washed twice with water and twice with a saturated aqueous solution of sodium chloride. Then, magnesium sulfate was added, and the mixture was left still for 18 hours for drying. The mixture was subjected to gravity filtration to remove magnesium sulfate, and the resulting filtrate was concentrated to give an orange liquid.

To the orange liquid was added 500 mL of hexane, and the resulting solution was purified through Celite and Florisil. The obtained filtrate was concentrated to give a colorless liquid. To the colorless liquid was added hexane, and the mixture was left still at −10° C., and the precipitated impurities were separated by filtration. The resulting filtrate was concentrated to give a colorless liquid. The colorless liquid was purified by distillation under reduced pressure, and the resulting yellow liquid was purified by silica gel column chromatography (developing solvent:hexane) to give 56 g of a target colorless liquid in a yield of 72%.

Step 2: Synthesis of 9,9-dimethyl-N-(4-naphthyl)
phenyl-N-phenyl-9H-fluoren-2-amine A synthesis scheme of Step 2 is shown in (y-2).

[Chemical formula 35]

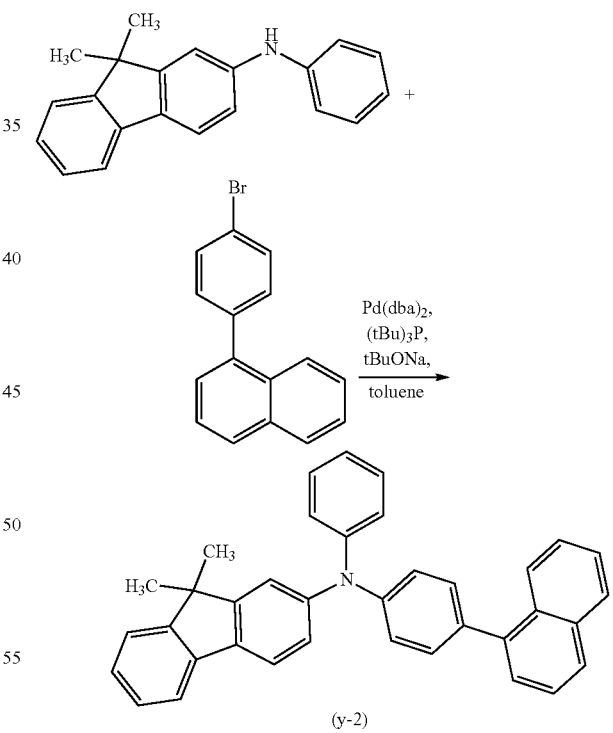

(y-2)

In a 1 L three-neck flask were placed 40 g (0.14 mol) of 9,9-dimethyl-N-phenyl-9H-fluoren-2-amine, 40 g (0.42 mol) of sodium tert-butoxide, and 2.8 g (1.4 mmol) of bis(dibenzylideneacetone)palladium(0), and added 560 mL of a toluene solution of 44 g (0.15 mol) of 1-(4-bromophenyl)naphthalene. The mixture was degassed by being stirred while the pressure was being reduced, and after the degassing, the atmosphere in the flask was replaced with nitrogen.

Then, 14 mL (7.0 mmol) of tri(tert-butyl)phosphine (a 10 wt % hexane solution) was added, and the mixture was stirred under a nitrogen stream at 110° C. for 2 hours.

Then, the mixture was cooled to room temperature, and a solid was separated by suction filtration. The obtained filtrate was concentrated to give a dark brown liquid. The dark brown liquid was mixed with toluene, and the resulting solution was purified through Celite, alumina, and Florisil. The resulting filtrate was concentrated to give a light yellow liquid. The light yellow liquid was recrystallized from acetonitrile to give 53 g of target light yellow powder in a yield of 78%.

Step 3: Synthesis of N-(4-bromophenyl)-9,9-dimethyl-N-[4-(1-naphthyl)phenyl]-9H-fluoren-2-amine A synthesis scheme of Step 3 is shown in (y-3).

[Chemical formula 36]

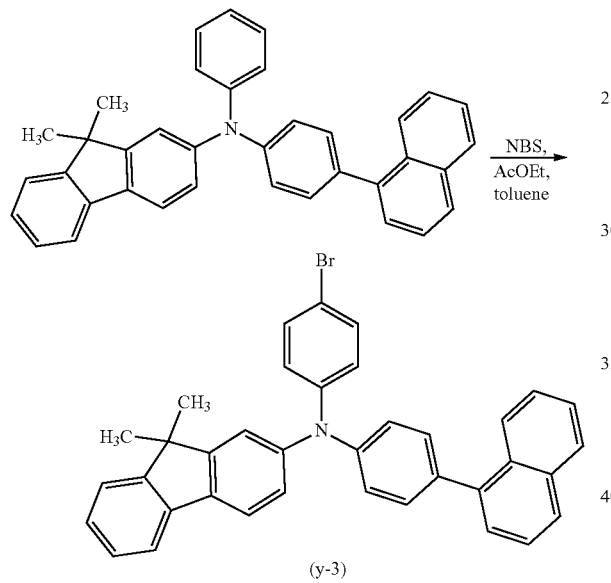

(y-3)

To a 2 L Mayer flask were added 59 g (0.12 mol) of 9,9-dimethyl-N-(4-naphthyl)phenyl-N-phenyl-9H-fluoren-2-amine and 300 mL of toluene, and the mixture was stirred while being heated. After the resulting solution was naturally cooled to room temperature, 300 mL of ethyl acetate and then 21 g (0.12 mol) of N-bromosuccinimide (abbreviation: NBS) were added, and the mixture was stirred at room temperature for about 2.5 hours. To the mixture was added 400 mL of a saturated aqueous solution of sodium hydrogen carbonate, and the mixture was stirred at room temperature. The organic layer of the mixture was washed twice with a saturated aqueous solution of sodium hydrogen carbonate and twice with a saturated aqueous solution of sodium chloride. Then, magnesium sulfate was added, and the mixture was left still for 2 hours for drying. After the mixture was subjected to gravity filtration to remove magnesium sulfate, the resulting filtrate was concentrated to give a yellow liquid. After the liquid was dissolved in toluene, the solution was purified through Celite, alumina, and Florisil to give a light yellow solid. The obtained light yellow solid was reprecipitated with toluene/acetonitrile to give 56 g of target white powder in a yield of 85%.

Step 4. Synthesis of PCBNBF

A synthesis scheme of Step 4 is shown in (y-4).

[Chemical formula 37]

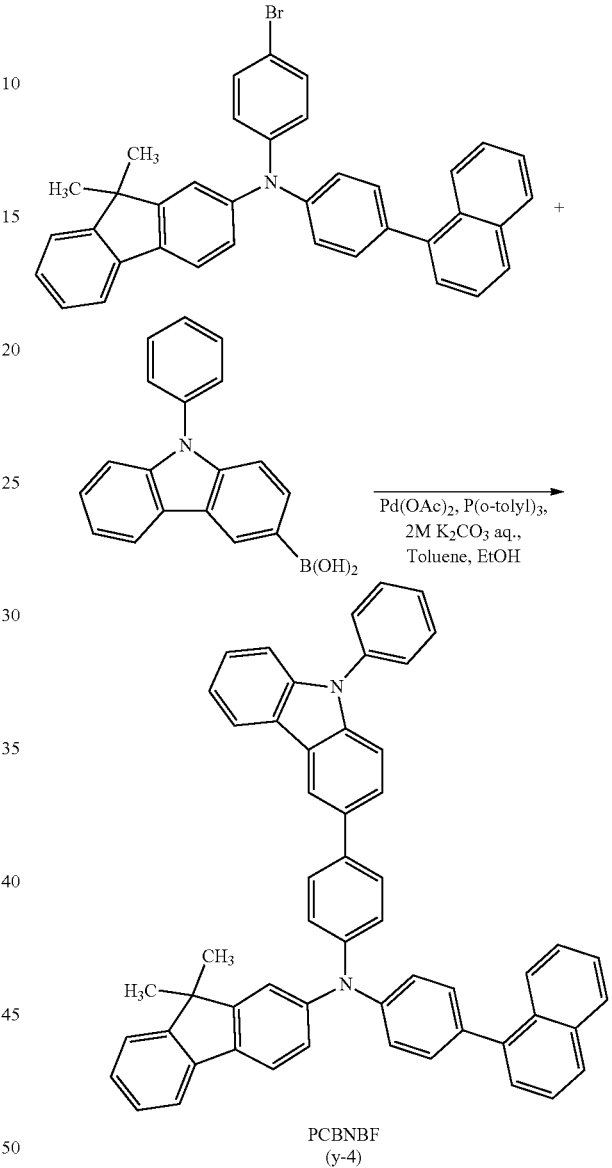

PCBNBF
(y-4)

In a 1 L three-neck flask were placed 51 g (90 mmol) of N-(4-bromophenyl)-9,9-dimethyl-N-[4-(1-naphthyl)phenyl]-9H-fluoren-2-amine, 28 g (95 mmol) of 9-phenyl-9H-carbazole-3-boronic acid, 0.4 mg (1.8 mmol) of palladium (II) acetate, 1.4 g (4.5 mmol) of tri(ortho-tolyl)phosphine, 300 mL of toluene, 100 mL of ethanol, 135 mL of an aqueous solution of sodium carbonate (2.0 mol/L). The mixture was degassed by being stirred while the pressure was being reduced, and after the degassing, the atmosphere in the flask was replaced with nitrogen. The mixture was stirred under a nitrogen stream at 90° C. for 1.5 hours. After the stirring, the mixture was cooled to room temperature, and a solid was collected by suction filtration. The organic layer was extracted from the obtained mixture of the water layer and the organic layer and concentrated to give a brown solid. The brown solid was recrystallized from toluene/ethyl acetate/ethanol to give target white powder. The solid collected after the stirring and the white powder obtained by the recrystallization were dissolved in toluene, and the solution was purified through Celite, alumina, and Florisil. The resulting solution was concentrated and recrystallized from toluene/ethanol to give 54 g of target white powder in a yield of 82%.

By a train sublimation method, 51 g of the obtained white powder was purified by sublimation. In the sublimation purification, the white powder was heated at 360° C. under a pressure of 3.7 Pa with an argon flow rate of 15 mL/min. After the sublimation purification, 19 g of a target light yellow solid was obtained at a collection rate of 38%.

This compound was identified as 9,9-dimethyl-N-[4-(1-naphthyl)phenyl]-N-[4-(9-phenyl-9H-carbazol-3-yl)phenyl]-9H-fluoren-2-amine (abbreviation: PCBNBF), which was the target of the synthesis, by nuclear magnetic resonance (NMR) spectroscopy.

$^1$H NMR data of the obtained substance are shown below.

$^1$H NMR (CDCl$_3$, 500 MHz): δ=1.50 (s, 6H), 7.21 (dd, J=8.0 Hz, 1.6 Hz, 1H), 7.26-7.38 (m, 8H), 7.41-7.44 (m, 5H), 7.46-7.55 (m, 6H), 7.59-7.69 (m, 9H), 7.85 (d, J=8.0 Hz, 1H), 7.91 (dd, J=7.5 Hz, 1.7 Hz, 1H), 8.07-8.09 (m, 1H), 8.19 (d, J=8.0 Hz, 1H), 8.37 (d, J=1.7 Hz, 1H).

Reference Example 3

A method for synthesizing N-(1,1'-biphenyl-4-yl)-N-[4-(9-phenyl-9H-carbazol-3-yl)phenyl]-9,9'-spirobi[9H-fluoren]-2-amine (abbreviation: PCBBiSF) used in Example 3 and represented by the following structural formula (119) will be described.

[Chemical formula 38]

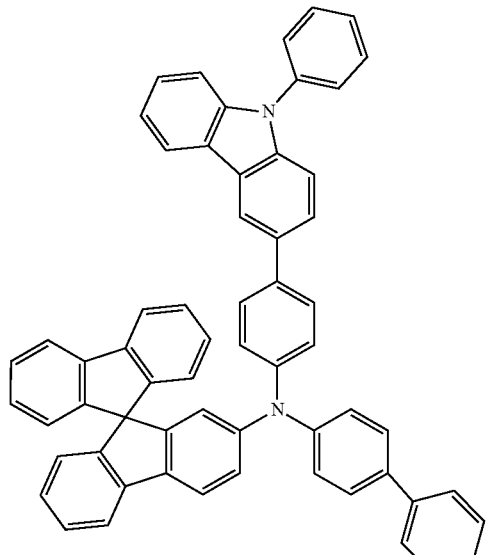

(119)

PCBBiSF

Step 1: Synthesis of N-(1,1'-biphenyl-4-yl)-N-phenyl-9,9'-spirobi[9H-fluoren]-2-amine A synthesis scheme of Step 1 is shown in (z-1).

[Chemical formula 39]

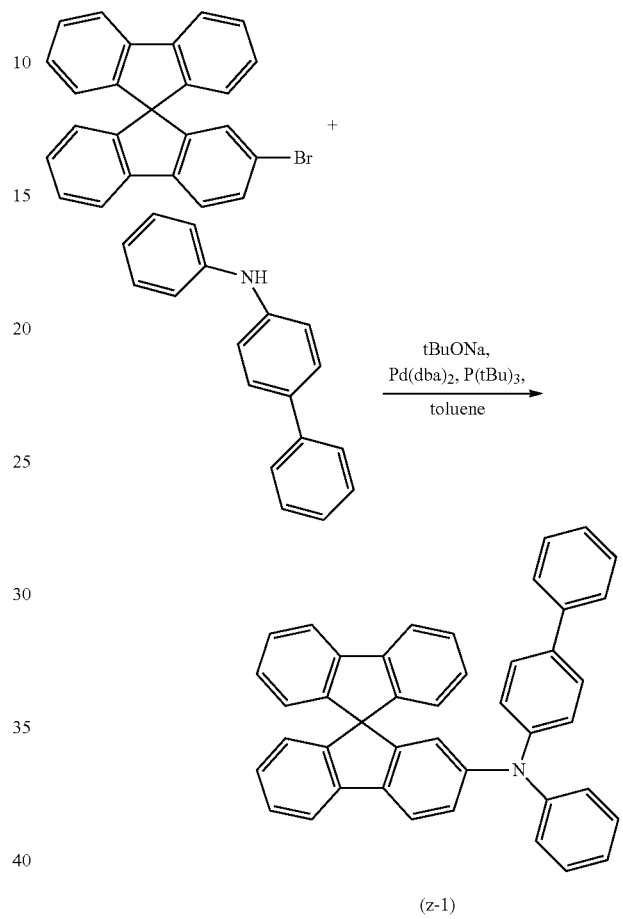

(z-1)

In a 200 mL three-neck flask were placed 4.8 g (12 mmol) of 2-bromo-9,9'-spirobi[9H-fluorene], 3.0 g (12 mmol) of 4-phenyl-diphenylamine, 3.5 g (37 mmol) of sodium tert-butoxide, and the atmosphere in the flask was replaced with nitrogen. To the mixture were added 60 mL of dehydrated toluene and 0.2 mL of tri(tert-butyl)phoshine (a 10% hexane solution), and the mixture was degassed by being stirred while the pressure was being reduced. To the mixture was added 70 mg (0.12 mmol) of bis(dibenzylideneacetone)palladium(0), and the mixture was heated and stirred under a nitrogen stream at 110° C. for 8 hours. After the stirring, water was added to the mixture, and the aqueous layer was extracted with toluene. The solution of the extract and the organic layer were combined and washed with a saturated aqueous solution of sodium chloride. The organic layer was dried with magnesium sulfate. This mixture was separated by gravity filtration, and the filtrate was concentrated to give a solid.

This solid was purified by silica gel column chromatography. In the column chromatography, toluene:hexane=1:5 and then toluene:hexane=1:3 were used as developing solvents. The resulting fraction was concentrated to give a solid. The obtained solid was recrystallized from toluene/ethyl acetate to give 5.7 g of a white solid in a yield of 83%.

Step 2: Synthesis of N-(1,1'-biphenyl-4-yl)-N-(4-bromophenyl)-9,9'-spirobi[9H-fluoren]-2-amine A synthesis scheme of Step 2 is shown in (z-2).

[Chemical formula 40]

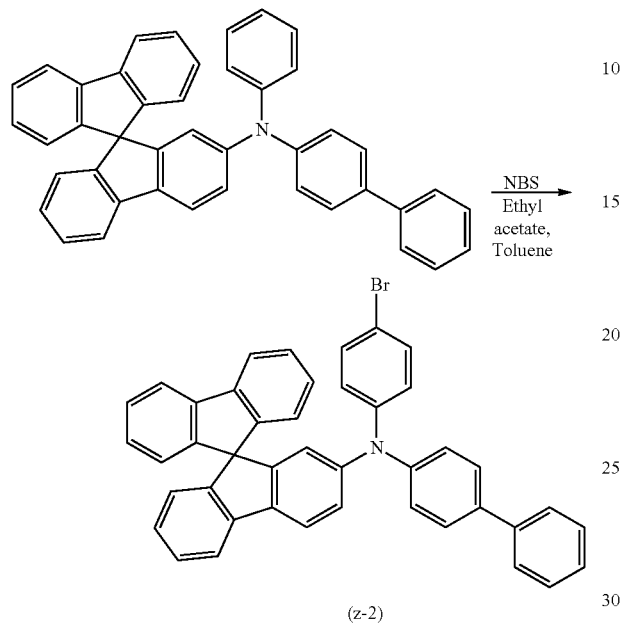

(z-2)

To a 100 mL three-neck flask were added 3.0 g (5.4 mmol) of N-(1,1'-biphenyl-4-yl)-N-phenyl-9,9'-spirobi[9H-fluoren]-2-amine, 20 mL of toluene, and 40 mL of ethyl acetate. To the solution was added 0.93 g (5.2 mmol) of N-bromosuccinimide (abbreviation: NBS), and the mixture was stirred for 25 hours. After the stirring, the mixture was washed with water and a saturated aqueous solution of sodium hydrogen carbonate, and then the organic layer was dried over magnesium sulfate. This mixture was separated by gravity filtration, and the filtrate was concentrated to give a solid. This solid was purified by silica gel column chromatography. In the column chromatography, hexane and then toluene:hexane=1:5 were used as developing solvents. The resulting fraction was concentrated to give a solid. The obtained solid was recrystallized from ethyl acetate/hexane to give 2.8 g of a white solid in a yield of 83%.

Step 3: Synthesis of PCBBiSF

A synthesis scheme of Step 3 is shown in (z-3).

[Chemical formula 41]

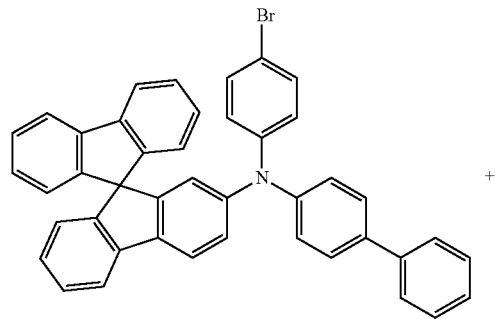

+

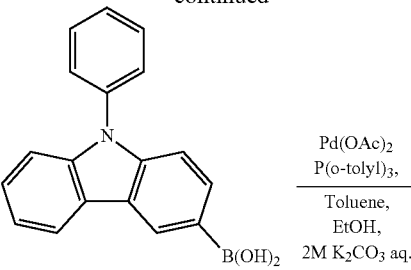

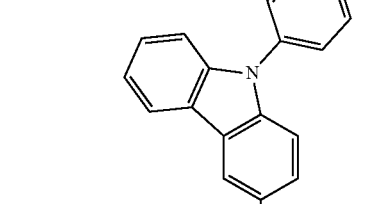

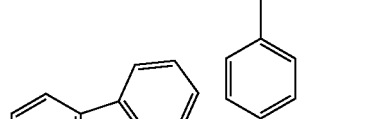

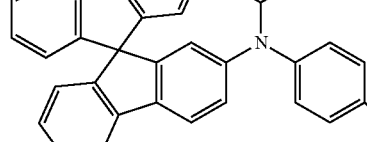

PCBBiSF
(z-3)

In a 200 mL three-neck flask were placed 2.4 g (3.8 mmol) of N-(1,1'-biphenyl-4-yl)-N-(4-bromophenyl)-9,9'-spirobi[9H-fluoren]-2-amine, 1.3 g (4.5 mmol) of 9-phenylcarbazole-3-boronic acid, 57 mg (0.19 mmol) of tri(ortho-tolyl)phosphine, and 1.2 g (9.0 mmol) of potassium carbonate. To the mixture were added 5 mL of water, 14 mL of toluene, and 7 mL of ethanol, and the mixture was degassed by being stirred under reduced pressure. To this mixture was added 8 mg (0.038 mmol) of palladium acetate, and the mixture was stirred under a nitrogen stream at 90° C. for 7.5 hours. After the stirring, the resulting mixture was extracted with toluene. The obtained solution of the extract and the organic layer were combined and washed with a saturated aqueous solution of sodium chloride and then dried over magnesium sulfate. This mixture was separated by gravity filtration, and the filtrate was concentrated to give a solid. This solid was purified by silica gel column chromatography. In the column chromatography, toluene:hexane=1:2 and then toluene:hexane=2:3 were used as developing solvents. The resulting fraction was concentrated to give a solid. The obtained solid was recrystallized from ethyl acetate/hexane to give 2.8 g of a target white solid in a yield of 94%.

By a train sublimation method, 2.8 g of the obtained solid was purified by sublimation. The sublimation purification was performed by heating at 336° C. under a pressure of 2.9 Pa with an argon flow rate of 5 mL/min. After the sublimation purification, 0.99 g of a light yellow solid was obtained at a collection rate of 35%.

This compound was identified as N-(1,1'-biphenyl-4-yl)-N-[4-(9-phenyl-9H-carbazol-3-yl)phenyl]-9,9'-spirobi[9H- fluoren]-2-amine (abbreviation: PCBBiSF), which was the target of the synthesis, by nuclear magnetic resonance (NMR) spectroscopy.

$^1$H NMR data of the obtained light yellow solid are shown below.

$^1$H NMR (CDCl$_3$, 500 MHz): δ=6.67-6.69 (m, 2H), 6.84 (d, J1=7.5 Hz, 2H), 7.04-7.11 (m, 5H), 7.13-7.17 (m, 3H), 7.28-7.45 (m, 12H), 7.46-7.53 (m, 5H), 7.57-7.64 (m, 5H), 7.74-7.77 (m, 4H), 8.17 (d, J1=7.5 Hz, 1H), 8.27 (d, J1=1.5 Hz, 1H).

Figure 24A:
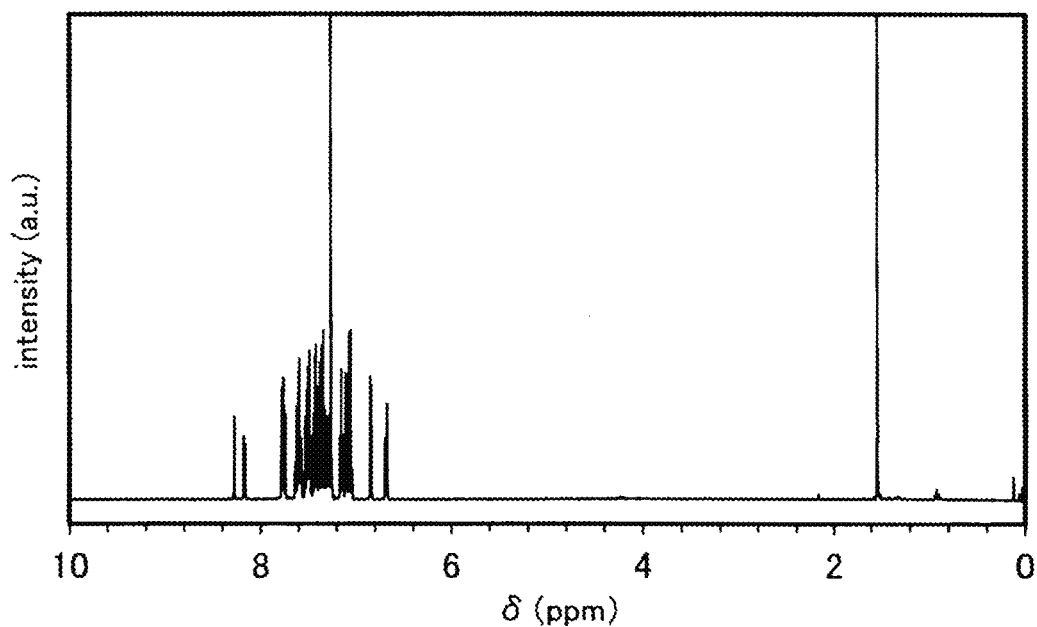
FIGS. 24A and 24B show $^1$H NMR charts of N-(1,1'-biphenyl-4-yl)-N-[4-(9-phenyl-9H-carbazol-3-yl)phenyl]-9,9'-spirobi[9H-fluoren]-2-amine (abbreviation: PCBBiSF).
Figure 24B:
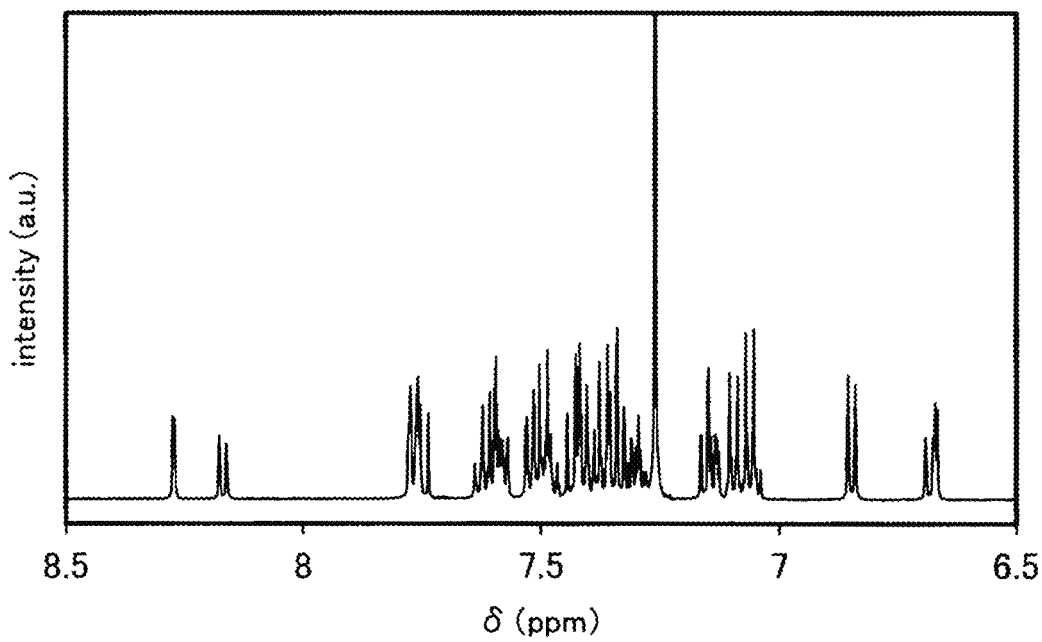

FIGS. 24A and 24B show $^1$H NMR charts. Note that FIG. 24B is a chart where the range of from 6.50 ppm to 8.50 ppm in FIG. 24A is enlarged.

Figure 25A:
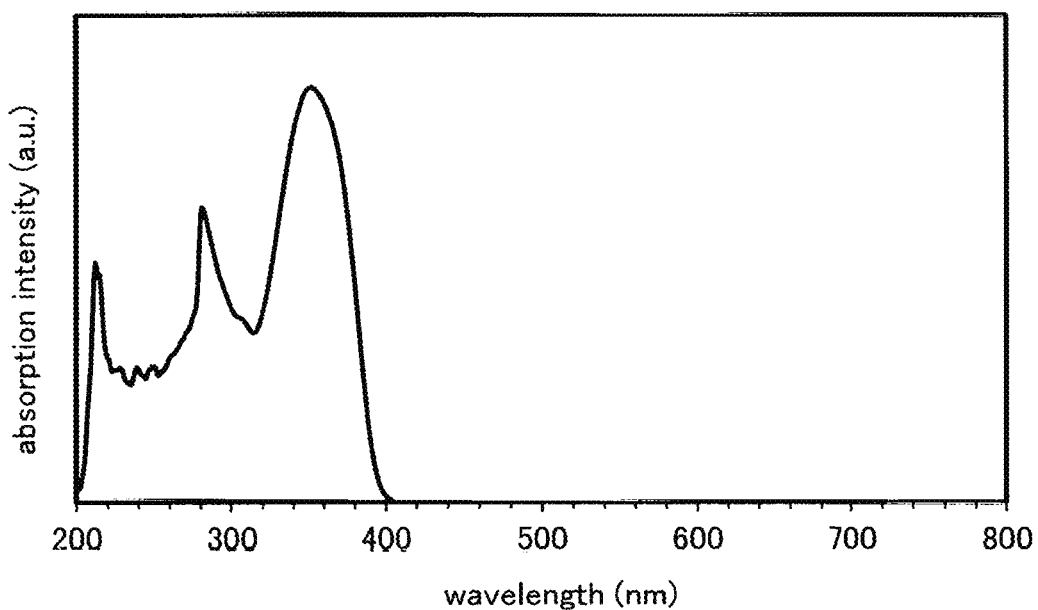
FIGS. 25A and 25B show an absorption spectrum and an emission spectrum of PCBBiSF in a toluene solution of PCBBiSF.
Figure 25B:
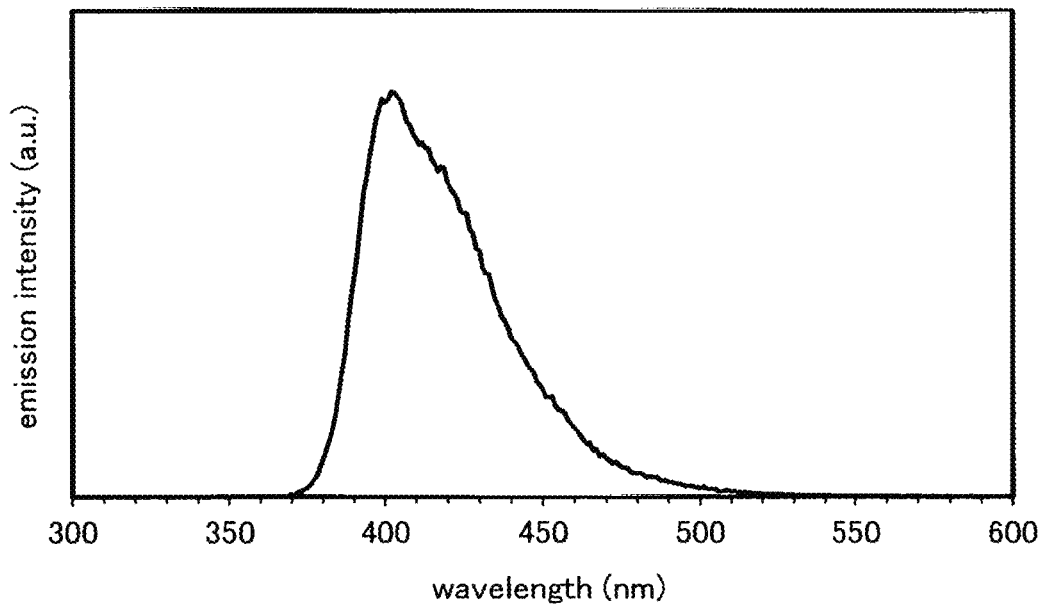
Figure 26A:
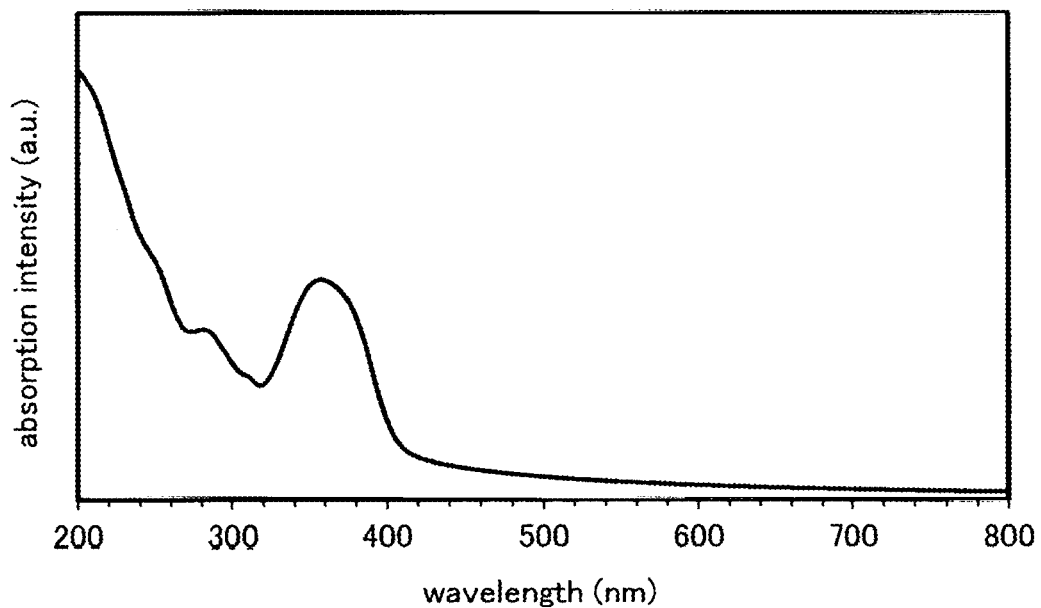
FIGS. 26A and 26B show an absorption spectrum and an emission spectrum of a thin film of PCBBiSF.
Figure 26B:
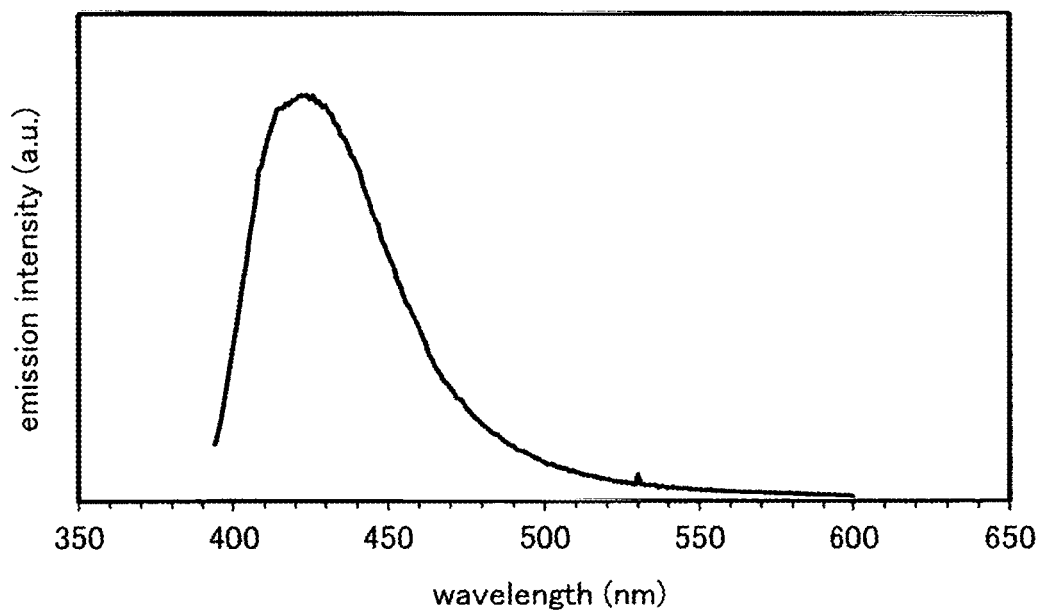

Further, FIG. 25A shows the absorption spectrum of PCBBiSF in a toluene solution of PCBBiSF, and FIG. 25B shows the emission spectrum thereof. In addition, FIG. 26A shows the absorption spectrum of a thin film of PCBBiSF, and FIG. 26B shows the emission spectrum thereof. The absorption spectra were obtained in the same manner as Reference Example 1. In FIGS. 25A and 25B and FIGS. 26A and 26B, the horizontal axis represents wavelength (nm) and the vertical axis represents intensity (arbitrary unit). In the case of the toluene solution, an absorption peak was found at around 352 nm, and a peak of the emission wavelength was at 403 nm (at an excitation wavelength of 351 nm). In the case of the thin film, an absorption peak was found at around 357 nm, and a peak of the emission wavelength was at 424 nm (at an excitation wavelength of 378 nm).

EXPLANATION OF REFERENCE

201: first electrode, 203: EL layer, 203a: first EL layer, 203b: second EL layer, 205: second electrode, 207: intermediate layer, 213: light-emitting layer, 221: first organic compound, 222: second organic compound, 223: phosphorescent compound, 301: hole-injection layer, 302: hole-transport layer, 303: light-emitting layer, 304: electron-transport layer, 305: electron-injection layer, 306: electron-injection buffer layer, 307: electron-relay layer, 308: charge-generation region, 401: support substrate, 403: light-emitting element, 405: sealing substrate, 407: sealing material, 409a: first terminal, 409b: second terminal, 411a: light extraction structure, 411b: light extraction structure, 413: planarization layer, 415: space, 417: auxiliary wiring, 419: insulating layer, 421: first electrode, 423: EL layer, 425: second electrode, 501: support substrate, 503: light-emitting element, 505: sealing substrate, 507: sealing material, 509: FPC, 511: insulating layer, 513: insulating layer, 515: space, 517: wiring, 519: partition, 521: first electrode, 523: EL layer, 525: second electrode, 531: black matrix, 533: color filter, 535: overcoat layer, 541a: transistor, 541b: transistor, 542: transistor, 543: transistor, 551: light-emitting portion, 552: driver circuit portion, 553: driver circuit portion, 1100: glass substrate, 1101: first electrode, 1103: second electrode, 1111: hole-injection layer, 1112: hole-transport layer, 1113: light-emitting layer, 1114: electron-transport layer, 1115: electron-injection layer, 7100: television device, 7101: housing, 7102: display portion, 7103: stand, 7111: remote controller, 7200: computer, 7201: main body, 7202: housing, 7203: display portion, 7204: keyboard, 7205: external connection port, 7206: pointing device, 7300: portable game machine, 7301a: housing, 7301b: housing, 7302: joint portion, 7303a: display portion, 7303b: display portion, 7304: speaker portion, 7305: recording medium insertion portion, 7306: operation key, 7307: connection terminal, 7308: sensor, 7400: cellular phone, 7401: housing, 7402: display portion, 7403: operation button, 7404: external connection port, 7405: speaker, 7406: microphone, 7500: tablet terminal, 7501a: housing, 7501b: housing, 7502a: display portion, 7502b: display portion, 7503: hinge, 7504: power switch, 7505: operation key, 7506: speaker, 7601: lighting portion, 7602: shade, 7603: adjustable arm, 7604: support, 7605: base, 7606: power switch, 7701: lamp, 7702: lamp, and 7703: desk lamp.

This application is based on Japanese Patent Application serial no. 2012-172944 filed with Japan Patent Office on Aug. 3, 2012 and Japanese Patent Application serial no. 2013-045127 filed with Japan Patent Office on Mar. 7, 2013, the entire contents of which are hereby incorporated by reference.

16. The light-emitting element according to claim 9, wherein the third organic compound represents Formula (128),
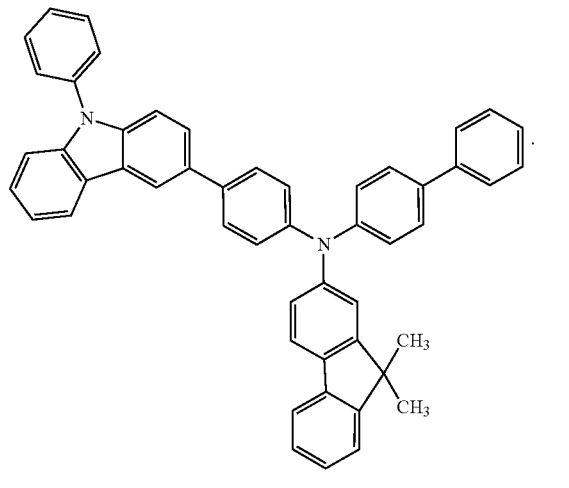

The invention claimed is:
1. A light-emitting element comprising:
an anode,
a cathode,
a light-emitting layer comprising a first organic compound, a second organic compound, and a phosphorescent compound,
a first layer between the anode and the light-emitting layer,
a second layer between the cathode and the light-emitting layer,
wherein the first layer comprises a third organic compound represented by General Formula (G0),

(G0)

wherein Ar$^1$ and Ar$^2$ each independently represent a substituted or unsubstituted fluorenyl group, a substituted or unsubstituted spirofluorenyl group, or a substituted or unsubstituted biphenyl group,
wherein Ar$^3$ represents a substituent including a 9 aryl-9H-carbazol-3-yl skeleton, and
wherein the aryl group of the 9-aryl-9H-carbazol-3-yl skeleton represents an unsubstituted phenyl group or a phenyl group having as a substituent at least one alkyl group having 1 to 10 carbon atoms, an unsubstituted biphenyl group or a biphenyl group having as a substituent at least one alkyl group having 1 to 10 carbon atoms, an unsubstituted terphenyl group or a terphenyl group having as a substituent at least one alkyl group having 1 to 10 carbon atoms.

2. The light-emitting element according to claim 1,
wherein a molecular weight of the third organic compound is greater than or equal to 500 and less than or equal to 2000.

3. The light-emitting element according to claim 1,
wherein the first layer further comprises an acceptor, and
wherein a molecular weight of the third organic compound is greater than or equal to 500 and less than or equal to 2000.

4. The light-emitting element according to claim 1,
wherein a molecular weight of the third organic compound is greater than or equal to 500 and less than or equal to 2000, and
wherein the second layer comprises a heteroaromatic compound.

5. The light-emitting element according to claim 1,
wherein the first layer further comprises an acceptor,
wherein a molecular weight of the third organic compound is greater than or equal to 500 and less than or equal to 2000, and
wherein the second layer comprises a heteroaromatic compound.

6. The light-emitting element according to claim 1,
wherein the first organic compound and the second organic compound form an exciplex, and
wherein an emission spectrum of the exciplex overlaps with an adsorption band of the phosphorescent compound which is located on the longest wavelength side.

7. The light-emitting element according to claim 1,
wherein the third organic compound is represented by General Formula (G1),

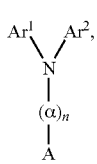

(G1)

wherein α represents a substituted or unsubstituted phenylene group or a substituted or unsubstituted biphenyldiyl group,
wherein n represents 0 or 1, and
wherein A represents a substituted or unsubstituted 3-carbazolyl group.

8. The light-emitting element according to claim 1,
wherein the third organic compound represents Formula (128),

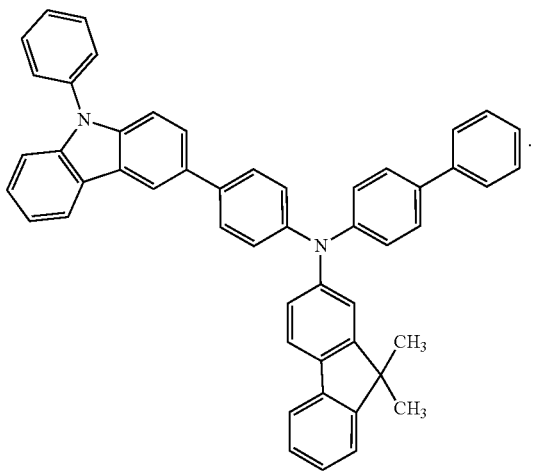

(128)

9. A light-emitting element comprising:
an anode,
a cathode,
a light-emitting layer comprising a first organic compound, a second organic compound, and a phosphorescent compound,
a first layer between the anode and the light-emitting layer,
a second layer between the cathode and the light-emitting layer,
wherein the first layer comprises a third organic compound represented by General Formula (G0),

(G0)

wherein $Ar^1$ and $Ar^2$ each independently represent a substituted or unsubstituted fluorenyl group, a substituted or unsubstituted spirofluorenyl group, or a substituted or unsubstituted biphenyl group,
wherein $Ar^3$ represents a substituent including a carbazole skeleton, and
wherein a triplet excitation energy level of each of the first organic compound and the second organic compound is higher than a triplet excitation energy level of the phosphorescent compound.

10. The light-emitting element according to claim 9,
wherein a molecular weight of the third organic compound is greater than or equal to 500 and less than or equal to 2000.

11. The light-emitting element according to claim 9,
wherein the first layer further comprises an acceptor,
wherein a molecular weight of the third organic compound is greater than or equal to 500 and less than or equal to 2000.

12. The light-emitting element according to claim 9,
wherein a molecular weight of the third organic compound is greater than or equal to 500 and less than or equal to 2000, and
wherein the second layer comprises a heteroaromatic compound.

13. The light-emitting element according to claim 9,
wherein the first layer further comprises an acceptor,
wherein a molecular weight of the third organic compound is greater than or equal to 500 and less than or equal to 2000, and
wherein the second layer comprises a heteroaromatic compound.

14. The light-emitting element according to claim 9,
wherein the first organic compound and the second organic compound form an exciplex, and
wherein an emission spectrum of the exciplex overlaps with an adsorption band of the phosphorescent compound which is located on the longest wavelength side.

15. The light-emitting element according to claim 9,
wherein the third organic compound is represented by General Formula (G1),

(G1)

wherein α represents a substituted or unsubstituted phenylene group or a substituted or unsubstituted biphenyldiyl group,
wherein n represents 0 or 1, and
wherein A represents a substituted or unsubstituted 3-carbazolyl group.